United States Patent
Kamal et al.

(10) Patent No.: US 9,878,977 B2
(45) Date of Patent: Jan. 30, 2018

(54) N-((3,4,5-TRIMETHOXYSTYRYL)ARYL) CINNAMAMIDE COMPOUNDS AS POTENTIAL ANTICANCER AGENTS AND PROCESS FOR THE PREPARATION THEREOF

(71) Applicant: COUNCIL OF SCIENTIFIC & INDUSTRIAL RESEARCH, New Delhi (IN)

(72) Inventors: Ahmed Kamal, Hyderabad (IN); Shaik Bajee, Hyderabad (IN); Challa Ratna Reddy, Hyderabad (IN); Mohammed Shaheer Malik, Hyderabad (IN); Vadithe Lakshma Nayak, Hyderabad (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/504,985

(22) PCT Filed: Aug. 18, 2015

(86) PCT No.: PCT/IN2015/050094
§ 371 (c)(1),
(2) Date: Feb. 17, 2017

(87) PCT Pub. No.: WO2016/027282
PCT Pub. Date: Feb. 25, 2016

(65) Prior Publication Data
US 2017/0240503 A1    Aug. 24, 2017

(30) Foreign Application Priority Data
Aug. 20, 2014    (IN) .......................... 2355/DEL/2014

(51) Int. Cl.
C07C 231/02    (2006.01)
C07C 233/29    (2006.01)
C07C 235/38    (2006.01)
C07D 209/18    (2006.01)

(52) U.S. Cl.
CPC .......... *C07C 235/38* (2013.01); *C07C 231/02* (2013.01); *C07C 233/29* (2013.01); *C07D 209/18* (2013.01)

(58) Field of Classification Search
None
See application file for complete search history.

(56) References Cited

PUBLICATIONS

Leslie et al., J. Med. Chem., vol. 53, No. 10, May 27, 2010, pp. 3964-3972.*

* cited by examiner

*Primary Examiner* — Alicia L Otton
(74) *Attorney, Agent, or Firm* — Seyfarth Shaw LLP

(57) ABSTRACT

The present invention provides a compound of general formula A, useful as potential anticancer agents against human cancer cell lines and process for the preparation thereof. [Formula should be entered here] General formula A where in B selected from aryl, heteroaryl and fused heteroaryl ring R and X selected from H, hydroxy, alkyl, alkoxy, prop-2-ynyloxy, allyloxy, halo, alkylhalides, alkoxy halides, nitro, amine.

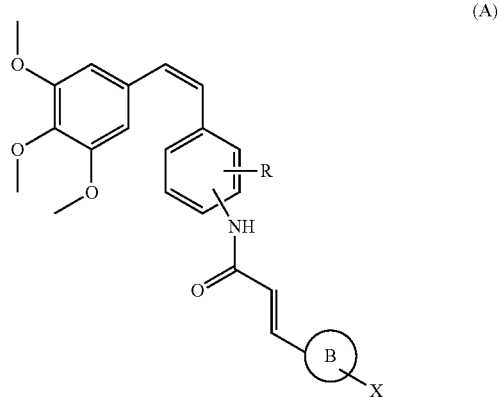

5 Claims, No Drawings

N-((3,4,5-TRIMETHOXYSTYRYL)ARYL) CINNAMAMIDE COMPOUNDS AS POTENTIAL ANTICANCER AGENTS AND PROCESS FOR THE PREPARATION THEREOF

FIELD OF THE INVENTION

The present invention relates to N-((3,4,5-trimethoxystyryl)aryl)cinnamamide compounds as potential anticancer agents and process for the preparation thereof. Particularly, the present invention relates to N-((3,4,5-trimethoxystyryl)aryl)cinnamamides of general formula A.

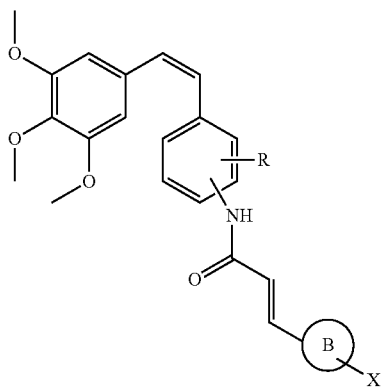

where in
B selected from aryl, heteroaryl and fused heteroaryl ring
R and X selected from H, hydroxy, alkyl, alkoxy, prop-2-ynyloxy, allyloxy, halo, alkylhalides, alkoxy halides, nitro, amine

BACKGROUND OF THE INVENTION

Microtubules are dynamic copolymers of α and β tubulin sub units, which play a critical role in many cellular process, maintenance of cell shape, motility, cell signalling and serve to organize and segregate chromosomes during the mitosis (Jordan M A, Wilson L, Microtubules as a target for anticancer drugs, *Nat. Rev. Cancer*, 2004, (4), 253-265; Prasad V. Jallepalli & Christoph Lengauer Chromosome segregation and cancer: cutting through the mystery *Nature Reviews Cancer*, 1, 109-117). Chemical agents targeting the microtubules dynamics by the inhibition of tubulin protein have emerged as potential chemotherapeutic compounds for the treatment of various cancers. These agents are known to bind to different domain of the tubulin protein and prevent the polymerization or depolymerisation of the microtubules resulting in mitotic spindle arrest (Jordan, A.; Hadfield, J. A.; Lawrence, N. J.; McGowan, A. T. Tubulin as a target for anticancer drugs: Agents which interact with the mitotic spindle. *Med. Res. Rev.* 1998, 18, 259-296).

Colchicine (S1) and combretastatins (CA-4; S2) are well established natural agents that effectively bind at the colchicine site of tubulin and inhibit the polymerization resulting in the arrest of cell proliferation (McGowan A. T, Fox B. W, Structural and biochemical comparison of the anti-mitotic agents colchicines, combretastatin A4 and amphethinile, *Anti-Cancer Drug Design*, 1989, 3, 249). CA-4 is one of the preferred lead compounds in the development of new tubulin inhibitors because of its high potency and the limitation of low aqueous solubility. To overcome this, CA-4 based analogues such as CA4P, AVE8062 and AVE8063 have been developed and are undergoing clinical trials (Tron, G. C.; Pirali, T.; Sorba, G.; Pagliai, F.; Busacca, S.; Genazzani, A. A. Medicinal chemistry of combretastatin A4: present and future directions. *J. Med. Chem.* 2006, 49, 3033-3044). Recently it has been reported that a new class of combretastatins such as (Z)-5-(3, 5-dimethoxystyryl)-2-methoxyaniline (S3) inhibits tubulin polymerization stronger than CA-4 by five folds. This new class binds at colchicine binding site and exhibit potent inhibition of cell proliferation against CA-4 resistant BMEC and HT-29 cell lines (Simoni D, Romagnoli R, Baruchello R, Rondanin R, Grisolia G, Eleopra M, Rizzi M, Tolomeo M, Giannini G, Alloatti D, Castorina M, Marcellini M, Pisano C, Novel A-ring and B-ring modified combretastatin A-4 (CA-4) analogues endowed with interesting cytotoxic activity, *J. Med. Chem.* 2008, 51, (19), 6211-6215).

More recently a report revealed that a series of phenylcinnamide derivatives (S4) exhibits significant activities against a number of tumor cell lines including multidrug resistant phenotype and it was also demonstrated that these compounds represent a new class of inhibitors of tubulin polymerization (Benjamin J. Leslie, Clinton R. Holaday, Tran Nguyen, and Paul J. Hergenrother, Phenylcinnamides as Novel Antimitotic Agents, *J. Med. Chem.* 2010, 53, 3964-3972). In continuation of these efforts and our interest in the structural modifications of the combretastatin A4, we describe herein an efficient access to the construction of some new N-(3,4,5-trimethoxystyryl)aryl)cinnamamides incorporating the phenylcinnamide and CA-4 pharmacophoric structures with improved cytotoxicity.

S1

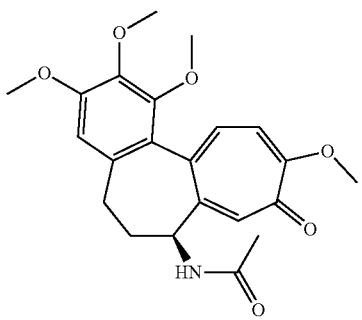

S2

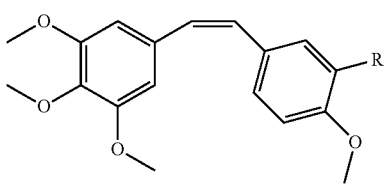

R = OH(CA4)
R = OPO$_3$Na$_2$ (CA4P)
R = NH$_2$·HCl (AVE8062)
R = NH2 serine (AVE 8063)

S3

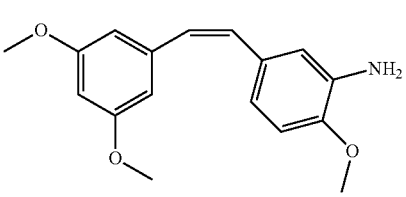

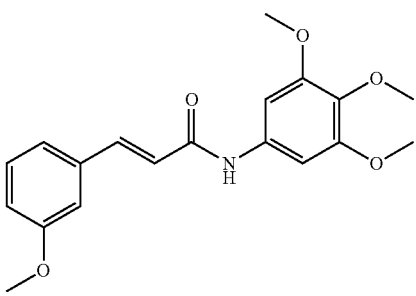

S4

OBJECTIVES OF THE INVENTION

The main objective of the present invention to provide N-((3,4,5-trimethoxystyryl) aryl)cinnamamides as potential anticancer agents targeting the tubulin polymerization. Yet another objective of this invention is to provide a process for the preparation of these novel N-((3,4,5-trimethoxystyryl) aryl)cinnamamide compounds.

SUMMARY OF THE INVENTION

Accordingly, the present invention provides N-((3,4,5-trimethoxystyryl)aryl)cinnamamide compounds of the general formula A

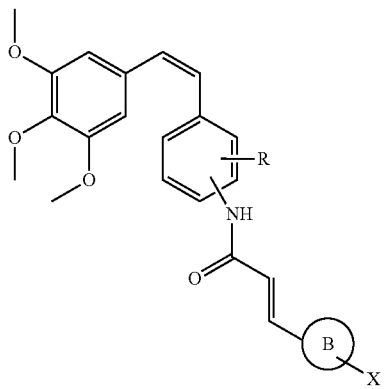

where in
  B selected from aryl, heteroaryl and fused heteroaryl ring
  R and X selected from H, hydroxy, alkyl, alkoxy, prop-2-ynyloxy, allyloxy, halo, alkylhalides, alkoxy halides, nitro, amine In an embodiment of the present invention some of the novel N-((3,4,5-trimethoxystyryl)aryl)cinnamamide compounds of general formula A is represented by the compounds of general formula 8a-8af, 9a-9af, 10a-10af, 11a-11af, 12a-12af, 13a-13af, 14a-14af, 15a-15af, 16a-16af, 17a-17af, 18a-18af, 19a-19af, 20a-20af, 21a-21af, 22a-22af, 23a-23af, 24a-24af.

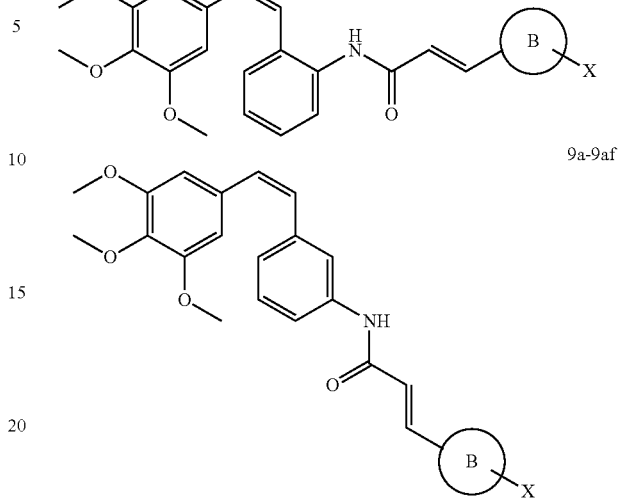

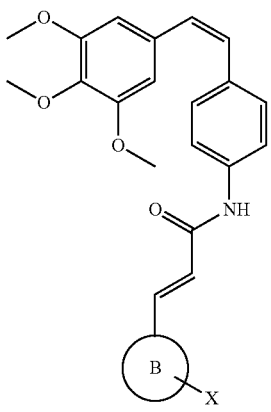

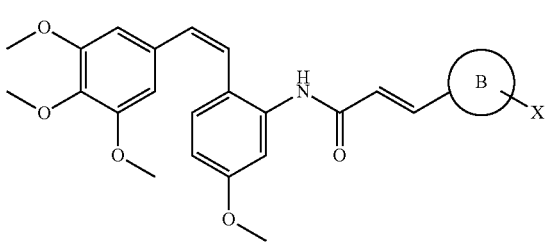

14a-14af
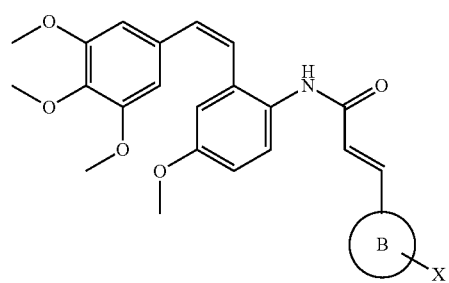
15a-15af
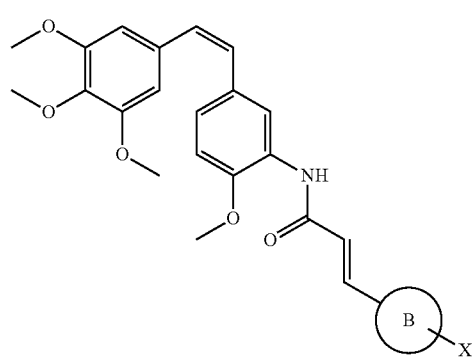
16a-16af
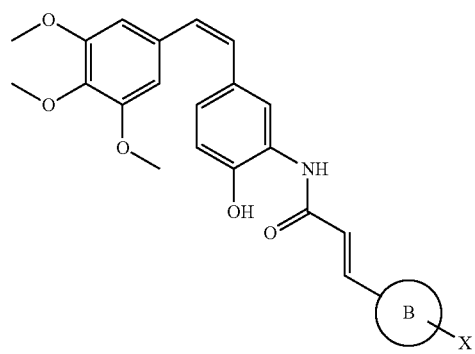
17a-17af
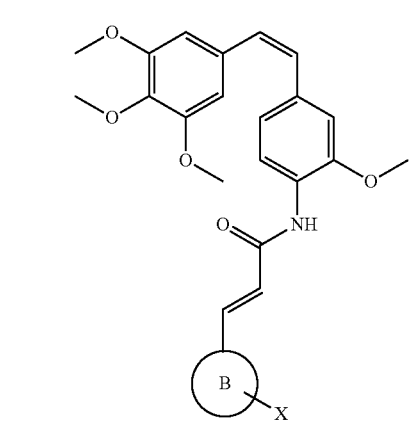
18a-18af
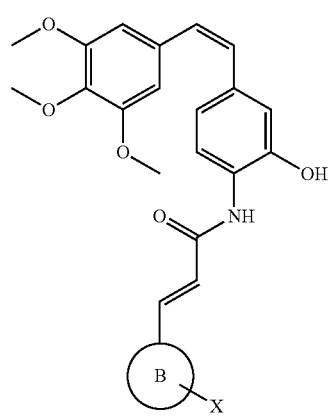
19a-19af
20a-20af
21a-21af
22a-22af
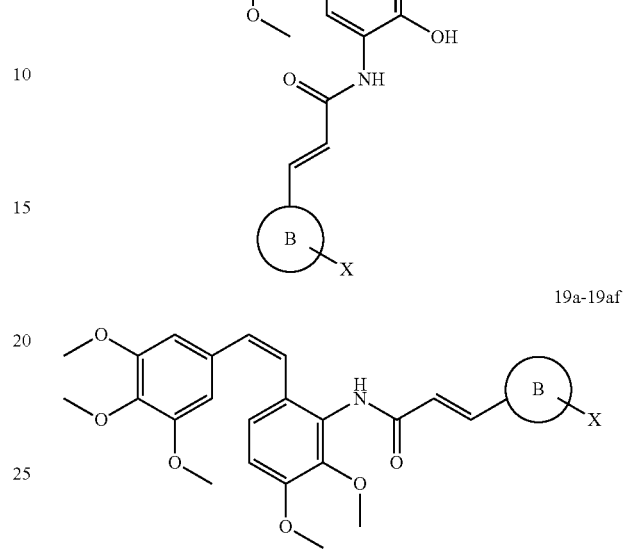

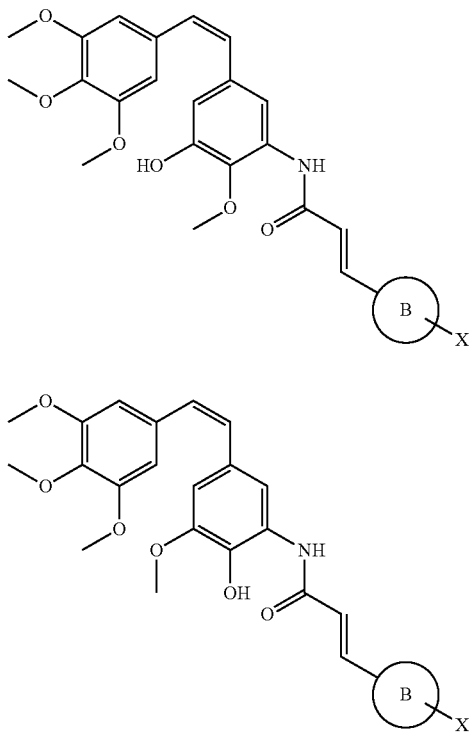

where in
B selected from aryl, heteroaryl and fused heteroaryl ring
X selected from H, hydroxy, alkyl, alkoxy, prop-2-ynyloxy, allyloxy, halo, alkylhalides, alkoxy halides, nitro, amine In yet another embodiment of the invention wherein some of the N-((3,4,5-trimethoxystyryl)aryl)cinnamamides are represented by the following compounds:

N-(2-(3,4,5-Trimethoxystyryl)phenyl)cinnamamide(8a)
(E)-3-(2-Methoxyphenyl)-N-(2-(3,4,5-trimethoxystyryl)phenyl)acrylamide(8b)
(E)-3-(2-Nitrophenyl)-N-(2-(3,4,5-trimethoxystyryl)phenyl)acrylamide(8d)
(E)-3-(2-Aminophenyl)-N-(2-(3,4,5-trimethoxystyryl)phenyl)acrylamide(8e)
(E)-3-(3-Methoxyphenyl)-N-(2-(3,4,5-trimethoxystyryl)phenyl)acrylamide(8f)
(E)-3-(3-Hydroxyphenyl)-N-(2-(3,4,5-trimethoxystyryl)phenyl)acrylamide(8g)
(E)-3-(3-(Prop-2-ynyloxy)phenyl)-N-(2-(3,4,5-trimethoxystyryl)phenyl)acrylamide(8h)
(E)-3-(3-(Allyloxy)phenyl)-N-(2-(3,4,5-trimethoxystyryl)phenyl)acrylamide(8i)
(E)-3-(3-Nitrophenyl)-N-(2-(3,4,5-trimethoxystyryl)phenyl)acrylamide(8j)
(E)-3-(3-Aminophenyl)-N-(2-(3,4,5-trimethoxystyryl)phenyl)acrylamide(8k)
(E)-3-(4-Methoxyphenyl)-N-(2-(3,4,5-trimethoxystyryl)phenyl)acrylamide(8l)
(E)-3-(4-Hydroxyphenyl)-N-(2-(3,4,5-trimethoxystyryl)phenyl)acrylamide(8m)
(E)-3-(4-(Trifluoromethyl)phenyl)-N-(2-(3,4,5-trimethoxystyryl)phenyl)acrylamide(8n)
(E)-3-(4-Nitrophenyl)-N-(2-(3,4,5-trimethoxystyryl)phenyl)acrylamide(8o)
(E)-3-(4-Aminophenyl)-N-(2-(3,4,5-trimethoxystyryl)phenyl)acrylamide(8p)
(E)-3-(4-Chlorophenyl)-N-(2-(3,4,5-trimethoxystyryl)phenyl)acrylamide(8q)
(E)-3-(4-Fluorophenyl)-N-(2-(3,4,5-trimethoxystyryl)phenyl)acrylamide(8r)
(E)-3-(3,4-Dimethoxyphenyl)-N-(2-(3,4,5-trimethoxystyryl)phenyl)acrylamide(8s)
(E)-3-(4-Hydroxy-3-methoxyphenyl)-N-(2-(3,4,5-trimethoxystyryl)phenyl)acrylamide(8t)
(E)-3-(3-Methoxy-4-nitrophenyl)-N-(2-(3,4,5-trimethoxystyryl)phenyl)acrylamide(8u)
(E)-3-(4-Amino-3-methoxyphenyl)-N-(2-(3,4,5-trimethoxystyryl)phenyl)acrylamide(8v)
(E)-3-(3,4-Dihydroxyphenyl)-N-(2-(3,4,5-trimethoxystyryl)phenyl)acrylamide(8w)
(E)-3-(3-Hydroxy-4-methoxyphenyl)-N-(2-(3,4,5-trimethoxystyryl)phenyl)acrylamide(8x)
(E)-3-(4-Methoxy-3-nitrophenyl)-N-(2-(3,4,5-trimethoxystyryl)phenyl)acrylamide(8y)
(E)-3-(3-Amino-4-methoxyphenyl)-N-(2-(3,4,5-trimethoxystyryl)phenyl)acrylamide(8z)
(E)-3-(3,4-Difluorophenyl)-N-(2-(3,4,5-trimethoxystyryl)phenyl)acrylamide(8aa)
(E)-3-(3,4,5-Trimethoxyphenyl)-N-(2-(3,4,5-trimethoxystyryl)phenyl)acrylamide(8ab)
(E)-3-(3,4-Dimethoxy-5-nitrophenyl)-N-(2-(3,4,5-trimethoxystyryl)phenyl)acrylamide(8ac)
(E)-3-(3-Amino-4,5-dimethoxyphenyl)-N-(2-(3,4,5-trimethoxystyryl)phenyl)acrylamide(8ad)
(E)-3-(1H-Indol-3-yl)-N-(2-(3,4,5-trimethoxystyryl)phenyl)acrylamide(8ae)
(E)-3-(1-Methyl-1H-indol-3-yl)-N-(2-(3,4,5-trimethoxystyryl)phenyl)acrylamide(8af)
N-(3-(3,4,5-Trimethoxystyryl)phenyl)cinnamamide(9a)
(E)-3-(2-Methoxyphenyl)-N-(3-(3,4,5-trimethoxystyryl)phenyl)acrylamide(9b)
(E)-3-(2-Hydroxyphenyl)-N-(3-(3,4,5-trimethoxystyryl)phenyl)acrylamide(9c)
(E)-3-(2-Nitrophenyl)-N-(3-(3,4,5-trimethoxystyryl)phenyl)acrylamide(9d)
(E)-3-(2-Aminophenyl)-N-(3-(3,4,5-trimethoxystyryl)phenyl)acrylamide(9e)
(E)-3-(3-Methoxyphenyl)-N-(3-(3,4,5-trimethoxystyryl)phenyl)acrylamide(9f)
(E)-3-(3-Hydroxyphenyl)-N-(3-(3,4,5-trimethoxystyryl)phenyl)acrylamide(9g)
(E)-3-(3-(Prop-2-ynyloxy)phenyl)-N-(3-(3,4,5-trimethoxystyryl)phenyl)acrylamide(9h)
(E)-3-(3-(Allyloxy)phenyl)-N-(3-(3,4,5-trimethoxystyryl)phenyl)acrylamide(9i)
(E)-3-(3-Nitrophenyl)-N-(3-(3,4,5-trimethoxystyryl)phenyl)acrylamide(9j)
(E)-3-(3-Aminophenyl)-N-(3-(3,4,5-trimethoxystyryl)phenyl)acrylamide(9k)
(E)-3-(4-Methoxyphenyl)-N-(3-(3,4,5-trimethoxystyryl)phenyl)acrylamide(9l)
(E)-3-(4-Hydroxyphenyl)-N-(3-(3,4,5-trimethoxystyryl)phenyl)acrylamide(9m)
(E)-3-(4-(Trifluoromethyl)phenyl)-N-(3-(3,4,5-trimethoxystyryl)phenyl)acrylamide(9n)
(E)-3-(4-Nitrophenyl)-N-(3-(3,4,5-trimethoxystyryl)phenyl)acrylamide(9o)
(E)-3-(4-Aminophenyl)-N-(3-(3,4,5-trimethoxystyryl)phenyl)acrylamide(9p)
(E)-3-(4-Chlorophenyl)-N-(3-(3,4,5-trimethoxystyryl)phenyl)acrylamide(9q)

(E)-3-(4-Fluorophenyl)-N-(3-(3,4,5-trimethoxystyryl)phenyl)acrylamide(9r)
(E)-3-(3,4-Dimethoxyphenyl)-N-(3-(3,4,5-trimethoxystyryl)phenyl)acrylamide(9s)
(E)-3-(4-Hydroxy-3-methoxyphenyl)-N-(3-(3,4,5-trimethoxystyryl)phenyl)acrylamide(9t)
(E)-3-(3-Methoxy-4-nitrophenyl)-N-(3-(3,4,5-trimethoxystyryl)phenyl)acrylamide(9u)
(E)-3-(4-Amino-3-methoxyphenyl)-N-(3-(3,4,5-trimethoxystyryl)phenyl)acrylamide(9v)
(E)-3-(3,4-Dihydroxyphenyl)-N-(3-(3,4,5-trimethoxystyryl)phenyl)acrylamide(9w)
(E)-3-(3-Hydroxy-4-methoxyphenyl)-N-(3-(3,4,5-trimethoxystyryl)phenyl)acrylamide(9x)
(E)-3-(4-Methoxy-3-nitrophenyl)-N-(3-(3,4,5-trimethoxystyryl)phenyl)acrylamide(9y)
(E)-3-(3-Amino-4-methoxyphenyl)-N-(3-(3,4,5-trimethoxystyryl)phenyl)acrylamide(9z)
(E)-3-(3,4-Difluorophenyl)-N-(3-(3,4,5-trimethoxystyryl)phenyl)acrylamide(9aa)
(E)-3-(3,4,5-Trimethoxyphenyl)-N-(3-(3,4,5-trimethoxystyryl)phenyl)acrylamide(9ab)
(E)-3-(3,4-Dimethoxy-5-nitrophenyl)-N-(3-(3,4,5-trimethoxystyryl)phenyl)acrylamide(9ac)
(E)-3-(3-Amino-4,5-dimethoxyphenyl)-N-(3-(3,4,5-trimethoxystyryl)phenyl)acrylamide(9ad)
(E)-3-(1H-Indol-3-yl)-N-(3-(3,4,5-trimethoxystyryl)phenyl)acrylamide(9ae)
(E)-3-(1-Methyl-1H-indol-3-yl)-N-(3-(3,4,5-trimethoxystyryl)phenyl)acrylamide(9af)
N-(4-(3,4,5-Trimethoxystyryl)phenyl)cinnamamide(10a)
(E)-3-(2-Methoxyphenyl)-N-(4-(3,4,5-trimethoxystyryl)phenyl)acrylamide(10b)
(E)-3-(2-hydroxyphenyl)-N-(4-(3,4,5-trimethoxystyryl)phenyl)acrylamide(10c)
(E)-3-(2-Nitrophenyl)-N-(4-(3,4,5-trimethoxystyryl)phenyl)acrylamide(10d)
(E)-3-(2-Aminophenyl)-N-(4-(3,4,5-trimethoxystyryl)phenyl)acrylamide(10e)
(E)-3-(3-Methoxyphenyl)-N-(4-(3,4,5-trimethoxystyryl)phenyl)acrylamide(10f)
(E)-3-(3-Hydroxyphenyl)-N-(4-(3,4,5-trimethoxystyryl)phenyl)acrylamide(10g)
(E)-3-(3-(Prop-2-ynyloxy)phenyl)-N-(4-(3,4,5-trimethoxystyryl)phenyl)acrylamide(10h)
(E)-3-(3-(Allyloxy)phenyl)-N-(4-(3,4,5-trimethoxystyryl)phenyl)acrylamide(10i)
(E)-3-(3-Nitrophenyl)-N-(4-(3,4,5-trimethoxystyryl)phenyl)acrylamide(10j)
(E)-3-(3-Aminophenyl)-N-(4-(3,4,5-trimethoxystyryl)phenyl)acrylamide(10k)
(E)-3-(4-Methoxyphenyl)-N-(4-(3,4,5-trimethoxystyryl)phenyl)acrylamide(10l)
(E)-3-(4-Hydroxyphenyl)-N-(4-(3,4,5-trimethoxystyryl)phenyl)acrylamide(10m)
(E)-3-(4-(Trifluoromethyl)phenyl)-N-(4-(3,4,5-trimethoxystyryl)phenyl)acrylamide(10n)
(E)-3-(4-Nitrophenyl)-N-(4-(3,4,5-trimethoxystyryl)phenyl)acrylamide(10o)
(E)-3-(4-Aminophenyl)-N-(4-(3,4,5-trimethoxystyryl)phenyl)acrylamide(10p)
(E)-3-(4-Chlorophenyl)-N-(4-(3,4,5-trimethoxystyryl)phenyl)acrylamide(10q)
(E)-3-(4-Fluorophenyl)-N-(4-(3,4,5-trimethoxystyryl)phenyl)acrylamide(10r)
(E)-3-(3,4-Dimethoxyphenyl)-N-(4-(3,4,5-trimethoxystyryl)phenyl)acrylamide(10s)
(E)-3-(4-Hydroxy-3-methoxyphenyl)-N-(4-(3,4,5-trimethoxystyryl)phenyl)acrylamide(10t)
(E)-3-(3-Methoxy-4-nitrophenyl)-N-(4-(3,4,5-trimethoxystyryl)phenyl)acrylamide(10u)
(E)-3-(4-Amino-3-methoxyphenyl)-N-(4-(3,4,5-trimethoxystyryl)phenyl)acrylamide(10v)
(E)-3-(3,4-Dihydroxyphenyl)-N-(4-(3,4,5-trimethoxystyryl)phenyl)acrylamide(10w)
(E)-3-(3-Hydroxy-4-methoxyphenyl)-N-(4-(3,4,5-trimethoxystyryl)phenyl)acrylamide(10x)
(E)-3-(4-Methoxy-3-nitrophenyl)-N-(4-(3,4,5-trimethoxystyryl)phenyl)acrylamide(10y)
(E)-3-(3-Amino-4-methoxyphenyl)-N-(4-(3,4,5-trimethoxystyryl)phenyl)acrylamide(10z)
(E)-3-(3,4-Difluorophenyl)-N-(4-(3,4,5-trimethoxystyryl)phenyl)acrylamide(10aa)
(E)-3-(3,4,5-Trimethoxyphenyl)-N-(4-(3,4,5-trimethoxystyryl)phenyl)acrylamide(10ab)
(E)-3-(3,4-Dimethoxy-5-nitrophenyl)-N-(4-(3,4,5-trimethoxystyryl)phenyl)acrylamide(10ac)
(E)-3-(3-Amino-4,5-dimethoxyphenyl)-N-(4-(3,4,5-trimethoxystyryl)phenyl)acrylamide(10ad)
(E)-3-(1H-Indol-3-yl)-N-(4-(3,4,5-trimethoxystyryl)phenyl)acrylamide(10ae)
(E)-3-(1-Methyl-1H-indol-3-yl)-N-(4-(3,4,5-trimethoxystyryl)phenyl)acrylamide(10af)
N-(2-Methoxy-6-(3,4,5-trimethoxystyryl)phenyl)cinnamamide(11a)
(E)-N-(2-Methoxy-6-(3,4,5-trimethoxystyryl)phenyl)-3-(2-methoxyphenyl)acrylamide(11b)
(E)-3-(2-Hydroxyphenyl)-N-(2-methoxy-6-(3,4,5-trimethoxystyryl)phenyl)acrylamide(11c)
(E)-N-(2-Methoxy-6-(3,4,5-trimethoxystyryl)phenyl)-3-(2-nitrophenyl)acrylamide(11d)
(E)-3-(2-Aminophenyl)-N-(2-methoxy-6-(3,4,5-trimethoxystyryl)phenyl)acrylamide(11e)
(E)-N-(2-Methoxy-6-(3,4,5-trimethoxystyryl)phenyl)-3-(3-methoxyphenyl)acrylamide(11f)
(E)-3-(3-Hydroxyphenyl)-N-(2-methoxy-6-(3,4,5-trimethoxystyryl)phenyl)acrylamide(11g)
(E)-N-(2-Methoxy-6-(3,4,5-trimethoxystyryl)phenyl)-3-(3-(prop-2-ynyloxy)phenyl)acrylamide(11h)
(E)-3-(3-(Allyloxy)phenyl)-N-(2-methoxy-6-(3,4,5-trimethoxystyryl)phenyl)acrylamide(11i)
(E)-N-(2-Methoxy-6-(3,4,5-trimethoxystyryl)phenyl)-3-(3-nitrophenyl)acrylamide(11j)
(E)-3-(3-Aminophenyl)-N-(2-methoxy-6-(3,4,5-trimethoxystyryl)phenyl)acrylamide(11k)
(E)-N-(2-Methoxy-6-(3,4,5-trimethoxystyryl)phenyl)-3-(4-methoxyphenyl)acrylamide(11l)
(E)-3-(4-Hydroxyphenyl)-N-(2-methoxy-6-(3,4,5-trimethoxystyryl)phenyl)acrylamide(11m)
(E)-N-(2-Methoxy-6-(3,4,5-trimethoxystyryl)phenyl)-3-(4-(trifluoromethyl)phenyl)acrylamide(11n)
(E)-N-(2-Methoxy-6-(3,4,5-trimethoxystyryl)phenyl)-3-(4-nitrophenyl)acrylamide(11o)
(E)-3-(4-Aminophenyl)-N-(2-methoxy-6-(3,4,5-trimethoxystyryl)phenyl)acrylamide(11p)
(E)-3-(4-Chlorophenyl)-N-(2-methoxy-6-(3,4,5-trimethoxystyryl)phenyl)acrylamide(11q)
(E)-3-(4-Fluorophenyl)-N-(2-methoxy-6-(3,4,5-trimethoxystyryl)phenyl)acrylamide(11r)
(E)-3-(3,4-Dimethoxyphenyl)-N-(2-methoxy-6-(3,4,5-trimethoxystyryl)phenyl)acrylamide(11s)
(E)-3-(4-Hydroxy-3-methoxyphenyl)-N-(2-methoxy-6-(3,4,5-trimethoxystyryl)phenyl)acrylamide(11t)

(E)-3-(3-Methoxy-4-nitrophenyl)-N-(2-methoxy-6-(3,4,5-trimethoxystyryl)phenyl)acrylamide(11u)
(E)-3-(4-Amino-3-methoxyphenyl)-N-(2-methoxy-6-(3,4,5-trimethoxystyryl)phenyl)acrylamide(11v)
(E)-3-(3,4-Dihydroxyphenyl)-N-(2-methoxy-6-(3,4,5-trimethoxystyryl)phenyl)acrylamide(11w)
(E)-3-(3-Hydroxy-4-methoxyphenyl)-N-(2-methoxy-6-(3,4,5-trimethoxystyryl)phenyl)acrylamide(11X)
(E)-3-(4-Methoxy-3-nitrophenyl)-N-(2-methoxy-6-(3,4,5-trimethoxystyryl)phenyl)acrylamide(11y)
(E)-3-(3-Amino-4-methoxyphenyl)-N-(2-methoxy-6-(3,4,5-trimethoxystyryl)phenyl)acrylamide(11z)
(E)-3-(3,4-Difluorophenyl)-N-(2-methoxy-6-(3,4,5-trimethoxystyryl)phenyl)acrylamide(11aa)
(E)-N-(2-Methoxy-6-(3,4,5-trimethoxystyryl)phenyl)-3-(3,4,5-trimethoxyphenyl)acrylamide(11ab)
(E)-3-(3,4-Dimethoxy-5-nitrophenyl)-N-(2-methoxy-6-(3,4,5-trimethoxystyryl)phenyl)acrylamide(11ac)
(E)-3-(3-Amino-4,5-dimethoxyphenyl)-N-(2-methoxy-6-(3,4,5-trimethoxystyryl)phenyl)acrylamide(11ad)
(E)-3-(1H-Indol-3-yl)-N-(2-methoxy-6-(3,4,5-trimethoxystyryl)phenyl)acrylamide(11ae)
(E)-N-(2-Methoxy-6-(3,4,5-trimethoxystyryl)phenyl)-3-(1-methyl-1H-indol-3-yl)acrylamide(11af)
N-(2-Hydroxy-6-(3,4,5-trimethoxystyryl)phenyl)cinnamamide(12a)
(E)-N-(2-Hydroxy-6-(3,4,5-trimethoxystyryl)phenyl)-3-(2-methoxyphenyl)acrylamide(12b)
(E)-N-(2-Hydroxy-6-(3,4,5-trimethoxystyryl)phenyl)-3-(2-hydroxyphenyl)acrylamide(12c)
(E)-N-(2-Hydroxy-6-(3,4,5-trimethoxystyryl)phenyl)-3-(2-nitrophenyl)acrylamide(12d)
(E)-3-(2-Aminophenyl)-N-(2-hydroxy-6-(3,4,5-trimethoxystyryl)phenyl)acrylamide(12e)
(E)-N-(2-Hydroxy-6-(3,4,5-trimethoxystyryl)phenyl)-3-(3-methoxyphenyl)acrylamide(12f)
(E)-N-(2-Hydroxy-6-(3,4,5-trimethoxystyryl)phenyl)-3-(3-hydroxyphenyl)acrylamide(12g)
(E)-N-(2-Hydroxy-6-(3,4,5-trimethoxystyryl)phenyl)-3-(3-(prop-2-ynyloxy)phenyl)acrylamide(12h)
(E)-3-(3-(Allyloxy)phenyl)-N-(2-hydroxy-6-(3,4,5-trimethoxystyryl)phenyl)acrylamide(12i)
(E)-N-(2-Hydroxy-6-(3,4,5-trimethoxystyryl)phenyl)-3-(3-nitrophenyl)acrylamide(12j)
(E)-3-(3-Aminophenyl)-N-(2-hydroxy-6-(3,4,5-trimethoxystyryl)phenyl)acrylamide(12k)
(E)-N-(2-Hydroxy-6-(3,4,5-trimethoxystyryl)phenyl)-3-(4-methoxyphenyl)acrylamide(12l)
(E)-N-(2-Hydroxy-6-(3,4,5-trimethoxystyryl)phenyl)-3-(4-hydroxyphenyl)acrylamide(12m)
(E)-N-(2-Hydroxy-6-(3,4,5-trimethoxystyryl)phenyl)-3-(4-(trifluoromethyl)phenyl)acrylamide(12n)
(E)-N-(2-Hydroxy-6-(3,4,5-trimethoxystyryl)phenyl)-3-(4-nitrophenyl)acrylamide(12o)
(E)-3-(4-Aminophenyl)-N-(2-hydroxy-6-(3,4,5-trimethoxystyryl)phenyl)acrylamide(12p)
(E)-3-(4-Chlorophenyl)-N-(2-hydroxy-6-(3,4,5-trimethoxystyryl)phenyl)acrylamide(12q)
(E)-3-(4-Fluorophenyl)-N-(2-hydroxy-6-(3,4,5-trimethoxystyryl)phenyl)acrylamide(12r)
(E)-3-(3,4-Dimethoxyphenyl)-N-(2-hydroxy-6-(3,4,5-trimethoxystyryl)phenyl)acrylamide(12s)
(E)-3-(4-Hydroxy-3-methoxyphenyl)-N-(2-hydroxy-6-(3,4,5-trimethoxystyryl)phenyl)acrylamide(12t)
(E)-N-(2-hydroxy-6-(3,4,5-trimethoxystyryl)phenyl)-3-(3-methoxy-4-nitrophenyl)acrylamide(12u)
(E)-3-(4-Amino-3-methoxyphenyl)-N-(2-hydroxy-6-(3,4,5-trimethoxystyryl)phenyl)acrylamide(12v)
(E)-3-(3,4-Dihydroxyphenyl)-N-(2-hydroxy-6-(3,4,5-trimethoxystyryl)phenyl)acrylamide(12w)
(E)-3-(3-Hydroxy-4-methoxyphenyl)-N-(2-hydroxy-6-(3,4,5-trimethoxystyryl)phenyl)acrylamide(12x)
(E)-N-(2-Hydroxy-6-(3,4,5-trimethoxystyryl)phenyl)-3-(4-methoxy-3-nitrophenyl)acrylamide(12y)
(E)-3-(3-Amino-4-methoxyphenyl)-N-(2-hydroxy-6-(3,4,5-trimethoxystyryl)phenyl)acrylamide(12z)
(E)-3-(3,4-Difluorophenyl)-N-(2-hydroxy-6-(3,4,5-trimethoxystyryl)phenyl)acrylamide(12aa)
(E)-N-(2-Hydroxy-6-(3,4,5-trimethoxystyryl)phenyl)-3-(3,4,5-trimethoxyphenyl)acrylamide(12ab)
(E)-3-(3,4-Dimethoxy-5-nitrophenyl)-N-(2-hydroxy-6-(3,4,5-trimethoxystyryl)phenyl)acrylamide(12ac)
(E)-3-(3-Amino-4,5-dimethoxyphenyl)-N-(2-hydroxy-6-(3,4,5-trimethoxystyryl)phenyl)acrylamide(12ad)
(E)-N-(2-Hydroxy-6-(3,4,5-trimethoxystyryl)phenyl)-3-(1H-indol-3-yl)acrylamide(12ae)
(E)-N-(2-Hydroxy-6-(3,4,5-trimethoxystyryl)phenyl)-3-(1-methyl-1H-indol-3-yl)acrylamide(12af)
N-(5-Methoxy-2-(3,4,5-trimethoxystyryl)phenyl)cinnamamide(13a)
(E)-N-(5-Methoxy-2-(3,4,5-trimethoxystyryl)phenyl)-3-(2-methoxyphenyl)acrylamide(13b)
(E)-3-(2-Hydroxyphenyl)-N-(5-methoxy-2-(3,4,5-trimethoxystyryl)phenyl)acrylamide(13c)
(E)-N-(5-Methoxy-2-(3,4,5-trimethoxystyryl)phenyl)-3-(2-nitrophenyl)acrylamide(13d)
(E)-3-(2-Aminophenyl)-N-(5-methoxy-2-(3,4,5-trimethoxystyryl)phenyl)acrylamide(13e)
(E)-N-(5-Methoxy-2-(3,4,5-trimethoxystyryl)phenyl)-3-(3-methoxyphenyl)acrylamide(13f)
(E)-3-(3-Hydroxyphenyl)-N-(5-methoxy-2-(3,4,5-trimethoxystyryl)phenyl)acrylamide(13g)
(E)-N-(5-Methoxy-2-(3,4,5-trimethoxystyryl)phenyl)-3-(3-(prop-2-ynyloxy)phenyl)acrylamide(13h)
(E)-3-(3-(Allyloxy)phenyl)-N-(5-methoxy-2-(3,4,5-trimethoxystyryl)phenyl)acrylamide(13i)
(E)-N-(5-Methoxy-2-(3,4,5-trimethoxystyryl)phenyl)-3-(3-nitrophenyl)acrylamide(13j)
(E)-3-(3-Aminophenyl)-N-(5-methoxy-2-(3,4,5-trimethoxystyryl)phenyl)acrylamide(13k)
(E)-N-(5-Methoxy-2-(3,4,5-trimethoxystyryl)phenyl)-3-(4-methoxyphenyl)acrylamide(13l)
(E)-3-(4-Hydroxyphenyl)-N-(5-methoxy-2-(3,4,5-trimethoxystyryl)phenyl)acrylamide(13m)
(E)-N-(5-methoxy-2-(3,4,5-trimethoxystyryl)phenyl)-3-(4-(trifluoromethyl)phenyl)acrylamide(13n)
(E)-N-(5-Methoxy-2-(3,4,5-trimethoxystyryl)phenyl)-3-(4-nitrophenyl)acrylamide(13o)
(E)-3-(4-Aminophenyl)-N-(5-methoxy-2-(3,4,5-trimethoxystyryl)phenyl)acrylamide(13p)
(E)-3-(4-Chlorophenyl)-N-(5-methoxy-2-(3,4,5-trimethoxystyryl)phenyl)acrylamide(13q)
(E)-3-(4-Fluorophenyl)-N-(5-methoxy-2-(3,4,5-trimethoxystyryl)phenyl)acrylamide(13r)
(E)-3-(3,4-Dimethoxyphenyl)-N-(5-methoxy-2-(3,4,5-trimethoxystyryl)phenyl)acrylamide(13s)
(E)-3-(4-Hydroxy-3-methoxyphenyl)-N-(5-methoxy-2-(3,4,5-trimethoxystyryl)phenyl)acrylamide(13t)
(E)-N-(5-Methoxy-2-(3,4,5-trimethoxystyryl)phenyl)-3-(3-methoxy-4-nitrophenyl)acrylamide(13u)
(E)-3-(4-Amino-3-methoxyphenyl)-N-(5-methoxy-2-(3,4,5-trimethoxystyryl)phenyl)acrylamide(13v)

(E)-3-(3,4-Dihydroxyphenyl)-N-(5-methoxy-2-(3,4,5-trimethoxystyryl)phenyl)acrylamide(13w)
(E)-3-(3-Hydroxy-4-methoxyphenyl)-N-(5-methoxy-2-(3,4,5-trimethoxystyryl)phenyl)acrylamide(13x)
(E)-N-(5-Methoxy-2-(3,4,5-trimethoxystyryl)phenyl)-3-(4-methoxy-3-nitrophenyl)acrylamide(13y)
(E)-3-(3-Amino-4-methoxyphenyl)-N-(5-methoxy-2-(3,4,5-trimethoxystyryl)phenyl)acrylamide(13z)
(E)-3-(3,4-Difluorophenyl)-N-(5-methoxy-2-(3,4,5-trimethoxystyryl)phenyl)acrylamide(13aa)
(E)-N-(5-Methoxy-2-(3,4,5-trimethoxystyryl)phenyl)-3-(3,4,5-trimethoxyphenyl)acrylamide(13ab)
(E)-3-(3,4-Dimethoxy-5-nitrophenyl)-N-(5-methoxy-2-(3,4,5-trimethoxystyryl)phenyl)acrylamide(13ac)
(E)-3-(3-Amino-4,5-dimethoxyphenyl)-N-(5-methoxy-2-(3,4,5-trimethoxystyryl)phenyl)acrylamide(13ad)
(E)-3-(1H-Indol-3-yl)-N-(5-methoxy-2-(3,4,5-trimethoxystyryl)phenyl)acrylamide(13ae)
(E)-N-(5-Methoxy-2-(3,4,5-trimethoxystyryl)phenyl)-3-(1-methyl-1H-indol-3-yl)acrylamide(13af)
N-(4-Methoxy-2-(3,4,5-trimethoxystyryl)phenyl)cinnamamide(14a)
(E)-N-(4-Methoxy-2-(3,4,5-trimethoxystyryl)phenyl)-3-(2-methoxyphenyl)acrylamide(14b)
(E)-3-(2-Hydroxyphenyl)-N-(4-methoxy-2-(3,4,5-trimethoxystyryl)phenyl)acrylamide(14c)
(E)-N-(4-Methoxy-2-(3,4,5-trimethoxystyryl)phenyl)-3-(2-nitrophenyl)acrylamide(14d)
(E)-3-(2-Aminophenyl)-N-(4-methoxy-2-(3,4,5-trimethoxystyryl)phenyl)acrylamide(14e)
(E)-N-(4-Methoxy-2-(3,4,5-trimethoxystyryl)phenyl)-3-(3-methoxyphenyl)acrylamide(14f)
(E)-3-(3-Hydroxyphenyl)-N-(4-methoxy-2-(3,4,5-trimethoxystyryl)phenyl)acrylamide(14g)
(E)-N-(4-Methoxy-2-(3,4,5-trimethoxystyryl)phenyl)-3-(3-(prop-2-ynyloxy)phenyl)acrylamide(14h)
(E)-3-(3-(Allyloxy)phenyl)-N-(4-methoxy-2-(3,4,5-trimethoxystyryl)phenyl)acrylamide(14i)
(E)-N-(4-Methoxy-2-(3,4,5-trimethoxystyryl)phenyl)-3-(3-nitrophenyl)acrylamide(14j)
(E)-3-(3-Aminophenyl)-N-(4-methoxy-2-(3,4,5-trimethoxystyryl)phenyl)acrylamide(14k)
(E)-N-(4-Methoxy-2-(3,4,5-trimethoxystyryl)phenyl)-3-(4-methoxyphenyl)acrylamide(14l)
(E)-3-(4-Hydroxyphenyl)-N-(4-methoxy-2-(3,4,5-trimethoxystyryl)phenyl)acrylamide(14m)
(E)-N-(4-Methoxy-2-(3,4,5-trimethoxystyryl)phenyl)-3-(4-(trifluoromethyl)phenyl)acrylamide(14n)
(E)-N-(4-Methoxy-2-(3,4,5-trimethoxystyryl)phenyl)-3-(4-nitrophenyl)acrylamide(14o)
(E)-3-(4-Aminophenyl)-N-(4-methoxy-2-(3,4,5-trimethoxystyryl)phenyl)acrylamide(14p)
(E)-3-(4-Chlorophenyl)-N-(4-methoxy-2-(3,4,5-trimethoxystyryl)phenyl)acrylamide(14q)
(E)-3-(4-Fluorophenyl)-N-(4-methoxy-2-(3,4,5-trimethoxystyryl)phenyl)acrylamide(14r)
(E)-3-(3,4-Dimethoxyphenyl)-N-(4-methoxy-2-(3,4,5-trimethoxystyryl)phenyl)acrylamide(14s)
(E)-3-(4-Hydroxy-3-methoxyphenyl)-N-(4-methoxy-2-(3,4,5-trimethoxystyryl)phenyl)acrylamide(14t)
(E)-N-(4-Methoxy-2-(3,4,5-trimethoxystyryl)phenyl)-3-(3-methoxy-4-nitrophenyl)acrylamide(14u)
(E)-3-(4-Amino-3-methoxyphenyl)-N-(4-methoxy-2-(3,4,5-trimethoxystyryl)phenyl)acrylamide(14v)
(E)-3-(3,4-Dihydroxyphenyl)-N-(4-methoxy-2-(3,4,5-trimethoxystyryl)phenyl)acrylamide(14w)
(E)-3-(3-Hydroxy-4-methoxyphenyl)-N-(4-methoxy-2-(3,4,5-trimethoxystyryl)phenyl)acrylamide(14x)
(E)-N-(4-Methoxy-2-(3,4,5-trimethoxystyryl)phenyl)-3-(4-methoxy-3-nitrophenyl)acrylamide(14y)
(E)-3-(3-Amino-4-methoxyphenyl)-N-(4-methoxy-2-(3,4,5-trimethoxystyryl)phenyl)acrylamide(14z)
(E)-3-(3,4-Difluorophenyl)-N-(4-methoxy-2-(3,4,5-trimethoxystyryl)phenyl)acrylamide(14aa)
(E)-N-(4-Methoxy-2-(3,4,5-trimethoxystyryl)phenyl)-3-(3,4,5-trimethoxyphenyl)acrylamide(14ab)
(E)-3-(3,4-Dimethoxy-5-nitrophenyl)-N-(4-methoxy-2-(3,4,5-trimethoxystyryl)phenyl)acrylamide(14ac)
(E)-3-(3-Amino-4,5-dimethoxyphenyl)-N-(4-methoxy-2-(3,4,5-trimethoxystyryl)phenyl)acrylamide(14ad)
(E)-3-(1H-Indol-3-yl)-N-(4-methoxy-2-(3,4,5-trimethoxystyryl)phenyl)acrylamide(14ae)
(E)-N-(4-Methoxy-2-(3,4,5-trimethoxystyryl)phenyl)-3-(1-methyl-1H-indol-3-yl)acrylamide(14f)
N-(2-Methoxy-5-(3,4,5-trimethoxystyryl)phenyl)cinnamamide(15a)
(E)-N-(2-Methoxy-5-(3,4,5-trimethoxystyryl)phenyl)-3-(2-methoxyphenyl)acrylamide(15b)
(E)-3-(2-Hydroxyphenyl)-N-(2-methoxy-5-(3,4,5-trimethoxystyryl)phenyl)acrylamide(15c)
(E)-N-(2-Methoxy-5-(3,4,5-trimethoxystyryl)phenyl)-3-(2-nitrophenyl)acrylamide(15d)
(E)-3-(2-Aminophenyl)-N-(2-methoxy-5-(3,4,5-trimethoxystyryl)phenyl)acrylamide(15e)
(E)-N-(2-Methoxy-5-(3,4,5-trimethoxystyryl)phenyl)-3-(3-methoxyphenyl)acrylamide(15f)
(E)-3-(3-Hydroxyphenyl)-N-(2-methoxy-5-(3,4,5-trimethoxystyryl)phenyl)acrylamide(15g)
(E)-N-(2-Methoxy-5-(3,4,5-trimethoxystyryl)phenyl)-3-(3-(prop-2-ynyloxy)phenyl)acrylamide(15h)
(E)-3-(3-(Allyloxy)phenyl)-N-(2-methoxy-5-(3,4,5-trimethoxystyryl)phenyl)acrylamide(15i)
(E)-N-(2-Methoxy-5-(3,4,5-trimethoxystyryl)phenyl)-3-(3-nitrophenyl)acrylamide(15j)
(E)-3-(3-Aminophenyl)-N-(2-methoxy-5-(3,4,5-trimethoxystyryl)phenyl)acrylamide(15k)
(E)-N-(2-Methoxy-5-(3,4,5-trimethoxystyryl)phenyl)-3-(4-methoxyphenyl)acrylamide(15l)
(E)-3-(4-Hydroxyphenyl)-N-(2-methoxy-5-(3,4,5-trimethoxystyryl)phenyl)acrylamide(15m)
(E)-N-(2-Methoxy-5-(3,4,5-trimethoxystyryl)phenyl)-3-(4-(trifluoromethyl)phenyl)acrylamide(15n)
(E)-N-(2-Methoxy-5-(3,4,5-trimethoxystyryl)phenyl)-3-(4-nitrophenyl)acrylamide(15o)
(E)-3-(4-Aminophenyl)-N-(2-methoxy-5-(3,4,5-trimethoxystyryl)phenyl)acrylamide(15p)
(E)-3-(4-Chlorophenyl)-N-(2-methoxy-5-(3,4,5-trimethoxystyryl)phenyl)acrylamide(15q)
(E)-3-(4-Fluorophenyl)-N-(2-methoxy-5-(3,4,5-trimethoxystyryl)phenyl)acrylamide(15r)
(E)-3-(3,4-Dimethoxyphenyl)-N-(2-methoxy-5-(3,4,5-trimethoxystyryl)phenyl)acrylamide(15s)
(E)-3-(4-Hydroxy-3-methoxyphenyl)-N-(2-methoxy-5-(3,4,5-trimethoxystyryl)phenyl)acrylamide(15t)
(E)-3-(3-Methoxy-4-nitrophenyl)-N-(2-methoxy-5-(3,4,5-trimethoxystyryl)phenyl)acrylamide(15u)
(E)-3-(4-Amino-3-methoxyphenyl)-N-(2-methoxy-5-(3,4,5-trimethoxystyryl)phenyl)acrylamide(15v)
(E)-3-(3,4-Dihydroxyphenyl)-N-(2-methoxy-5-(3,4,5-trimethoxystyryl)phenyl)acrylamide(15w)
(E)-3-(3-Hydroxy-4-methoxyphenyl)-N-(2-methoxy-5-(3,4,5-trimethoxystyryl)phenyl)acrylamide(15x)

(E)-3-(4-Methoxy-3-nitrophenyl)-N-(2-methoxy-5-(3,4,5-trimethoxystyryl)phenyl)acrylamide(15y)
(E)-3-(3-Amino-4-methoxyphenyl)-N-(2-methoxy-5-(3,4,5-trimethoxystyryl)phenyl)acrylamide(15z)
(E)-3-(3,4-Difluorophenyl)-N-(2-methoxy-5-(3,4,5-trimethoxystyryl)phenyl)acrylamide(15aa)
(E)-N-(2-Methoxy-5-(3,4,5-trimethoxystyryl)phenyl)-3-(3,4,5-trimethoxyphenyl)acrylamide(15ab)
(E)-3-(3,4-Dimethoxy-5-nitrophenyl)-N-(2-methoxy-5-(3,4,5-trimethoxystyryl)phenyl)acrylamide(15ac)
(E)-3-(3-Amino-4,5-dimethoxyphenyl)-N-(2-methoxy-5-(3,4,5-trimethoxystyryl)phenyl)acrylamide(15ad)
(E)-3-(1H-Indol-3-yl)-N-(2-methoxy-5-(3,4,5-trimethoxystyryl)phenyl)acrylamide(15ae)
(E)-N-(2-Methoxy-5-(3,4,5-trimethoxystyryl)phenyl)-3-(1-methyl-1H-indol-3-yl)acrylamide(15af)
N-(2-Hydroxy-5-(3,4,5-trimethoxystyryl)phenyl)cinnamamide(16a)
(E)-N-(2-Hydroxy-5-(3,4,5-trimethoxystyryl)phenyl)-3-(2-methoxyphenyl)acrylamide(16b)
(E)-N-(2-Hydroxy-5-(3,4,5-trimethoxystyryl)phenyl)-3-(2-hydroxyphenyl)acrylamide(16c)
(E)-N-(2-Hydroxy-5-(3,4,5-trimethoxystyryl)phenyl)-3-(2-nitrophenyl)acrylamide(16d)
(E)-3-(2-Aminophenyl)-N-(2-hydroxy-5-(3,4,5-trimethoxystyryl)phenyl)acrylamide(16e)
(E)-N-(2-Hydroxy-5-(3,4,5-trimethoxystyryl)phenyl)-3-(3-methoxyphenyl)acrylamide(16f)
(E)-N-(2-Hydroxy-5-(3,4,5-trimethoxystyryl)phenyl)-3-(3-hydroxyphenyl)acrylamide(16g)
(E)-N-(2-Hydroxy-5-(3,4,5-trimethoxystyryl)phenyl)-3-(3-(prop-2-ynyloxy)phenyl)acrylamide(16h)
(E)-3-(3-(Allyloxy)phenyl)-N-(2-hydroxy-5-(3,4,5-trimethoxystyryl)phenyl)acrylamide(16i)
(E)-N-(2-Hydroxy-5-(3,4,5-trimethoxystyryl)phenyl)-3-(3-nitrophenyl)acrylamide(16j)
(E)-3-(3-Aminophenyl)-N-(2-hydroxy-5-(3,4,5-trimethoxystyryl)phenyl)acrylamide(16k)
(E)-N-(2-Hydroxy-5-(3,4,5-trimethoxystyryl)phenyl)-3-(4-methoxyphenyl)acrylamide(16l)
(E)-N-(2-Hydroxy-5-(3,4,5-trimethoxystyryl)phenyl)-3-(4-hydroxyphenyl)acrylamide(16m)
(E)-N-(2-Hydroxy-5-(3,4,5-trimethoxystyryl)phenyl)-3-(4-(trifluoromethyl)phenyl)acrylamide(16n)
(E)-N-(2-Hydroxy-5-(3,4,5-trimethoxystyryl)phenyl)-3-(4-nitrophenyl)acrylamide(16o)
(E)-3-(4-Aminophenyl)-N-(2-hydroxy-5-(3,4,5-trimethoxystyryl)phenyl)acrylamide(16p)
(E)-3-(4-Chlorophenyl)-N-(2-hydroxy-5-(3,4,5-trimethoxystyryl)phenyl)acrylamide(16q)
(E)-3-(4-Fluorophenyl)-N-(2-hydroxy-5-(3,4,5-trimethoxystyryl)phenyl)acrylamide(16r)
(E)-3-(3,4-Dimethoxyphenyl)-N-(2-hydroxy-5-(3,4,5-trimethoxystyryl)phenyl)acrylamide(16s)
(E)-3-(4-Hydroxy-3-methoxyphenyl)-N-(2-hydroxy-5-(3,4,5-trimethoxystyryl)phenyl)acrylamide(16t)
(E)-N-(2-Hydroxy-5-(3,4,5-trimethoxystyryl)phenyl)-3-(3-methoxy-4-nitrophenyl)acrylamide(16u)
(E)-3-(4-Amino-3-methoxyphenyl)-N-(2-hydroxy-5-(3,4,5-trimethoxystyryl)phenyl)acrylamide(16v)
(E)-3-(3,4-Dihydroxyphenyl)-N-(2-hydroxy-5-(3,4,5-trimethoxystyryl)phenyl)acrylamide(16w)
(E)-3-(3-Hydroxy-4-methoxyphenyl)-N-(2-hydroxy-5-(3,4,5-trimethoxystyryl)phenyl)acrylamide(16x)
(E)-N-(2-Hydroxy-5-(3,4,5-trimethoxystyryl)phenyl)-3-(4-methoxy-3-nitrophenyl)acrylamide(16y)
(E)-3-(3-Amino-4-methoxyphenyl)-N-(2-hydroxy-5-(3,4,5-trimethoxystyryl)phenyl)acrylamide(16z)
(E)-3-(3,4-Difluorophenyl)-N-(2-hydroxy-5-(3,4,5-trimethoxystyryl)phenyl)acrylamide(16aa)
(E)-N-(2-Hydroxy-5-(3,4,5-trimethoxystyryl)phenyl)-3-(3,4,5-trimethoxyphenyl)acrylamide(16ab)
(E)-3-(3,4-Dimethoxy-5-nitrophenyl)-N-(2-hydroxy-5-(3,4,5-trimethoxystyryl)phenyl)acrylamide(16ac)
(E)-3-(3-Amino-4,5-dimethoxyphenyl)-N-(2-hydroxy-5-(3,4,5-trimethoxystyryl)phenyl)acrylamide(16ad)
(E)-N-(2-Hydroxy-5-(3,4,5-trimethoxystyryl)phenyl)-3-(1H-indol-3-yl)acrylamide(16ae)
(E)-N-(2-Hydroxy-5-(3,4,5-trimethoxystyryl)phenyl)-3-(1-methyl-1H-indol-3-yl)acrylamide(16af)
N-(2-Methoxy-4-(3,4,5-trimethoxystyryl)phenyl)cinnamamide(17a)
(E)-N-(2-Methoxy-4-(3,4,5-trimethoxystyryl)phenyl)-3-(2-methoxyphenyl)acrylamide(17b)
(E)-3-(2-Hydroxyphenyl)-N-(2-methoxy-4-(3,4,5-trimethoxystyryl)phenyl)acrylamide(17c)
(E)-N-(2-Methoxy-4-(3,4,5-trimethoxystyryl)phenyl)-3-(2-nitrophenyl)acrylamide(17d)
(E)-3-(2-Aminophenyl)-N-(2-methoxy-4-(3,4,5-trimethoxystyryl)phenyl)acrylamide(17e)
(E)-N-(2-Methoxy-4-(3,4,5-trimethoxystyryl)phenyl)-3-(3-methoxyphenyl)acrylamide(17f)
(E)-3-(3-Hydroxyphenyl)-N-(2-methoxy-4-(3,4,5-trimethoxystyryl)phenyl)acrylamide(17g)
(E)-N-(2-Methoxy-4-(3,4,5-trimethoxystyryl)phenyl)-3-(3-(prop-2-ynyloxy)phenyl)acrylamide(17h)
(E)-3-(3-(Allyloxy)phenyl)-N-(2-methoxy-4-(3,4,5-trimethoxystyryl)phenyl)acrylamide(17i)
(E)-N-(2-Methoxy-4-(3,4,5-trimethoxystyryl)phenyl)-3-(3-nitrophenyl)acrylamide(17j)
(E)-3-(3-Aminophenyl)-N-(2-methoxy-4-(3,4,5-trimethoxystyryl)phenyl)acrylamide(17k)
(E)-N-(2-Methoxy-4-(3,4,5-trimethoxystyryl)phenyl)-3-(4-methoxyphenyl)acrylamide(17l)
(E)-3-(4-Hydroxyphenyl)-N-(2-methoxy-4-(3,4,5-trimethoxystyryl)phenyl)acrylamide(17m)
(E)-N-(2-Methoxy-4-(3,4,5-trimethoxystyryl)phenyl)-3-(4-(trifluoromethyl)phenyl)acrylamide(17n)
(E)-N-(2-Methoxy-4-(3,4,5-trimethoxystyryl)phenyl)-3-(4-nitrophenyl)acrylamide(17o)
(E)-3-(4-Aminophenyl)-N-(2-methoxy-4-(3,4,5-trimethoxystyryl)phenyl)acrylamide(17p)
(E)-3-(4-Chlorophenyl)-N-(2-methoxy-4-(3,4,5-trimethoxystyryl)phenyl)acrylamide(17q)
(E)-3-(4-Fluorophenyl)-N-(2-methoxy-4-(3,4,5-trimethoxystyryl)phenyl)acrylamide(17r)
(E)-3-(3,4-Dimethoxyphenyl)-N-(2-methoxy-4-(3,4,5-trimethoxystyryl)phenyl)acrylamide(17s)
(E)-3-(4-Hydroxy-3-methoxyphenyl)-N-(2-methoxy-4-(3,4,5-trimethoxystyryl)phenyl)acrylamide(17t)
(E)-N-(2-Methoxy-4-(3,4,5-trimethoxystyryl)phenyl)-3-(3-methoxy-4-nitrophenyl)acrylamide(17u)
(E)-3-(4-Amino-3-methoxyphenyl)-N-(2-methoxy-4-(3,4,5-trimethoxystyryl)phenyl)acrylamide(17v)
(E)-3-(3,4-Dihydroxyphenyl)-N-(2-methoxy-4-(3,4,5-trimethoxystyryl)phenyl)acrylamide(17w)
(E)-3-(3-Hydroxy-4-methoxyphenyl)-N-(2-methoxy-4-(3,4,5-trimethoxystyryl)phenyl)acrylamide(17x)
(E)-3-(4-Methoxy-3-nitrophenyl)-N-(2-methoxy-4-(3,4,5-trimethoxystyryl)phenyl)acrylamide(17y)
(E)-3-(3-Amino-4-methoxyphenyl)-N-(2-methoxy-4-(3,4,5-trimethoxystyryl)phenyl)acrylamide(17z)

(E)-3-(3,4-Difluorophenyl)-N-(2-methoxy-4-(3,4,5-trimethoxystyryl)phenyl)acrylamide(17aa)
(E)-N-(2-Methoxy-4-(3,4,5-trimethoxystyryl)phenyl)-3-(3,4,5-trimethoxyphenyl)acrylamide(17ab)
(E)-3-(3,4-Dimethoxy-5-nitrophenyl)-N-(2-methoxy-4-(3,4,5-trimethoxystyryl)phenyl)acrylamide(17ac)
(E)-3-(3-Amino-4,5-dimethoxyphenyl)-N-(2-methoxy-4-(3,4,5-trimethoxystyryl)phenyl)acrylamide(17ad)
(E)-3-(1H-Indol-3-yl)-N-(2-methoxy-4-(3,4,5-trimethoxystyryl)phenyl)acrylamide(17ae)
(E)-N-(2-Methoxy-4-(3,4,5-trimethoxystyryl)phenyl)-3-(1-methyl-1H-indol-3-yl)acrylamide(17af)
N-(2-Hydroxy-4-(3,4,5-trimethoxystyryl)phenyl)cinnamamide(18a)
(E)-N-(2-Hydroxy-4-(3,4,5-trimethoxystyryl)phenyl)-3-(2-methoxyphenyl)acrylamide(18b)
(E)-N-(2-Hydroxy-4-(3,4,5-trimethoxystyryl)phenyl)-3-(2-hydroxyphenyl)acrylamide(18c)
(E)-N-(2-Hydroxy-4-(3,4,5-trimethoxystyryl)phenyl)-3-(2-nitrophenyl)acrylamide(18d)
(E)-3-(2-Aminophenyl)-N-(2-hydroxy-4-(3,4,5-trimethoxystyryl)phenyl)acrylamide(18e)
(E)-N-(2-Hydroxy-4-(3,4,5-trimethoxystyryl)phenyl)-3-(3-methoxyphenyl)acrylamide(18f)
(E)-N-(2-Hydroxy-4-(3,4,5-trimethoxystyryl)phenyl)-3-(3-hydroxyphenyl)acrylamide(18g)
(E)-N-(2-Hydroxy-4-(3,4,5-trimethoxystyryl)phenyl)-3-(3-(prop-2-ynyloxy)phenyl)acrylamide(18h)
(E)-3-(3-(Allyloxy)phenyl)-N-(2-hydroxy-4-(3,4,5-trimethoxystyryl)phenyl)acrylamide(18i)
(E)-N-(2-Hydroxy-4-(3,4,5-trimethoxystyryl)phenyl)-3-(3-nitrophenyl)acrylamide(18j)
(E)-3-(3-Aminophenyl)-N-(2-hydroxy-4-(3,4,5-trimethoxystyryl)phenyl)acrylamide(18k)
(E)-N-(2-Hydroxy-4-(3,4,5-trimethoxystyryl)phenyl)-3-(4-methoxyphenyl)acrylamide(18i)
(E)-N-(2-Hydroxy-4-(3,4,5-trimethoxystyryl)phenyl)-3-(4-hydroxyphenyl)acrylamide(18m)
(E)-N-(2-Hydroxy-4-(3,4,5-trimethoxystyryl)phenyl)-3-(4-(trifluoromethyl)phenyl)acrylamide(18n)
(E)-N-(2-Hydroxy-4-(3,4,5-trimethoxystyryl)phenyl)-3-(4-nitrophenyl)acrylamide(18o)
(E)-3-(4-Aminophenyl)-N-(2-hydroxy-4-(3,4,5-trimethoxystyryl)phenyl)acrylamide(18p)
(E)-3-(4-Chlorophenyl)-N-(2-hydroxy-4-(3,4,5-trimethoxystyryl)phenyl)acrylamide(18q)
(E)-3-(4-Fluorophenyl)-N-(2-hydroxy-4-(3,4,5-trimethoxystyryl)phenyl)acrylamide(18r)
(E)-3-(3,4-Dimethoxyphenyl)-N-(2-hydroxy-4-(3,4,5-trimethoxystyryl)phenyl)acrylamide(18s)
(E)-3-(4-Hydroxy-3-methoxyphenyl)-N-(2-hydroxy-4-(3,4,5-trimethoxystyryl)phenyl)acrylamide(18t)
(E)-N-(2-Hydroxy-4-(3,4,5-trimethoxystyryl)phenyl)-3-(3-methoxy-4-nitrophenyl)acrylamide(18u)
(E)-3-(4-Amino-3-methoxyphenyl)-N-(2-hydroxy-4-(3,4,5-trimethoxystyryl)phenyl)acrylamide(18v)
(E)-3-(3,4-Dihydroxyphenyl)-N-(2-hydroxy-4-(3,4,5-trimethoxystyryl)phenyl)acrylamide(18w)
(E)-N-(2-Hydroxy-4-(3,4,5-trimethoxystyryl)phenyl)-3-(3-hydroxy-4-methoxyphenyl)acrylamide(18x)
(E)-N-(2-Hydroxy-4-(3,4,5-trimethoxystyryl)phenyl)-3-(4-methoxy-3-nitrophenyl)acrylamide(18y)
(E)-3-(3-Amino-4-methoxyphenyl)-N-(2-hydroxy-4-(3,4,5-trimethoxystyryl)phenyl)acrylamide(18z)
(E)-3-(3,4-Difluorophenyl)-N-(2-hydroxy-4-(3,4,5-trimethoxystyryl)phenyl)acrylamide(18aa)
(E)-N-(2-Hydroxy-4-(3,4,5-trimethoxystyryl)phenyl)-3-(3,4,5-trimethoxyphenyl)acrylamide(18ab)
(E)-3-(3,4-Dimethoxy-5-nitrophenyl)-N-(2-hydroxy-4-(3,4,5-trimethoxystyryl)phenyl)acrylamide(18ac)
(E)-3-(3-Amino-4,5-dimethoxyphenyl)-N-(2-hydroxy-4-(3,4,5-trimethoxystyryl)phenyl)acrylamide(18ad)
(E)-N-(2-Hydroxy-4-(3,4,5-trimethoxystyryl)phenyl)-3-(1H-indol-3-yl)acrylamide(18ae)
(E)-N-(2-Hydroxy-4-(3,4,5-trimethoxystyryl)phenyl)-3-(1-methyl-1H-indol-3-yl)acrylamide(18af)
N-(2,3-Dimethoxy-6-(3,4,5-trimethoxystyryl)phenyl)cinnamamide(19a)
(E)-N-(2,3-Dimethoxy-6-(3,4,5-trimethoxystyryl)phenyl)-3-(2-methoxyphenyl)acrylamide(19b)
(E)-N-(2,3-Dimethoxy-6-(3,4,5-trimethoxystyryl)phenyl)-3-(2-hydroxyphenyl)acrylamide(19c)
(E)-N-(2,3-Dimethoxy-6-(3,4,5-trimethoxystyryl)phenyl)-3-(2-nitrophenyl)acrylamide(19d)
(E)-3-(2-Aminophenyl)-N-(2,3-dimethoxy-6-(3,4,5-trimethoxystyryl)phenyl)acrylamide(19e)
(E)-N-(2,3-Dimethoxy-6-(3,4,5-trimethoxystyryl)phenyl)-3-(3-methoxyphenyl)acrylamide(19f)
(E)-N-(2,3-Dimethoxy-6-(3,4,5-trimethoxystyryl)phenyl)-3-(3-hydroxyphenyl)acrylamide(19g)
(E)-N-(2,3-Dimethoxy-6-(3,4,5-trimethoxystyryl)phenyl)-3-(3-(prop-2-ynyloxy)phenyl)acrylamide(19h)
(E)-3-(3-(Allyloxy)phenyl)-N-(2,3-dimethoxy-6-(3,4,5-trimethoxystyryl)phenyl)acrylamide(19i)
(E)-N-(2,3-Dimethoxy-6-(3,4,5-trimethoxystyryl)phenyl)-3-(3-nitrophenyl)acrylamide(19j)
(E)-3-(3-Aminophenyl)-N-(2,3-dimethoxy-6-(3,4,5-trimethoxystyryl)phenyl)acrylamide(19k)
(E)-N-(2,3-Dimethoxy-6-(3,4,5-trimethoxystyryl)phenyl)-3-(4-methoxyphenyl)acrylamide(19i)
(E)-N-(2,3-Dimethoxy-6-(3,4,5-trimethoxystyryl)phenyl)-3-(4-hydroxyphenyl)acrylamide(19m)
(E)-N-(2,3-Dimethoxy-6-(3,4,5-trimethoxystyryl)phenyl)-3-(4-(trifluoromethyl)phenyl)acrylamide(19n)
(E)-N-(2,3-Dimethoxy-6-(3,4,5-trimethoxystyryl)phenyl)-3-(4-nitrophenyl)acrylamide(19o)
(E)-3-(4-Aminophenyl)-N-(2,3-dimethoxy-6-(3,4,5-trimethoxystyryl)phenyl)acrylamide(19p)
(E)-3-(4-Chlorophenyl)-N-(2,3-dimethoxy-6-(3,4,5-trimethoxystyryl)phenyl)acrylamide(19q)
(E)-N-(2,3-Dimethoxy-6-(3,4,5-trimethoxystyryl)phenyl)-3-(4-fluorophenyl)acrylamide(19r)
(E)-N-(2,3-Dimethoxy-6-(3,4,5-trimethoxystyryl)phenyl)-3-(3,4-dimethoxyphenyl)acrylamide(19s)
(E)-N-(2,3-Dimethoxy-6-(3,4,5-trimethoxystyryl)phenyl)-3-(4-hydroxy-3-methoxyphenyl)acrylamide(19t)
(E)-N-(2,3-Dimethoxy-6-(3,4,5-trimethoxystyryl)phenyl)-3-(3-methoxy-4-nitrophenyl)acrylamide(19u)
(E)-3-(4-Amino-3-methoxyphenyl)-N-(2,3-dimethoxy-6-(3,4,5-trimethoxystyryl)phenyl)acrylamide(19v)
(E)-3-(3,4-Dihydroxyphenyl)-N-(2,3-dimethoxy-6-(3,4,5-trimethoxystyryl)phenyl)acrylamide(19w)
(E)-N-(2,3-Dimethoxy-6-(3,4,5-trimethoxystyryl)phenyl)-3-(3-hydroxy-4-methoxyphenyl)acrylamide(19x)
(E)-N-(2,3-Dimethoxy-6-(3,4,5-trimethoxystyryl)phenyl)-3-(4-methoxy-3-nitrophenyl)acrylamide(19y)
(E)-3-(3-Amino-4-methoxyphenyl)-N-(2,3-dimethoxy-6-(3,4,5-trimethoxystyryl)phenyl)acrylamide(19z)
(E)-3-(3,4-Difluorophenyl)-N-(2,3-dimethoxy-6-(3,4,5-trimethoxystyryl)phenyl)acrylamide(19aa)
(E)-N-(2,3-Dimethoxy-6-(3,4,5-trimethoxystyryl)phenyl)-3-(3,4,5-trimethoxyphenyl)acrylamide(19ab)

(E)-3-(3,4-Dimethoxy-5-nitrophenyl)-N-(2,3-dimethoxy-6-(3,4,5-trimethoxystyryl)phenyl)acrylamide(19ac)
(E)-3-(3-Amino-4,5-dimethoxyphenyl)-N-(2,3-dimethoxy-6-(3,4,5-trimethoxystyryl)phenyl)acrylamide(19ad)
(E)-N-(2,3-Dimethoxy-6-(3,4,5-trimethoxystyryl)phenyl)-3-(1H-indol-3-yl)acrylamide(19ae)
(E)-N-(2,3-Dimethoxy-6-(3,4,5-trimethoxystyryl)phenyl)-3-(1-methyl-1H-indol-3-yl)acrylamide(19af)
N-(2-Hydroxy-3-methoxy-6-(3,4,5-trimethoxystyryl)phenyl)cinnamamide(20a)
(E)-N-(2-Hydroxy-3-methoxy-6-(3,4,5-trimethoxystyryl)phenyl)-3-(2-methoxyphenyl)acrylamide(20b)
(E)-N-(2-hydroxy-3-methoxy-6-(3,4,5-trimethoxystyryl)phenyl)-3-(2-hydroxyphenyl)acrylamide(20c)
(E)-N-(2-Hydroxy-3-methoxy-6-(3,4,5-trimethoxystyryl)phenyl)-3-(2-nitrophenyl)acrylamide(20d)
(E)-3-(2-Aminophenyl)-N-(2-hydroxy-3-methoxy-6-(3,4,5-trimethoxystyryl)phenyl)acrylamide(20e)
(E)-N-(2-Hydroxy-3-methoxy-6-(3,4,5-trimethoxystyryl)phenyl)-3-(3-methoxyphenyl)acrylamide(20f)
(E)-N-(2-Hydroxy-3-methoxy-6-(3,4,5-trimethoxystyryl)phenyl)-3-(3-hydroxyphenyl)acrylamide(20g)
(E)-N-(2-Hydroxy-3-methoxy-6-(3,4,5-trimethoxystyryl)phenyl)-3-(3-(prop-2-ynyloxy)phenyl)acrylamide(20h)
(E)-3-(3-(Allyloxy)phenyl)-N-(2-hydroxy-3-methoxy-6-(3,4,5-trimethoxystyryl)phenyl)acrylamide(20i)
(E)-N-(2-Hydroxy-3-methoxy-6-(3,4,5-trimethoxystyryl)phenyl)-3-(3-nitrophenyl)acrylamide(20j)
(E)-3-(3-Aminophenyl)-N-(2-hydroxy-3-methoxy-6-(3,4,5-trimethoxystyryl)phenyl)acrylamide(20k)
(E)-N-(2-Hydroxy-3-methoxy-6-(3,4,5-trimethoxystyryl)phenyl)-3-(4-methoxyphenyl)acrylamide(20)
(E)-N-(2-Hydroxy-3-methoxy-6-(3,4,5-trimethoxystyryl)phenyl)-3-(4-hydroxyphenyl)acrylamide(20m)
(E)-N-(2-Hydroxy-3-methoxy-6-(3,4,5-trimethoxystyryl)phenyl)-3-(4-(trifluoromethyl)phenyl)acrylamide(20n)
(E)-N-(2-Hydroxy-3-methoxy-6-(3,4,5-trimethoxystyryl)phenyl)-3-(4-nitrophenyl)acrylamide(20o)
(E)-3-(4-Aminophenyl)-N-(2-hydroxy-3-methoxy-6-(3,4,5-trimethoxystyryl)phenyl)acrylamide(20p)
(E)-3-(4-Chlorophenyl)-N-(2-hydroxy-3-methoxy-6-(3,4,5-trimethoxystyryl)phenyl)acrylamide(20q)
(E)-3-(4-Fluorophenyl)-N-(2-hydroxy-3-methoxy-6-(3,4,5-trimethoxystyryl)phenyl)acrylamide(20r)
(E)-3-(3,4-Dimethoxyphenyl)-N-(2-hydroxy-3-methoxy-6-(3,4,5-trimethoxystyryl)phenyl)acrylamide(20s)
(E)-N-(2-Hydroxy-3-methoxy-6-(3,4,5-trimethoxystyryl)phenyl)-3-(4-hydroxy-3-methoxyphenyl)acrylamide(20t)
(E)-N-(2-Hydroxy-3-methoxy-6-(3,4,5-trimethoxystyryl)phenyl)-3-(3-methoxy-4-nitrophenyl)acrylamide(20u)
(E)-3-(4-Amino-3-methoxyphenyl)-N-(2-hydroxy-3-methoxy-6-(3,4,5-trimethoxystyryl)phenyl)acrylamide(20v)
(E)-3-(3,4-Dihydroxyphenyl)-N-(2-hydroxy-3-methoxy-6-(3,4,5-trimethoxystyryl)phenyl)acrylamide(20w)
(E)-N-(2-Hydroxy-3-methoxy-6-(3,4,5-trimethoxystyryl)phenyl)-3-(3-hydroxy-4-methoxyphenyl)acrylamide(20x)
(E)-N-(2-Hydroxy-3-methoxy-6-(3,4,5-trimethoxystyryl)phenyl)-3-(4-methoxy-3-nitrophenyl)acrylamide(20y)
(E)-3-(3-Amino-4-methoxyphenyl)-N-(2-hydroxy-3-methoxy-6-(3,4,5-trimethoxystyryl)phenyl)acrylamide(20z)
(E)-3-(3,4-Difluorophenyl)-N-(2-hydroxy-3-methoxy-6-(3,4,5-trimethoxystyryl)phenyl)acrylamide(20aa)
(E)-N-(2-Hydroxy-3-methoxy-6-(3,4,5-trimethoxystyryl)phenyl)-3-(3,4,5-trimethoxyphenyl)acrylamide(20ab)
(E)-3-(3,4-Dimethoxy-5-nitrophenyl)-N-(2-hydroxy-3-methoxy-6-(3,4,5-trimethoxystyryl)phenyl)acrylamide (20ac)
(E)-3-(3-Amino-4,5-dimethoxyphenyl)-N-(2-hydroxy-3-methoxy-6-(3,4,5-trimethoxystyryl)phenyl)acrylamide (20ad)
(E)-N-(2-Hydroxy-3-methoxy-6-(3,4,5-trimethoxystyryl)phenyl)-3-(1H-indol-3-yl)acrylamide(20ae)
(E)-N-(2-Hydroxy-3-methoxy-6-(3,4,5-trimethoxystyryl)phenyl)-3-(1-methyl-1H-indol-3-yl)acrylamide(20af)
N-(3-Hydroxy-2-methoxy-6-(3,4,5-trimethoxystyryl)phenyl)cinnamamide(21a)
(E)-N-(3-Hydroxy-2-methoxy-6-(3,4,5-trimethoxystyryl)phenyl)-3-(2-methoxyphenyl)acrylamide(21b)
(E)-N-(3-Hydroxy-2-methoxy-6-(3,4,5-trimethoxystyryl)phenyl)-3-(2-hydroxyphenyl)acrylamide(21c)
(E)-N-(3-Hydroxy-2-methoxy-6-(3,4,5-trimethoxystyryl)phenyl)-3-(2-nitrophenyl)acrylamide(21d)
(E)-3-(2-Aminophenyl)-N-(3-hydroxy-2-methoxy-6-(3,4,5-trimethoxystyryl)phenyl)acrylamide(21e)
(E)-N-(3-Hydroxy-2-methoxy-6-(3,4,5-trimethoxystyryl)phenyl)-3-(3-methoxyphenyl)acrylamide(21f)
(E)-N-(3-Hydroxy-2-methoxy-6-(3,4,5-trimethoxystyryl)phenyl)-3-(3-hydroxyphenyl)acrylamide(21g)
(E)-N-(3-Hydroxy-2-methoxy-6-(3,4,5-trimethoxystyryl)phenyl)-3-(3-(prop-2-ynyloxy)phenyl)acrylamide(21h)
(E)-3-(3-(Allyloxy)phenyl)-N-(3-hydroxy-2-methoxy-6-(3,4,5-trimethoxystyryl)phenyl)acrylamide(21i)
(E)-N-(3-Hydroxy-2-methoxy-6-(3,4,5-trimethoxystyryl)phenyl)-3-(3-nitrophenyl)acrylamide(21j)
(E)-3-(3-Aminophenyl)-N-(3-hydroxy-2-methoxy-6-(3,4,5-trimethoxystyryl)phenyl)acrylamide(21k)
(E)-N-(3-Hydroxy-2-methoxy-6-(3,4,5-trimethoxystyryl)phenyl)-3-(4-methoxyphenyl)acrylamide(21l)
(E)-N-(3-Hydroxy-2-methoxy-6-(3,4,5-trimethoxystyryl)phenyl)-3-(4-hydroxyphenyl)acrylamide(21m)
(E)-N-(3-Hydroxy-2-methoxy-6-(3,4,5-trimethoxystyryl)phenyl)-3-(4-(trifluoromethyl)phenyl)acrylamide(21n)
(E)-N-(3-Hydroxy-2-methoxy-6-(3,4,5-trimethoxystyryl)phenyl)-3-(4-nitrophenyl)acrylamide(21o)
(E)-3-(4-Aminophenyl)-N-(3-hydroxy-2-methoxy-6-(3,4,5-trimethoxystyryl)phenyl)acrylamide(21p)
(E)-3-(4-Chlorophenyl)-N-(3-hydroxy-2-methoxy-6-(3,4,5-trimethoxystyryl)phenyl)acrylamide(21q)
(E)-3-(4-Fluorophenyl)-N-(3-hydroxy-2-methoxy-6-(3,4,5-trimethoxystyryl)phenyl)acrylamide(21r)
(E)-3-(3,4-Dimethoxyphenyl)-N-(3-hydroxy-2-methoxy-6-(3,4,5-trimethoxystyryl)phenyl)acrylamide(21s)
(E)-N-(3-Hydroxy-2-methoxy-6-(3,4,5-trimethoxystyryl)phenyl)-3-(4-hydroxy-3-methoxyphenyl)acrylamide(21t)
(E)-N-(3-Hydroxy-2-methoxy-6-(3,4,5-trimethoxystyryl)phenyl)-3-(3-methoxy-4-nitrophenyl)acrylamide(21u)
(E)-3-(4-Amino-3-methoxyphenyl)-N-(3-hydroxy-2-methoxy-6-(3,4,5-trimethoxystyryl)phenyl)acrylamide (21v)
(E)-3-(3,4-Dihydroxyphenyl)-N-(3-hydroxy-2-methoxy-6-(3,4,5-trimethoxystyryl)phenyl)acrylamide(21w)
(E)-N-(3-Hydroxy-2-methoxy-6-(3,4,5-trimethoxystyryl)phenyl)-3-(3-hydroxy-4-methoxyphenyl)acrylamide (21x)
(E)-N-(3-Hydroxy-2-methoxy-6-(3,4,5-trimethoxystyryl)phenyl)-3-(4-methoxy-3-nitrophenyl)acrylamide(21y)
(E)-3-(3-Amino-4-methoxyphenyl)-N-(3-hydroxy-2-methoxy-6-(3,4,5-trimethoxystyryl)phenyl)acrylamide (21z)
(E)-3-(3,4-Difluorophenyl)-N-(3-hydroxy-2-methoxy-6-(3,4,5-trimethoxystyryl)phenyl)acrylamide(21aa)

(E)-N-(3-Hydroxy-2-methoxy-6-(3,4,5-trimethoxystyryl)phenyl)-3-(3,4,5-trimethoxyphenyl)acrylamide(21ab)
(E)-3-(3,4-Dimethoxy-5-nitrophenyl)-N-(3-hydroxy-2-methoxy-6-(3,4,5-trimethoxystyryl)phenyl)acrylamide(21ac)
(E)-3-(3-Amino-4,5-dimethoxyphenyl)-N-(3-hydroxy-2-methoxy-6-(3,4,5-trimethoxystyryl)phenyl)acrylamide(21ad)
(E)-N-(3-Hydroxy-2-methoxy-6-(3,4,5-trimethoxystyryl)phenyl)-3-(1H-indol-3-yl)acrylamide(21ae)
(E)-N-(3-Hydroxy-2-methoxy-6-(3,4,5-trimethoxystyryl)phenyl)-3-(1-methyl-1H-indol-3-yl)acrylamide(21af)
N-(2,3-Dimethoxy-5-(3,4,5-trimethoxystyryl)phenyl)cinnamamide(22a)
(E)-N-(2,3-Dimethoxy-5-(3,4,5-trimethoxystyryl)phenyl)-3-(2-methoxyphenyl)acrylamide(22b)
(E)-N-(2,3-Dimethoxy-5-(3,4,5-trimethoxystyryl)phenyl)-3-(2-hydroxyphenyl)acrylamide(22c)
(E)-N-(2,3-Dimethoxy-5-(3,4,5-trimethoxystyryl)phenyl)-3-(2-nitrophenyl)acrylamide(22d)
(E)-3-(2-Aminophenyl)-N-(2,3-dimethoxy-5-(3,4,5-trimethoxystyryl)phenyl)acrylamide(22e)
(E)-N-(2,3-Dimethoxy-5-(3,4,5-trimethoxystyryl)phenyl)-3-(3-methoxyphenyl)acrylamide(22f)
(E)-N-(2,3-Dimethoxy-5-(3,4,5-trimethoxystyryl)phenyl)-3-(3-hydroxyphenyl)acrylamide(22g)
(E)-N-(2,3-Dimethoxy-5-(3,4,5-trimethoxystyryl)phenyl)-3-(3-(prop-2-ynyloxy)phenyl)acrylamide(22h)
(E)-3-(3-(Allyloxy)phenyl)-N-(2,3-dimethoxy-5-(3,4,5-trimethoxystyryl)phenyl)acrylamide(22i)
(E)-N-(2,3-Dimethoxy-5-(3,4,5-trimethoxystyryl)phenyl)-3-(3-nitrophenyl)acrylamide(22j)
(E)-3-(3-Aminophenyl)-N-(2,3-dimethoxy-5-(3,4,5-trimethoxystyryl)phenyl)acrylamide(22k)
(E)-N-(2,3-Dimethoxy-5-(3,4,5-trimethoxystyryl)phenyl)-3-(4-methoxyphenyl)acrylamide(22l)
(E)-N-(2,3-Dimethoxy-5-(3,4,5-trimethoxystyryl)phenyl)-3-(4-hydroxyphenyl)acrylamide(22m)
(E)-N-(2,3-Dimethoxy-5-(3,4,5-trimethoxystyryl)phenyl)-3-(4-(trifluoromethyl)phenyl)acrylamide(22n)
(E)-N-(2,3-Dimethoxy-5-(3,4,5-trimethoxystyryl)phenyl)-3-(4-nitrophenyl)acrylamide(22o)
(E)-3-(4-Aminophenyl)-N-(2,3-dimethoxy-5-(3,4,5-trimethoxystyryl)phenyl)acrylamide(22p)
(E)-3-(4-Chlorophenyl)-N-(2,3-dimethoxy-5-(3,4,5-trimethoxystyryl)phenyl)acrylamide(22q)
(E)-N-(2,3-Dimethoxy-5-(3,4,5-trimethoxystyryl)phenyl)-3-(4-fluorophenyl)acrylamide(22r)
(E)-N-(2,3-Dimethoxy-5-(3,4,5-trimethoxystyryl)phenyl)-3-(3,4-dimethoxyphenyl)acrylamide(22s)
(E)-N-(2,3-Dimethoxy-5-(3,4,5-trimethoxystyryl)phenyl)-3-(4-hydroxy-3-methoxyphenyl)acrylamide(22t)
(E)-N-(2,3-Dimethoxy-5-(3,4,5-trimethoxystyryl)phenyl)-3-(3-methoxy-4-nitrophenyl)acrylamide(22u)
(E)-3-(4-Amino-3-methoxyphenyl)-N-(2,3-dimethoxy-5-(3,4,5-trimethoxystyryl)phenyl)acrylamide(22v)
(E)-3-(3,4-Dihydroxyphenyl)-N-(2,3-dimethoxy-5-(3,4,5-trimethoxystyryl)phenyl)acrylamide(22w)
(E)-N-(2,3-Dimethoxy-5-(3,4,5-trimethoxystyryl)phenyl)-3-(3-hydroxy-4-methoxyphenyl)acrylamide(22x)
(E)-N-(2,3-Dimethoxy-5-(3,4,5-trimethoxystyryl)phenyl)-3-(4-methoxy-3-nitrophenyl)acrylamide(22y)
(E)-3-(3-Amino-4-methoxyphenyl)-N-(2,3-dimethoxy-5-(3,4,5-trimethoxystyryl)phenyl)acrylamide(22z)
(E)-3-(3,4-Difluorophenyl)-N-(2,3-dimethoxy-5-(3,4,5-trimethoxystyryl)phenyl)acrylamide(22aa)
(E)-N-(2,3-Dimethoxy-5-(3,4,5-trimethoxystyryl)phenyl)-3-(3,4,5-trimethoxyphenyl)acrylamide(22ab)
(E)-N-(2,3-Dimethoxy-5-(3,4,5-trimethoxystyryl)phenyl)-3-(3,4-dimethoxy-5-nitrophenyl)acrylamide(22ac)
(E)-3-(3-Amino-4,5-dimethoxyphenyl)-N-(2,3-dimethoxy-5-(3,4,5-trimethoxystyryl)phenyl)acrylamide(22ad)
(E)-N-(2,3-Dimethoxy-5-(3,4,5-trimethoxystyryl)phenyl)-3-(1H-indol-3-yl)acrylamide(22ae)
(E)-N-(2,3-Dimethoxy-5-(3,4,5-trimethoxystyryl)phenyl)-3-(1-methyl-1H-indol-3-yl)acrylamide(22af)
N-(3-Hydroxy-2-methoxy-5-(3,4,5-trimethoxystyryl)phenyl)cinnamamide(23a)
(E)-N-(3-Hydroxy-2-methoxy-5-(3,4,5-trimethoxystyryl)phenyl)-3-(2-methoxyphenyl)acrylamide(23b)
(E)-N-(3-Hydroxy-2-methoxy-5-(3,4,5-trimethoxystyryl)phenyl)-3-(2-hydroxyphenyl)acrylamide(23c)
(E)-N-(3-Hydroxy-2-methoxy-5-(3,4,5-trimethoxystyryl)phenyl)-3-(2-nitrophenyl)acrylamide(23d)
(E)-3-(2-Aminophenyl)-N-(3-hydroxy-2-methoxy-5-(3,4,5-trimethoxystyryl)phenyl)acrylamide(23e)
(E)-N-(3-Hydroxy-2-methoxy-5-(3,4,5-trimethoxystyryl)phenyl)-3-(3-methoxyphenyl)acrylamide(23f)
(E)-N-(3-Hydroxy-2-methoxy-5-(3,4,5-trimethoxystyryl)phenyl)-3-(3-hydroxyphenyl)acrylamide(23g)
(E)-N-(3-Hydroxy-2-methoxy-5-(3,4,5-trimethoxystyryl)phenyl)-3-(3-(prop-2-ynyloxy)phenyl)acrylamide(23h)
(E)-3-(3-(Allyloxy)phenyl)-N-(3-hydroxy-2-methoxy-5-(3,4,5-trimethoxystyryl)phenyl)acrylamide(23i)
(E)-N-(3-Hydroxy-2-methoxy-5-(3,4,5-trimethoxystyryl)phenyl)-3-(3-nitrophenyl)acrylamide(23j)
(E)-3-(3-Aminophenyl)-N-(3-hydroxy-2-methoxy-5-(3,4,5-trimethoxystyryl)phenyl)acrylamide(23k)
(E)-N-(3-Hydroxy-2-methoxy-5-(3,4,5-trimethoxystyryl)phenyl)-3-(4-methoxyphenyl)acrylamide(23l)
(E)-N-(3-Hydroxy-2-methoxy-5-(3,4,5-trimethoxystyryl)phenyl)-3-(4-hydroxyphenyl)acrylamide(23m)
(E)-N-(3-Hydroxy-2-methoxy-5-(3,4,5-trimethoxystyryl)phenyl)-3-(4-(trifluoromethyl)phenyl)acrylamide(23n)
(E)-N-(3-Hydroxy-2-methoxy-5-(3,4,5-trimethoxystyryl)phenyl)-3-(4-nitrophenyl)acrylamide(23o)
(E)-3-(4-Aminophenyl)-N-(3-hydroxy-2-methoxy-5-(3,4,5-trimethoxystyryl)phenyl)acrylamide(23p)
(E)-3-(4-Chlorophenyl)-N-(3-hydroxy-2-methoxy-5-(3,4,5-trimethoxystyryl)phenyl)acrylamide(23q)
(E)-3-(4-Fluorophenyl)-N-(3-hydroxy-2-methoxy-5-(3,4,5-trimethoxystyryl)phenyl)acrylamide(23r)
(E)-3-(3,4-Dimethoxyphenyl)-N-(3-hydroxy-2-methoxy-5-(3,4,5-trimethoxystyryl)phenyl)acrylamide(23s)
(E)-N-(3-Hydroxy-2-methoxy-5-(3,4,5-trimethoxystyryl)phenyl)-3-(4-hydroxy-3-methoxyphenyl)acrylamide(23t)
(E)-N-(3-Hydroxy-2-methoxy-5-(3,4,5-trimethoxystyryl)phenyl)-3-(3-methoxy-4-nitrophenyl)acrylamide(23u)
(E)-3-(4-Amino-3-methoxyphenyl)-N-(3-hydroxy-2-methoxy-5-(3,4,5-trimethoxystyryl)phenyl)acrylamide(23v)
(E)-3-(3,4-Dihydroxyphenyl)-N-(3-hydroxy-2-methoxy-5-(3,4,5-trimethoxystyryl)phenyl)acrylamide(23w)
(E)-N-(3-Hydroxy-2-methoxy-5-(3,4,5-trimethoxystyryl)phenyl)-3-(3-hydroxy-4-methoxyphenyl)acrylamide(23x)
(E)-N-(3-Hydroxy-2-methoxy-5-(3,4,5-trimethoxystyryl)phenyl)-3-(4-methoxy-3-nitrophenyl)acrylamide(23y)
(E)-3-(3-Amino-4-methoxyphenyl)-N-(3-hydroxy-2-methoxy-5-(3,4,5-trimethoxystyryl)phenyl)acrylamide(23z)
(E)-3-(3,4-Difluorophenyl)-N-(3-hydroxy-2-methoxy-5-(3,4,5-trimethoxystyryl)phenyl)acrylamide(23aa)

(E)-N-(3-Hydroxy-2-methoxy-5-(3,4,5-trimethoxystyryl)
    phenyl)-3-(3,4,5-trimethoxyphenyl)acrylamide(23ab)
(E)-3-(3,4-Dimethoxy-5-nitrophenyl)-N-(3-hydroxy-2-
    methoxy-5-(3,4,5-trimethoxystyryl)phenyl)acrylamide
    (23ac)
(E)-3-(3-Amino-4,5-dimethoxyphenyl)-N-(3-hydroxy-2-
    methoxy-5-(3,4,5-trimethoxystyryl)phenyl)acrylamide
    (23ad)
(E)-N-(3-Hydroxy-2-methoxy-5-(3,4,5-trimethoxystyryl)
    phenyl)-3-(1H-indol-3-yl)acrylamide(23ae)
(E)-N-(3-Hydroxy-2-methoxy-5-(3,4,5-trimethoxystyryl)
    phenyl)-3-(1-methyl-1H-indol-3-yl)acrylamide(23af)
N-(2-Hydroxy-3-methoxy-5-(3,4,5-trimethoxystyryl)phe-
    nyl)cinnamamide(24a)
(E)-N-(2-Hydroxy-3-methoxy-5-(3,4,5-trimethoxystyryl)
    phenyl)-3-(2-methoxyphenyl)acrylamide(24b)
(E)-N-(2-Hydroxy-3-methoxy-5-(3,4,5-trimethoxystyryl)
    phenyl)-3-(2-hydroxyphenyl)acrylamide(24c)
(E)-N-(2-Hydroxy-3-methoxy-5-(3,4,5-trimethoxystyryl)
    phenyl)-3-(2-nitrophenyl)acrylamide(24d)
(E)-3-(2-Aminophenyl)-N-(2-hydroxy-3-methoxy-5-(3,4,5-
    trimethoxystyryl)phenyl)acrylamide(24e)
(E)-N-(2-Hydroxy-3-methoxy-5-(3,4,5-trimethoxystyryl)
    phenyl)-3-(3-methoxyphenyl)acrylamide(24f)
(E)-N-(2-Hydroxy-3-methoxy-5-(3,4,5-trimethoxystyryl)
    phenyl)-3-(3-hydroxyphenyl)acrylamide(24g)
(E)-N-(2-Hydroxy-3-methoxy-5-(3,4,5-trimethoxystyryl)
    phenyl)-3-(3-(prop-2-ynyloxy)phenyl)acrylamide(24h)
(E)-3-(3-(Allyloxy)phenyl)-N-(2-hydroxy-3-methoxy-5-(3,
    4,5-trimethoxystyryl)phenyl)acrylamide(24i)
(E)-N-(2-Hydroxy-3-methoxy-5-(3,4,5-trimethoxystyryl)
    phenyl)-3-(3-nitrophenyl)acrylamide(24j)
(E)-3-(3-Aminophenyl)-N-(2-hydroxy-3-methoxy-5-(3,4,5-
    trimethoxystyryl)phenyl)acrylamide(24k)
(E)-N-(2-Hydroxy-3-methoxy-5-(3,4,5-trimethoxystyryl)
    phenyl)-3-(4-methoxyphenyl)acrylamide(24l)
(E)-N-(2-Hydroxy-3-methoxy-5-(3,4,5-trimethoxystyryl)
    phenyl)-3-(4-hydroxyphenyl)acrylamide(24m)
(E)-N-(2-Hydroxy-3-methoxy-5-(3,4,5-trimethoxystyryl)
    phenyl)-3-(4-(trifluoromethyl)phenyl)acrylamide(24n)
(E)-N-(2-Hydroxy-3-methoxy-5-(3,4,5-trimethoxystyryl)
    phenyl)-3-(4-nitrophenyl)acrylamide(24o)
(E)-3-(4-Aminophenyl)-N-(2-hydroxy-3-methoxy-5-(3,4,5-
    trimethoxystyryl)phenyl)acrylamide(24p)
(E)-3-(4-Chlorophenyl)-N-(2-hydroxy-3-methoxy-5-(3,4,5-
    trimethoxystyryl)phenyl)acrylamide(24q)
(E)-3-(4-Fluorophenyl)-N-(2-hydroxy-3-methoxy-5-(3,4,5-
    trimethoxystyryl)phenyl)acrylamide(24r)
(E)-3-(3,4-Dimethoxyphenyl)-N-(2-hydroxy-3-methoxy-5-
    (3,4,5-trimethoxystyryl)phenyl)acrylamide(24s)
(E)-N-(2-Hydroxy-3-methoxy-5-(3,4,5-trimethoxystyryl)
    phenyl)-3-(4-hydroxy-3-methoxyphenyl)acrylamide(24t)
(E)-N-(2-Hydroxy-3-methoxy-5-(3,4,5-trimethoxystyryl)
    phenyl)-3-(3-methoxy-4-nitrophenyl)acrylamide(24u)
(E)-3-(4-Amino-3-methoxyphenyl)-N-(2-hydroxy-3-
    methoxy-5-(3,4,5-trimethoxystyryl)phenyl)acrylamide
    (24v)
(E)-3-(3,4-Dihydroxyphenyl)-N-(2-hydroxy-3-methoxy-5-
    (3,4,5-trimethoxystyryl)phenyl)acrylamide(24w)
(E)-N-(2-Hydroxy-3-methoxy-5-(3,4,5-trimethoxystyryl)
    phenyl)-3-(3-hydroxy-4-methoxyphenyl)acrylamide
    (24x)
(E)-N-(2-Hydroxy-3-methoxy-5-(3,4,5-trimethoxystyryl)
    phenyl)-3-(4-methoxy-3-nitrophenyl)acrylamide(24y)
(E)-3-(3-Amino-4-methoxyphenyl)-N-(2-hydroxy-3-
    methoxy-5-(3,4,5-trimethoxystyryl)phenyl)acrylamide
    (24z)
(E)-3-(3,4-Difluorophenyl)-N-(2-hydroxy-3-methoxy-5-(3,
    4,5-trimethoxystyryl)phenyl)acrylamide(24aa)
(E)-N-(2-Hydroxy-3-methoxy-5-(3,4,5-trimethoxystyryl)
    phenyl)-3-(3,4,5-trimethoxyphenyl)acrylamide(24ab)
(E)-3-(3,4-Dimethoxy-5-nitrophenyl)-N-(2-hydroxy-3-
    methoxy-5-(3,4,5-trimethoxystyryl)phenyl)acrylamide
    (24ac)
(E)-3-(3-Amino-4,5-dimethoxyphenyl)-N-(2-hydroxy-3-
    methoxy-5-(3,4,5-trimethoxystyryl)phenyl)acrylamide
    (24ad)
(E)-N-(2-Hydroxy-3-methoxy-5-(3,4,5-trimethoxystyryl)
    phenyl)-3-(1H-indol-3-yl)acrylamide(24ae)
(E)-N-(2-Hydroxy-3-methoxy-5-(3,4,5-trimethoxystyryl)
    phenyl)-3-(1-methyl-1H-indol-3-yl)acrylamide(24af)

In another embodiment of the invention wherein the compounds are useful as anticancer agents in the treatment of conditions characterized by abnormal proliferation of the vasculature.

In one more embodiment of the invention wherein the invention provides a process for preparation of N-((3,4,5-trimethoxystyryl)aryl)cinnamamide compounds of general formulae A wherein the said process comprising the step of;

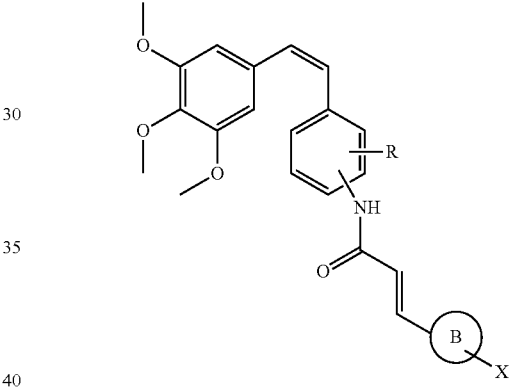

where in

B selected from aryl, heteroaryl and fused heteroaryl ring

R and X selected from H, hydroxy, alkyl, alkoxy, prop-2-ynyloxy, allyloxy, halo, alkylhalides, alkoxy halides, nitro, amine reacting amino compounds of formula 5a-q (1.0 mmol) with acid chloride compound of formula 7a-z (1.0 mmol) in the presence of triethylamine (3-5 mmol) in dry tetrahydrofuran at about 0° C. and stirred for 12-18 h at room temperature, diluting the reaction mixture with ethyl acetate and washed with water and brine solution, followed by chromatographic purification to obtain respective N-((3,4,5-trimethoxystyryl) aryl)cinnamamides as pure product.

5a-q

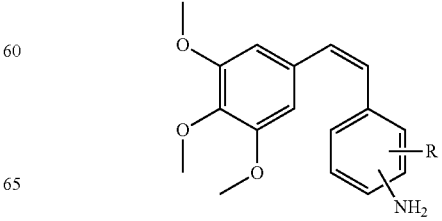

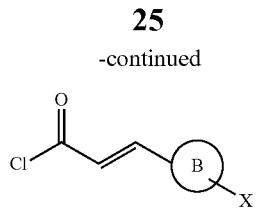

where in
B selected from aryl, heteroaryl and fused heteroaryl ring
R and X selected from H, hydroxy, alkyl, alkoxy, prop-2-ynyloxy, allyloxy, halo, alkylhalides, alkoxy halides, nitro, amine

DETAILED DESCRIPTION OF THE INVENTION

The precursor substituted nitro benzaldehydes(2a-q) are commercial available and 3,4,5-trimethoxybenzylphosphoniumbromide(1) is prepared according to methodology reported by Pettit and coworkers (Pettit, G. R.; Moser, B. R.; Boyd, M. R.; Schmidt, J. M.; Pettit, R. K.; Chapuis, J. C. *Anti-Cancer Drug Des.* 2001, 16, 185) and the preparation of N-((3,4,5-trimethoxystyryl)aryl)cinnamamides of the formulae 8a-af to 24a-af is illustrated in the Scheme.

i. To the stirred solution of nitro benzaldehydes (2a-q) (1 mmol) and 3,4,5-trimethoxybenzyltriphenylphosphonium bromide(14) (1.1 mmol) in anhydrous dichloromethane, sodium hydride (4 mmol) was added at 0° C. and stirred at room temperature for 18 h. The reaction was monitored by TLC using ethyl acetate/hexane as a solvent system. On completion of reaction, appropriate amount of water (until foaming stopped) was added to it and the organic layer was separated and the aqueous layer was extracted with chloroform. The combined organic layer was washed with brine, dried over anhydrous $Na_2SO_4$, and evaporated by using vacuum to get crude compounds, Z-(3a-q) and E-(4a-q) isomeric mixture. The isomers were separated by using column chromatography.

ii. Compounds 3a-q (1 mmol) was dissolved in methanol; ammonium formate (3 mmol) and zinc powder (3 mmol) was added portion wise at 0° C. and stirred at room temperature for 12 hrs. After completion of reaction, the reaction mixture was filtered to remove the residual zinc and the solvent was removed under reduced pressure. The residue was dissolved in ethyl acetate, washed with water and brine solution and dried over anhydrous $Na_2SO_4$. The solvent was removed under reduced pressure and the residue purified by column chromatography using ethyl acetate and hexane as eluents to afford respective amines 5a-q.

iii. To the ice cold solution of substituted cinnamic acids 6a-z (1.1 mmol) in dry dichloromethane, was added oxalyl chloride (3 mmol) and a catalytic amount of N,N-dimethyl formamide (1 mol %) at 0° C. The reaction mixture was stirred for 3h at room temperature and after the completion of reaction the excess solvent and oxalyl chloride was removed under reduced pressure to give respective acid chlorides7a-z.

iv. Respective acid chlorides7a-z dissolved in dry tetrahydrofuran were added to stock solutions of amines 5a-q (1 mmol) and triethylamine (3 mmol) in dry tetrahydrofuran at 0° C. and stirred for 12 h at room temperature. After completion of reaction, the reaction mixture was diluted with ethyl acetate and washed with water and brine solution and dried over anhydrous $Na_2SO_4$. The solvent was removed under reduced pressure and purified by the column chromatography using ethyl acetate and hexane as eluents to afford respective N-((3,4,5-trimethoxystyryl) aryl)cinnamamides as pure products.

v. N-((3,4,5-trimethoxystyryl)aryl)cinnamamide compounds containing nitro group 8-24(d,j,n,u,y,ac; 1 mmol) was subjected to reduction by treating with zinc powder (3 mmol) and ammonium formate (3 mmol) at 0° C. in methanol. The reaction was stirred at room temperature for 12 h and after completion of reaction, the reaction mixture was filtered to remove the residual zinc and the solvent was removed under reduced pressure. The residue was redissolved in ethyl acetate and washed with water and brine solution and dried over anhydrous $Na_2SO_4$. The solvent was removed under reduced pressure and purified by column chromatography using ethyl acetate and hexane as eluents to afford the corresponding amino derivatives 8-24(e,k,p,v,z,ad).

These new analogues of N-((3,4,5-trimethoxystyryl)aryl) cinnamamides were evaluated and have shown promising anticancer activity in various cancer cell lines.

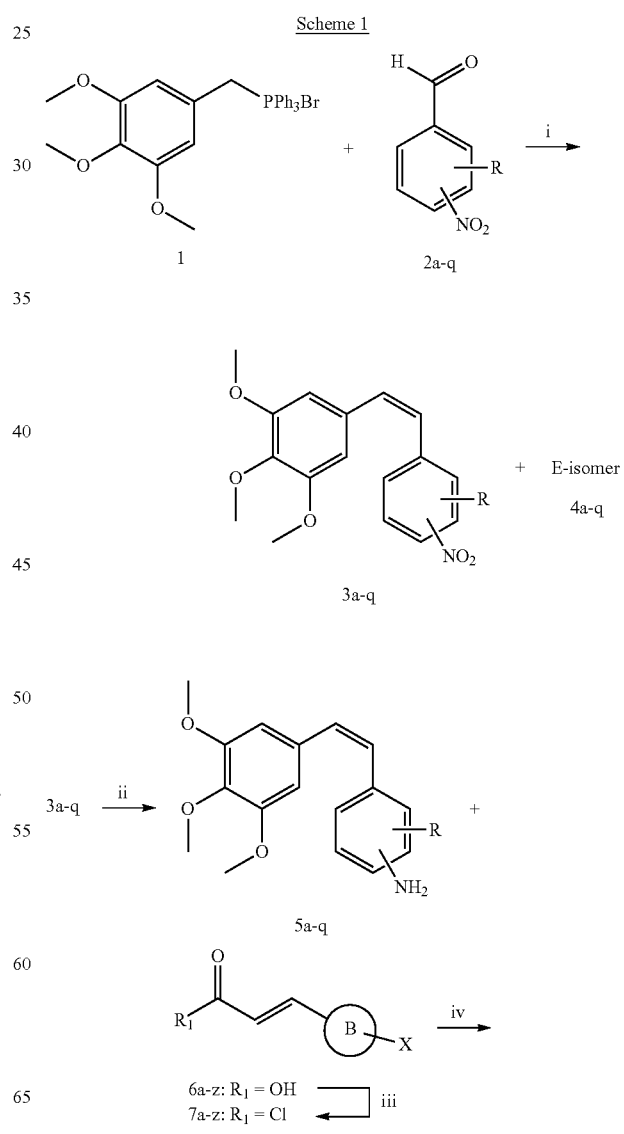

-continued
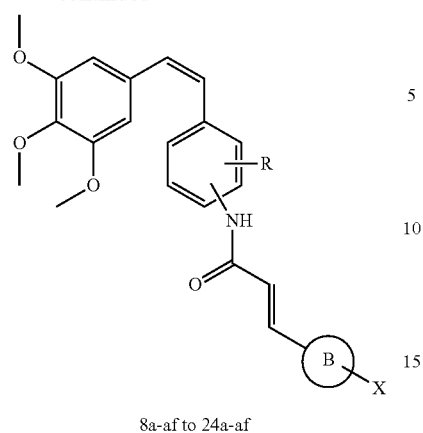
8a-af to 24a-af
Reagents and Conditions:
(i) NaH, CH$_2$Cl$_2$, 18 h, 0° C. to rt; (ii) Zn,HCO$_2$NH$_4$, MeOH, 0° C. to rt, 6h; (iii) oxalyl chloride, CH$_2$Cl$_2$, DMF, 0° C. to rt 3 h; (iv) Et$_3$N, dryTHF, 0° C. to rt, 3 h.
5a
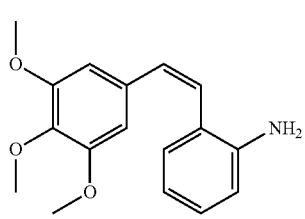
5b
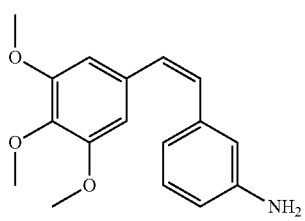
5c
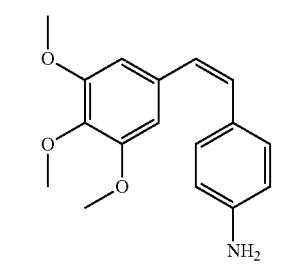
5d
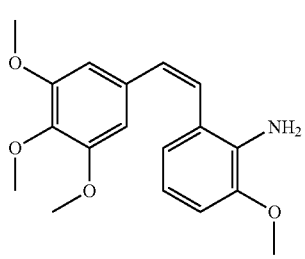
-continued
5e
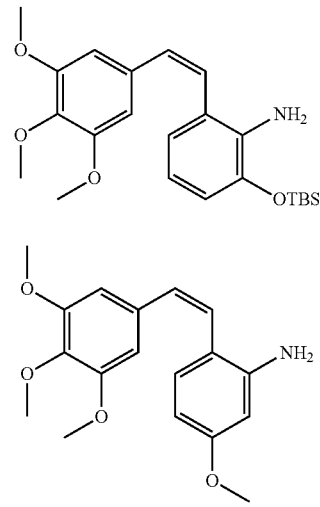
5f
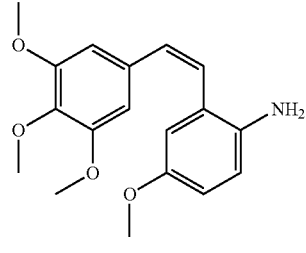
5g
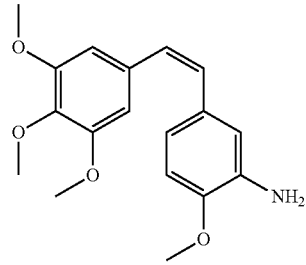
5h
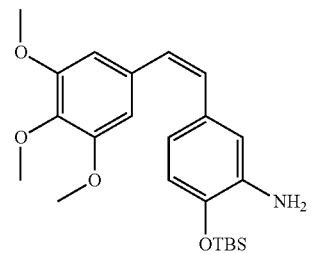
5i
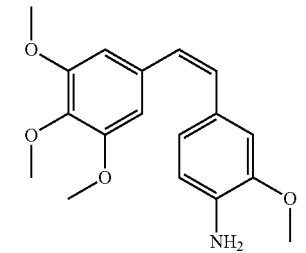
5j -continued
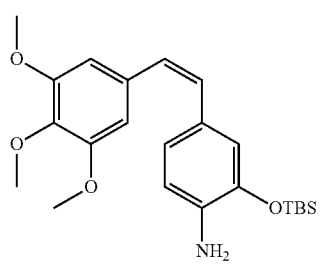
5k
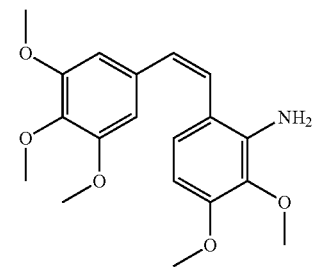
5l
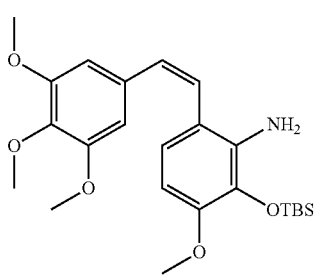
5m
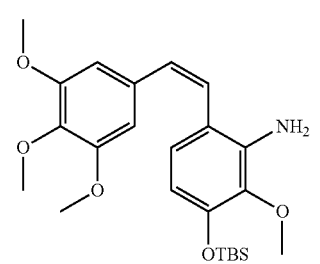
5n
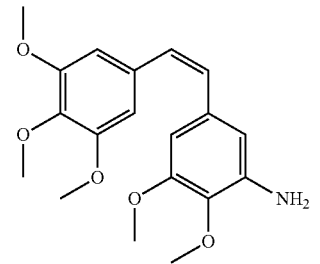
5o
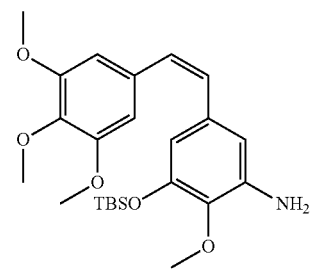
5p
-continued
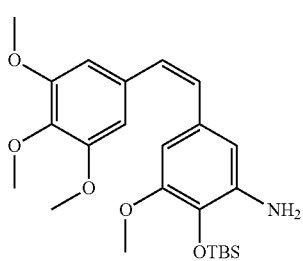
5q
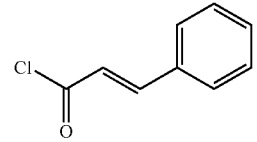
7a
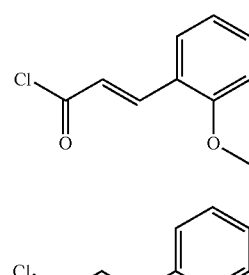
7b
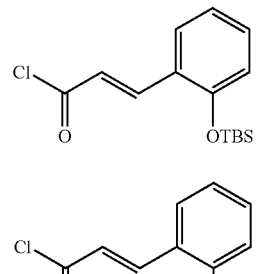
7c
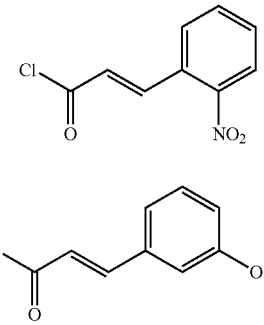
7d
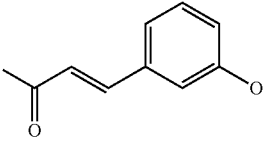
7e
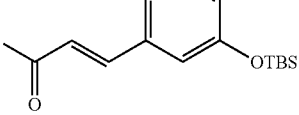
7f
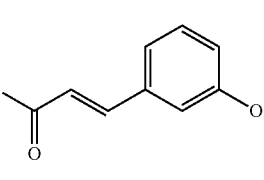
7g
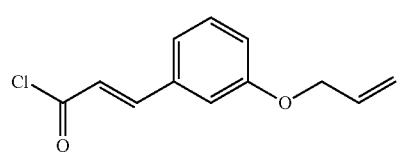
7h

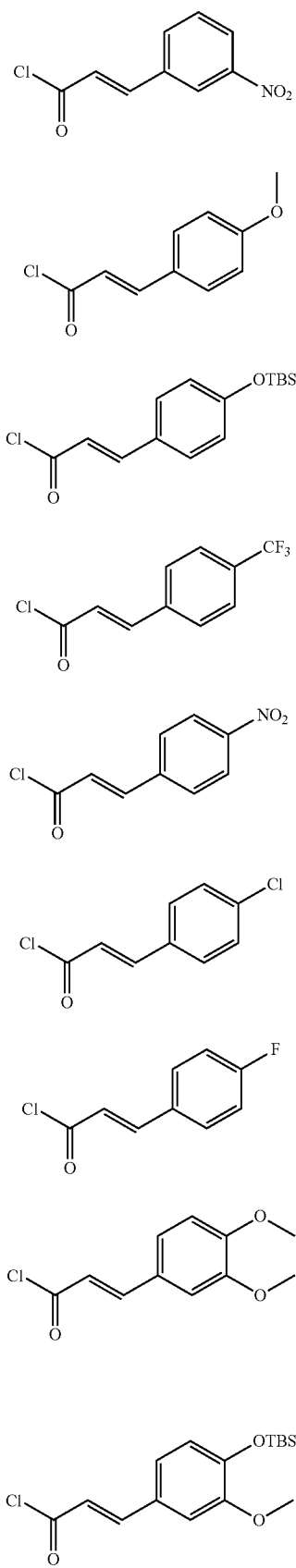
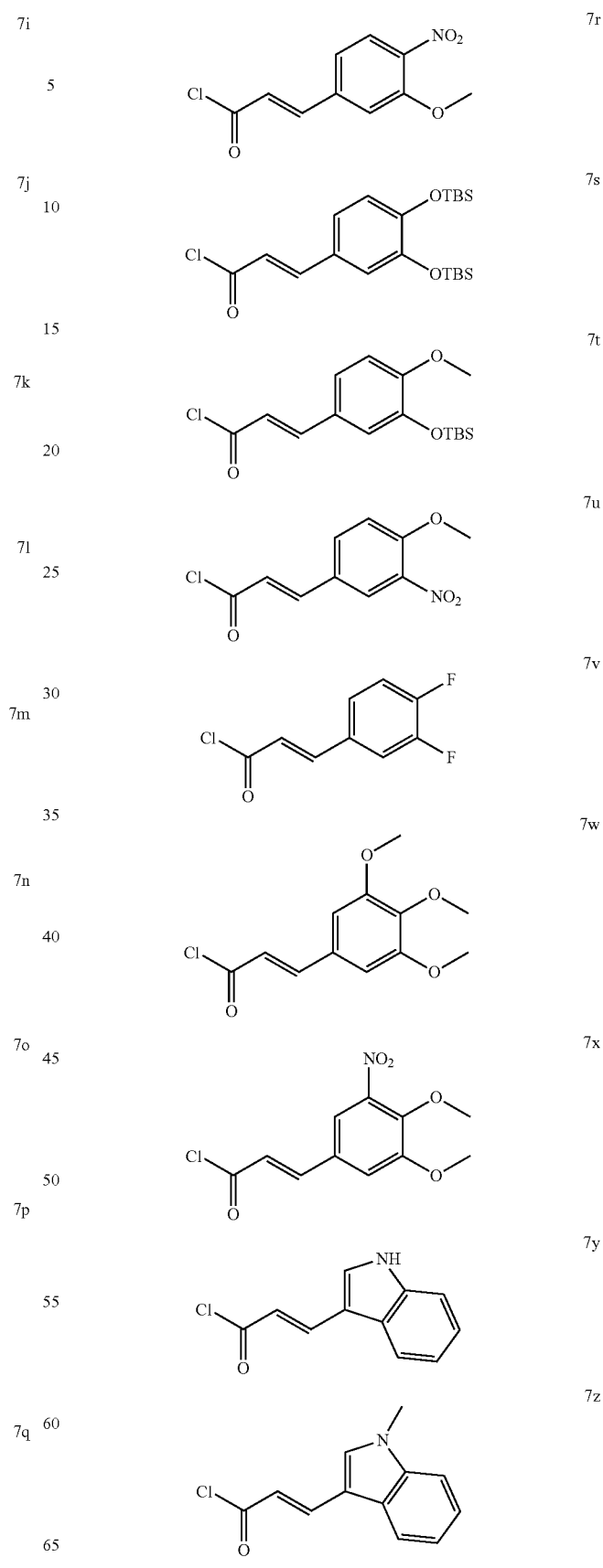

EXAMPLES

The following examples are given by way of illustration of the working of the invention in actual practice and therefore should not be construed to limit the scope of present invention.

Example 1

(E)-N-(2-Hydroxy-3-methoxy-6-(3,4,5-trimethoxystyryl)phenyl)-3-(3-methoxyphenyl)acrylamide (20f)

To the ice cold solution of substituted (E)-3-(3-methoxyphenyl)acrylic acid (6f) (64 mg, 0.36 mmol) in 10 ml dry dichloromethane was added oxalyl chloride (0.09 ml, 1.08 mmol) and a catalytic amount of N,N-dimethyl formamide (1 mol %) at 0° C. The reaction was stirred for 3h at room temperature, after completion of reaction excess of solvent and oxalyl chloride was removed under reduced pressure to give respective acid chloride(7f). The acid chlorides(7f) were dissolved in dry tetrahydrofuran and added to stock solutions of (Z)-2-(tert-butyldimethylsilyloxy)-3-methoxy-6-(3,4,5-trimethoxystyryl)aniline(5m) (150 mg, 0.33 mmol) and triethylamine (0.13 ml, 0.99 mmol) in 10 ml dry tetrahydrofuran at 0° C. The reaction was stirred for 12 h at room temperature and after completion of reaction, the reaction mixture was diluted with ethyl acetate and washed with water and brine solution and dried over anhydrous $Na_2SO_4$ and solvent was removed under reduced pressure. The obtained crude mass was dissolved in 10 ml dry THF and treated with TBAF (0.8 ml, 1.0 M in THF, 2.5 mmol) at 0° C. and stirred at room temperature for 1 h. After completion of reaction, monitored by TLC, the reaction mixture was diluted with ethyl acetate and washed with water and brine solution and dried over anhydrous $Na_2SO_4$. The solvent was removed under reduced pressure to afford a crude mass, which was purified by column chromatography using ethyl acetate and hexane as eluents to afford respective (E)-N-(2-hydroxy-3-methoxy-6-(3,4,5-trimethoxystyryl)phenyl)-3-(3-methoxyphenyl)acrylamide(20f) as solid (107 mg, 65%); $^1$H NMR (500 MHz, $CDCl_3$) δ (ppm): 9.44 (brs, 1H), 7.52 (d, J=15.4 Hz, 1H), 7.29 (t, J=8.0 Hz, 1H), 7.02 (d, J=8.0 Hz, 1H), 6.95 (s, 1H), 6.93 (d, J=8.0 Hz, 1H), 6.86-6.82 (m, 2H), 6.63 (d, J=12.0 Hz, 1H), 6.50 (d, J=12.0 Hz, 1H), 6.38 (s, 2H), 6.18 (d, J=15.4 Hz, 1H), 3.92 (s, 3H), 3.83 (s, 3H), 3.71 (s, 3H), 3.54 (s, 6H); MS (ESI, m/z): 492 $[M+1]^+$.

Example 2

(E)-N-(2-Hydroxy-3-methoxy-6-(3,4,5-trimethoxystyryl)phenyl)-3-(3-hydroxyphenyl)acrylamide (20g)

To the ice cold solution of substituted (E)-3-(3-(tert-butyldimethylsilyloxy)phenyl)acrylic acid (6g) (100.9 mg, 0.36 mmol) in 10 ml dry dichloromethane was added oxalyl chloride (0.09 ml, 1.08 mmol) and a catalytic amount of N,N-dimethyl formamide (1 mol %) at 0° C. The reaction was stirred for 3 h at room temperature, after completion of reaction excess of solvent and oxalyl chloride was removed under reduced pressure to give respective acid chloride (7g). The acid chlorides(7g) were dissolved in dry tetrahydrofuran and added to stock solutions of (Z)-2-(tert-butyldimethylsilyloxy)-3-methoxy-6-(3,4,5-trimethoxystyryl)aniline (5m) (150 mg, 0.33 mmol) and triethylamine (0.13 ml, 0.99 mmol) in 10 ml dry tetrahydrofuran at 0° C. The reaction was stirred for 12 h at room temperature and after completion of reaction, the reaction mixture was diluted with ethyl acetate and washed with water and brine solution and dried over anhydrous $Na_2SO_4$ and solvent was removed under reduced pressure. The obtained crude mass was dissolved in 10 ml dry THF and treated with TBAF (0.8 ml, 1.0 M in THF, 2.5 mmol) at 0° C. and stirred at room temperature for 1 h. After completion of reaction, monitored by TLC, the reaction mixture was diluted with ethyl acetate and washed with water and brine solution and dried over anhydrous $Na_2SO_4$. The solvent was removed under reduced pressure to afford a crude mass, which was purified by column chromatography using ethyl acetate and hexane as eluents to afford respective (E)-N-(2-hydroxy-3-methoxy-6-(3,4,5-trimethoxystyryl)phenyl)-3-(3-hydroxyphenyl)acrylamide (20g) as solid (112 mg, 70%). $^1$H NMR (500 MHz, $CDCl_3$) δ (ppm): 9.49 (brs, 1H), 7.48-7.44 (m, 2H), 7.23 (d, J=8.0 Hz, 1H), 6.99 (d, J=7.4 Hz, 1H), 6.87-6.82 (m, 4H), 6.65 (d, J=12.0 Hz, 1H), 6.52 (d, J=12.0 Hz, 1H), 6.41 (s, 2H), 6.06 (d, J=15.4 Hz, 1H), 5.23 (brs, 1H), 3.92 (s, 3H), 3.72 (s, 3H), 3.56 (s, 6H) MS (ESI, m/z): 478 $[M+1]^+$.

Example 3

(E)-N-(2-Hydroxy-3-methoxy-6-(3,4,5-trimethoxystyryl)phenyl)-3-(3-(prop-2-ynyloxy)phenyl)acrylamide(20h)

To the ice cold solution of substituted (E)-3-(3-(prop-2-ynyloxy)phenyl)acrylic acid (6h) (72 mg, 0.36 mmol) in 10 ml dry dichloromethane was added oxalyl chloride (0.09 ml, 1.08 mmol) and a catalytic amount of N,N-dimethyl formamide (1 mol %) at 0° C. The reaction was stirred for 3 h at room temperature, after completion of reaction excess of solvent and oxalyl chloride was removed under reduced pressure to give respective acid chloride (7h). The acid chloride (7h) was dissolved in dry tetrahydrofuran and added to stock solutions of (Z)-2-(tert-butyldimethylsilyloxy)-3-methoxy-6-(3,4,5-trimethoxystyryl)aniline (5m) (150 mg, 0.33 mmol) and triethylamine (0.13 ml, 0.99 mmol) in 10 ml dry tetrahydrofuran at 0° C. The reaction was stirred for 12 h at room temperature and after completion of reaction, the reaction mixture was diluted with ethyl acetate and washed with water and brine solution and dried over anhydrous $Na_2SO_4$ and solvent was removed under reduced pressure. The obtained crude mass was dissolved in 10 ml dry THF and treated with TBAF (0.8 ml, 1.0 M in THF, 2.5 mmol) at 0° C. and stirred at room temperature for 1 h. After completion of reaction, monitored by TLC, the reaction mixture was diluted with ethyl acetate and washed with water and brine solution and dried over anhydrous $Na_2SO_4$. The solvent was removed under reduced pressure to afford a crude mass, which was purified by column chromatography using ethyl acetate and hexane as eluents to afford respective (E)-N-(2-hydroxy-3-methoxy-6-(3,4,5-trimethoxystyryl)phenyl)-3-(3-(prop-2-ynyloxy)phenyl) acrylamide(20h) as solid (115 mg, 68%). $^1$H NMR (500 MHz, $CDCl_3$) δ (ppm): 9.41 (s, 1H), 7.51 (d, J=15.4 Hz, 1H), 7.46 (s, 1H), 7.32-7.29 (m, 1H), 7.08-6.99 (m, 3H), 6.86-6.82 (m, 2H), 6.65 (d, J=12.0 Hz, 1H), 6.50 (d, J=12.0 Hz, 1H), 6.38 (s, 2H), 6.18 (d, J=15.4 Hz, 1H), 4.27 (d, J=2.28 Hz, 2H), 3.92 (s, 3H), 3.71 (s, 3H), 3.54 (s, 6H), 2.55 (t, J=2.28 Hz, 1H) MS (ESI, m/z): 538 $[M+Na]^+$.

Example 4

(E)-3-(3-(Allyloxy)phenyl)-N-(2-hydroxy-3-methoxy-6-(3,4,5-trimethoxystyryl)phenyl)acrylamide(20i)

The title compound was prepared starting with substituted (E)-3-(3-(allyloxy)phenyl)acrylic acid (6i) (73 mg, 0.36 mmol) and (Z)-2-(tert-butyldimethylsilyloxy)-3-methoxy-6-(3,4,5-trimethoxystyryl)aniline (5m) (150 mg, 0.33 mmol) employing the procedure described in Examples 1-3 as solid (110 mg, 65%). $^1$H NMR (300 MHz, CDCl$_3$) δ (ppm): 9.43 (s, 1H), 7.50 (d, J=15.8 Hz, 1H), 7.42 (s, H), 7.05-6.89 (m, 3H), 6.84 (s, 2H), 6.69 (s, 1H), 6.63 (d, J=12.0 Hz, 1H), 6.50 (d, J=12.0 Hz, 1H), 6.38-6.37 (m, 2H), 6.15 (d, J=15.8 Hz, 1H), 6.07-5.98 (m, 1H), 5.40 (d, J=16.6 Hz, 1H), 5.29 (dd, J=16.6 Hz, 9.82 Hz, 1H), 4.55 (d, J=4.5 Hz, 1H), 3.92 (s, 6H), 3.71 (s, 3H), 3.54 (s, 3H). MS (ESI, m/z): 540 [M+Na]$^+$.

Example 5

(E)-N-(2-Hydroxy-3-methoxy-6-(3,4,5-trimethoxystyryl)phenyl)-3-(4-(trifluoromethyl)phenyl)acrylamide(20n)

The title compound was prepared starting with substituted (E)-3-(4-(trifluoromethyl)phenyl)acrylic acid (6n) (77 mg, 0.36 mmol) and (Z)-2-(tert-butyldimethylsilyloxy)-3-methoxy-6-(3,4,5-trimethoxystyryl)aniline (5m) (150 mg, 0.33 mmol) employing the procedure described in Examples 1-3 as solid (129 mg, 74%). $^1$H NMR (300 MHz, CDCl$_3$) δ (ppm): 9.18 (brs, 1H), 7.65-7.53 (m, 5H), 7.46 (s, 1H), 6.89-6.82 (m, 2H), 6.62 (d, J=12.0 Hz, 1H), 6.51 (d, J=12.0, 1H), 6.37 (s, 2H), 6.25 (d, J=15.2 Hz, 1H), 3.92 (s, 3H), 3.72 (s, 3H), 3.53 (s, 6H), MS (ESI, m/z): 530 [M+1]$^+$.

Example 6

(E)-N-(2-Hydroxy-3-methoxy-6-(3,4,5-trimethoxystyryl)phenyl)-3-(4-nitrophenyl)acrylamide(20o)

The title compound was prepared starting with substituted (E)-3-(4-nitrophenyl)acrylic acid (6o) (69 mg, 0.36 mmol) and (Z)-2-(tert-butyldimethylsilyloxy)-3-methoxy-6-(3,4,5-trimethoxystyryl)aniline (5m) (150 mg, 0.33 mmol) employing the procedure described in Examples 1-3 as solid (120 mg, 72%). $^1$H NMR (500 MHz, CDCl$_3$) δ (ppm): 9.02 (s, 1H), 8.25 (d, J=8.5 Hz, 2H), 7.59-7.56 (m, 3H), 7.49 (s, 1H), 6.89-6.84 (m, 2H), 6.56 (d, J=12.0 Hz, 1H), 6.51 (d, J=12.0 Hz, 1H), 6.37 (s, 2H), 6.31 (d, J=15.4 Hz, 1H), 3.93 (s, 3H), 3.72 (s, 3H), 3.54 (s, 6H), MS (ESI, m/z): 507 [M+1]$^+$.

Example 7

(E)-3-(4-Chlorophenyl)-N-(2-hydroxy-3-methoxy-6-(3,4,5-trimethoxystyryl)phenyl)acrylamide(20q)

The title compound was prepared starting with substituted (E)-3-(4-chlorophenyl)acrylic acid (6q) (65 mg, 0.36 mmol) and (Z)-2-(tert-butyldimethylsilyloxy)-3-methoxy-6-(3,4,5-trimethoxystyryl)aniline (5m) (150 mg, 0.33 mmol) employing the procedure described in Examples 1-3 as solid (115 mg 71%). $^1$H NMR (300 MHz, CDCl$_3$) δ (ppm): 9.33 (brs, 1H), 7.49 (d, J=15.2 Hz, 1H), 7.41 (brs, 1H), 7.39-7.33 (m, 4H), 6.84 (d, J=8.4 Hz, 2H), 6.64 (d, J=12.0 Hz, 1H), 6.50 (d, J=12.0 Hz, 1H), 6.37 (s, 2H), 6.14 (d, J=15.2 Hz, 1H), 3.92 (s, 3H), 3.71 (s, 3H), 3.54 (s, 6H); MS (ESI, m/z): 496 [M+1]$^+$.

Example 8

(E)-3-(4-Fluorophenyl)-N-(2-hydroxy-3-methoxy-6-(3,4,5-trimethoxystyryl)phenyl)acrylamide(20r)

The title compound was prepared starting with substituted (E)-3-(4-fluorophenyl)acrylic acid (6r) (59 mg, 0.36 mmol) and (Z)-2-(tert-butyldimethylsilyloxy)-3-methoxy-6-(3,4,5-trimethoxystyryl)aniline (5m) (150 mg, 0.33 mmol) employing the procedure described in Examples 1-3 as solid (110 mg 70%). $^1$H NMR (500 MHz, CDCl$_3$) δ (ppm): 9.38 (s, 1H), 7.51 (d, J=15.4 Hz, 1H), 7.44-7.41 (m, 3H), 7.08-7.05 (m, 2H), 6.86-6.82 (m, 2H), 6.64 (d, J=12.0 Hz, 1H), 6.52 (d, J=12.0 Hz, 1H), 6.38 (s, 2H), 6.10 (d, J=15.4 Hz, 1H), 3.92 (s, 3H), 3.71 (s, 3H), 3.54 (s, 6H), MS (ESI, m/z): 480 [M+1]$^+$;

Example 9

(E)-3-(3,4-Dimethoxyphenyl)-N-(2-hydroxy-3-methoxy-6-(3,4,5-trimethoxystyryl)phenyl)acrylamide(20s)

The title compound was prepared starting with substituted (E)-3-(3,4-dimethoxyphenyl)acrylic acid (6s) (74 mg, 0.36 mmol) and (Z)-2-(tert-butyldimethylsilyloxy)-3-methoxy-6-(3,4,5-trimethoxystyryl)aniline (5m) (150 mg, 0.33 mmol) employing the procedure described in Examples 1-3 as solid (111 mg, 65%). $^1$H NMR (500 MHz, CDCl$_3$) δ (ppm): 9.48 (s, 1H), 7.52 (d, J=15.2 Hz, 1H), 7.41 (s, 1H), 7.05 (d, J=7.4 Hz, 1H), 6.96 (s, 1H), 6.86-6.82 (m, 3H), 6.63 (d, J=11.4 Hz, 1H), 6.51 (d, J=11.4 Hz, 1H), 6.39 (s, 1H), 6.12 (d, J=15.2 Hz, 1H), 3.90 (s, 9H), 3.73 (s, 3H), 3.55 (s, 6H), MS (ESI, m/z): 522 [M+1]$^+$.

Example 10

(E)-N-(2-Hydroxy-3-methoxy-6-(3,4,5-trimethoxystyryl)phenyl)-3-(4-hydroxy-3-methoxyphenyl)acrylamide(20t)

The title compound was prepared starting with substituted (E)-3-(4-hydroxy-3-methoxyphenyl)acrylic acid (6t) (69 mg, 0.36 mmol) and (Z)-2-(tert-butyldimethylsilyloxy)-3-methoxy-6-(3,4,5-trimethoxystyryl)aniline (5m) (150 mg, 0.33 mmol) employing the procedure described in Examples 1-3 as solid (116 mg, 67%). $^1$H NMR (300 MHz, CDCl$_3$) δ (ppm): 9.52 (brs, 1H), 7.47 (d, J=15.4 Hz, 1H), 7.39 (s, 1H), 7.03 (d, J=8.2 Hz, 1H), 6.92-6.90 (m, 2H), 6.85-6.80 (m, 2H), 6.63 (d, J=12.0 Hz, 1H), 6.52 (d, J=12.0 Hz, 1H), 6.38 (s, 2H), 6.07 (d, J=15.4 Hz, 1H), 5.87 (brs, 1H), 3.92 (s, 6H), 3.73 (s, 3H), 3.54 (s, 6H) MS (ESI, m/z): 530 [M+1]$^+$.

Example 11

(E)-N-(2-Hydroxy-3-methoxy-6-(3,4,5-trimethoxystyryl)phenyl)-3-(3-methoxy-4-nitrophenyl)acrylamide(20u)

The title compound was prepared starting with substituted (E)-3-(3-methoxy-4-nitrophenyl)acrylic acid (6u) (80 mg, 0.36 mmol) and (Z)-2-(tert-butyldimethylsilyloxy)-3-methoxy-6-(3,4,5-trimethoxystyryl)aniline (5m) (150 mg, 0.33 mmol) employing the procedure described in Examples 1-3 as solid (134 mg, 76%). $^1$H NMR (300 MHz, CDCl$_3$) δ (ppm): 9.01 (brs, 1H), 7.87 (d, J=8.3 Hz, 1H), 7.49-7.43 (m, 2H), 7.10-7.08 (m, 2H), 6.86 (s, 2H), 6.62 (d, J=12.0 Hz, 1H), 6.49 (d, J=12.0 Hz, 1H), 6.35 (s, 2H), 6.25 (d, J=15.8 Hz, 1H), 4.01 (s, 3H), 3.92 (s, 3H), 3.73 (s, 3H), 3.51 (s, 6H) MS (ESI, m/z): 537 [M+1]$^+$.

Example 12

(E)-3-(4-Amino-3-methoxyphenyl)-N-(2-hydroxy-3-methoxy-6-(3,4,5-trimethoxystyryl)phenyl)acrylamide(20v)

To a solution of (E)-N-(2-hydroxy-3-methoxy-6-(3,4,5-trimethoxystyryl)phenyl)-3-(3-methoxy-4-nitrophenyl)acrylamide(20u) (100 mg, 0.18 mmol) in methanol, ammonium formate (34.6 mg, 0.55 mmol) and zinc powder (35 mg, 0.55 mmol) was added portion wise at 0° C. and stirred at room temperature for 12 h. After completion of reaction, the reaction mixture was filtered to remove the residual zinc and the solvent was removed under reduced pressure. The residue was dissolved in ethyl acetate, washed with water and brine solution and dried over anhydrous Na$_2$SO$_4$. The solvent was removed under reduced pressure and the residue purified by column chromatography using ethyl acetate and hexane as eluents to afford (E)-3-(4-amino-3-methoxyphenyl)-N-(2-hydroxy-3-methoxy-6-(3,4,5-trimethoxystyryl)phenyl)acrylamide(20v) as solid (60 mg, 65%). $^1$H NMR (500 MHz, CDCl$_3$) δ (ppm): 9.69 (brs, 1H), 7.47 (d, J=15.2 Hz, 1H), 7.37 (brs, 1H), 6.95 (d, J=8.0 Hz, 2H), 6.86 (s, 1H), 6.83-6.79 (m, 2H), 6.65-6.63 (m, 2H), 6.51 (d, J=12.0 Hz, 1H), 6.39 (s, 2H), 6.03 (d, J=15.2 Hz, 1H), 4.12 (brs, 2H), 3.91 (s, 3H), 3.88 (s, 3H), 3.73 (s, 3H), 3.55 (s, 6H) MS (ESI, m/z): 507 [M+1]$^+$.

Example 13

(E)-N-(2-hydroxy-3-methoxy-6-(3,4,5-trimethoxystyryl)phenyl)-3-(3-hydroxy-4-methoxyphenyl)acrylamide(20x)

The title compound was prepared starting with substituted (E)-3-(3-hydroxy-4-methoxyphenyl)acrylic acid (6x) (69 mg, 0.36 mmol) and (Z)-2-(tert-butyldimethylsilyloxy)-3-methoxy-6-(3,4,5-trimethoxystyryl)aniline (5m) (150 mg, 0.33 mmol) employing the procedure described in Examples 1-3 as solid (110 mg, 66%). $^1$H NMR (300 MHz, CDCl$_3$) δ (ppm): 9.68 (s, 1H), 7.43 (d, J=15.1 Hz, 1H), 7.40 (s, 1H), 7.03 (s, 1H), 6.92 (d, J=8.3 Hz, 1H), 6.86-6.81 (m, 3H), 6.66 (d, J=12.0 Hz, 1H), 6.51 (d, J=12.0 Hz, 1H), 6.40 (s, 2H), 6.00 (d, J=15.1 Hz, 1H), 3.93 (s, 3H), 3.92 (s, 3H), 3.68 (s, 3H), 3.57 (s, 6H), MS (ESI, m/z): 508 [M+1]$^+$.

Example 14

(E)-N-(2-Hydroxy-3-methoxy-6-(3,4,5-trimethoxystyryl)phenyl)-3-(4-methoxy-3-nitrophenyl)acrylamide(20y)

The title compound was prepared starting with substituted (E)-3-(4-methoxy-3-nitrophenyl)acrylic acid (6y) (80 mg, 0.36 mmol) and (Z)-2-(tert-butyldimethylsilyloxy)-3-methoxy-6-(3,4,5-trimethoxystyryl)aniline (5m) (150 mg, 0.33 mmol) employing the procedure described in Examples 1-3 as solid (130 mg, 74%). $^1$H NMR (300 MHz, CDCl$_3$) δ (ppm): 9.35 (s, 1H), 7.97 (s, 1H), 7.56 (d, J=8.3 Hz, 1H), 7.51-7.43 (m, 2H), 7.08 (d, J=8.3 Hz, 1H), 6.85 (d, J=2.2 Hz, 2H), 6.64 (d, J=12.1 Hz, 1H), 6.52 (d, J=12.1 Hz, 1H), 6.39 (s, 2H), 6.12 (d, J=15.8 Hz, 1H), 4.00 (s, 3H), 3.92 (s, 3H), 3.70 (s, 3H), 3.56 (s, 6H); MS (ESI, m/z): 537 [M+1]$^+$.

Example 15

(E)-3-(3-Amino-4-methoxyphenyl)-N-(2-hydroxy-3-methoxy-6-(3,4,5-trimethoxystyryl)phenyl)acrylamide (20z)

The title compound was prepared starting with (E)-N-(2-hydroxy-3-methoxy-6-(3,4,5-trimethoxystyryl)phenyl)-3-(4-methoxy-3-nitrophenyl)acrylamide(20y) (100 mg, 0.18 mmol) employing the procedure described in Example 12 as solid (55 mg, 60%). $^1$H NMR (500 MHz, CDCl$_3$) δ (ppm): 9.63 (s, 1H), 7.42 (d, J=15.4 Hz, 1H), 1H (bs, 1H), 6.85-6.80 (m, 4H), 6.75 (d, J=8.4, 1H), 6.64 (d, J=12.0 Hz, 1H), 6.51 (d, J=12.0 Hz, 1H), 6.39 (s, 2H), 6.01 (d, J=15.4 Hz, 1H), 3.90 (s, 3H), 3.88 (s, 3H), 3.70 (s, 3H), 3.56 (s, 6H) MS (ESI, m/z): 507 [M+1]$^+$.

Example 16

(E)-3-(3,4-Difluorophenyl)-N-(2-hydroxy-3-methoxy-6-(3,4,5-trimethoxystyryl)phenyl)acrylamide(20aa)

The title compound was prepared starting with substituted (E)-3-(3,4-difluorophenyl)acrylic acid (6aa) (66 mg, 0.36 mmol) and (Z)-2-(tert-butyldimethylsilyloxy)-3-methoxy-6-(3,4,5-trimethoxystyryl)aniline (5m) (150 mg, 0.33 mmol) employing the procedure described in Examples 1-3 as solid (121 mg, 74%). $^1$H NMR (300 MHz, CDCl$_3$) δ (ppm): 9.30 (brs, 1H), 7.49-7.42 (m, 2H), 7.26-7.14 (m, 3H), 6.84 (d, J=2.2 Hz, 2H), 6.64 (d, J=12.0 Hz, 1H), 6.51 (d, J=12.0 Hz, 1H), 6.38 (s, 2H), 6.05 (d, J=15.1 Hz, 1H), 3.92 (s, 3H), 3.70 (s, 3H), 3.56 (s, 6H) MS (ESI, m/z): 498 [M+1]$^+$.

Example 17

(E)-N-(2-Hydroxy-3-methoxy-6-(3,4,5-trimethoxystyryl)phenyl)-3-(3,4,5-trimethoxyphenyl)acrylamide(20ab)

The title compound was prepared starting with substituted (E)-3-(3,4,5-trimethoxyphenyl)acrylic acid (6ab) (85 mg, 0.36 mmol) and (Z)-2-(tert-butyldimethylsilyloxy)-3-methoxy-6-(3,4,5-trimethoxystyryl)aniline (5m) (150 mg, 0.33 mmol) employing the procedure described in Examples 1-3 as solid (136 mg, 75%). $^1$H NMR (300 MHz, CDCl$_3$) δ (ppm): 9.32 (s, 1H), 7.44 (d, J=15.1 Hz, 1H), 7.40 (s, 1H), 6.83 (d, J=8.3 Hz, 2H), 6.68 (s, 2H), 6.63 (d, J=12.0 Hz, 1H), 6.50 (d, J=12.0 Hz, 1H), 6.37 (s, 2H), 6.14 (d, J=15.1 Hz, 1H), 3.90 (s, 3H), 3.89 (s, 6H), 3.88 (s, 3H), 3.75 (s, 3H), 3.53 (s, 6H); MS (ESI, m/z): 552 [M+1]$^+$.

Biological Results

The synthesized N-(3,4,5-trimethoxystyryl)aryl)cinnamamides were evaluated for their anti-proliferative activity in selected human cancer cell lines of breast cancer (MCF-7), prostate cancer (DU-145), lung cancer (Hop-62), cervical cancer (Hela), leukemia (K562), ovarian cancer (SK-OV-3), colon cancer (Colo-205), pancreatic (MAIPA-CA-2) by using sulforhodamine B (SRB) method (Vichai, V.; Kirtikara, K. Nat. Protoc. 2006, 1, 1112). The compounds that exhibit $GI_{50} \leq 10^{-5}$ M are considered to be active on the respective cell lines and the results are illustrated in Table 1. CA-4 was used as the reference compound. All the compounds exhibited significant anticancer activity with $GI_{50}$ values ranging from 0.031 to >100 μM.

TABLE 1

In vitro anticancer activity of compounds in selected cancer cell lines (GI$_{50}$ values in μM) [a]

| Compound | MCF-7[b] | DU-145[c] | Hop-62[d] | Hela[e] | K562[f] | SK-OV-3[g] | Colo-205[h] | MAIPA-CA-2[i] |
|---|---|---|---|---|---|---|---|---|
| 20f | 59.5 | >100 | 65.4 | 18.1 | 0.098 | 17.6 | >100 | 93.9 |
| 20g | 0.063 | 0.070 | 0.082 | 0.0949 | 0.094 | 0.097 | 13.4 | 0.098 |
| 20h | 11.6 | 96.4 | >100 | >100 | >100 | >100 | >100 | >100 |
| 20i | 0.083 | 0.085 | 0.060 | 0.0787 | 0.091 | 0.082 | 18.0 | 0.098 |
| 20n | 83.7 | >100 | >100 | >100 | 58.0 | >100 | >100 | >100 |
| 20o | 0.072 | 0.085 | 0.061 | 15.7 | 0.097 | 17.0 | 10.3 | 40.8 |
| 20q | 55.5 | 54.1 | 79.4 | 38.8 | 24.9 | 62.6 | >100 | >100 |
| 20r | 0.066 | 0.083 | 43.0 | 24.0 | 23.5 | 47.5 | 67.6 | 78.1 |
| 20s | 0.056 | 0.060 | 0.090 | 7.5 | 0.094 | 0.099 | 0.099 | 29.9 |
| 20t | 0.060 | 0.072 | 0.079 | 0.090 | 0.093 | 0.096 | 0.098 | 0.098 |
| 20u | 0.095 | 0.075 | 0.084 | 0.099 | 0.096 | 7.9 | 0.096 | 23.5 |
| 20v | 0.074 | 0.085 | 0.035 | 0.090 | 0.082 | 0.094 | 0.086 | 0.097 |
| 20x | 0.095 | 0.117 | 17.1 | 15.9 | 23.7 | 1.8 | >100 | 46.3 |
| 20y | 19.4 | 64.7 | 71.3 | 49.2 | 46.8 | 52.6 | >100 | >100 |
| 20z | 0.050 | 0.079 | 0.044 | 0.091 | 0.089 | 0.097 | 0.089 | 14.3 |
| 20aa | 0.031 | 0.045 | 43.6 | 29.2 | 0.099 | 29.8 | 74.9 | 74.0 |
| 20ab | 0.079 | 0.095 | 24.8 | 14.9 | 28.0 | 20.9 | 76.0 | 64.5 |
| CA-4 | 0.033 | 0.046 | 0.15[j] | 0.008 | 0.031[j] | 31.6[j] | 0.025 | nd |

[a] Concentration of drug causing 50% inhibition of cell growth,
[b] Human breast cancer,
[c] Human prostate cancer,
[d] Human lung cancer,
[e] Human cervical cancer,
[f] Human leukemia,
[g] Human ovarian cancer,
[h] Human colon cancer,
[i] Humanpancreatic,
[j] Data from NCI60 dose response (NSC 613729, http://dtp.nci.nih.gov/dtpstandard/dwindex/index.jsp),
nd = not determined.

Significance of the Work Carried Out

The N-((3,4,5-trimethoxystyryl)aryl)cinnamamide derivatives that have been synthesized exhibited significant antiproliferative activity against different human cancer cell lines Advantages of the Invention 1. The present invention provides new N-((3,4,5-trimethoxystyryl)aryl)cinnamamide compounds useful as anticancer agents.
2. It also provides a process for the preparation of the novel N-((3,4,5-trimethoxystyryl)aryl)cinnamamide compounds.

The invention claimed is:

1. N-((3,4,5-trimethoxystyryl)aryl)cinnamamide compounds of general formula A:

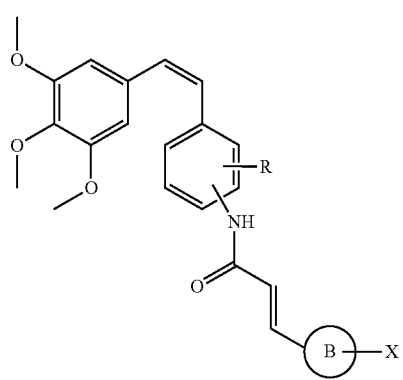

formula A wherein
B is selected from aryl, heteroaryl and fused heteroaryl ring; and
R and X are independently selected from H, hydroxyl, alkyl, alkoxy, prop-2-ynyloxy, allyloxy, halo, alkylhalides, alkoxy halides, nitro, and amine.

2. A compound as claimed in claim 1, wherein the structural formula of the compound is represented by one of formulae 8a-8af, 9a-9af, 10a-10af, 11a-11af, 12a-12af, 13a-13af, 14a-14af, 15a-15af, 16a-16af, 17a-17af, 18a-18af, 19a-19af, 20a-20af, 21a-21af, 22a-22af, 23a-23af, and 24a-24af:

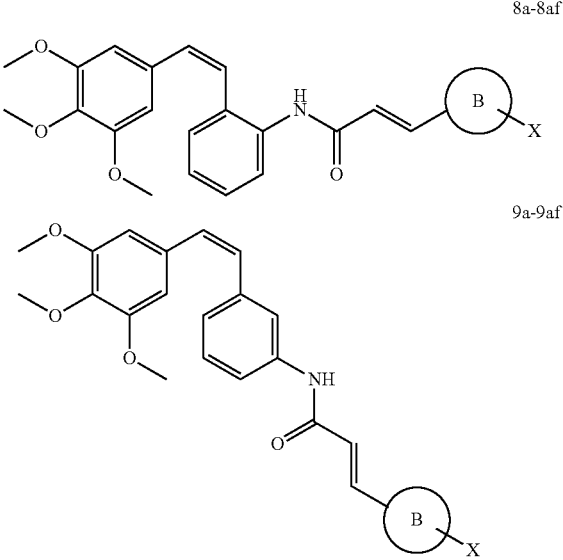

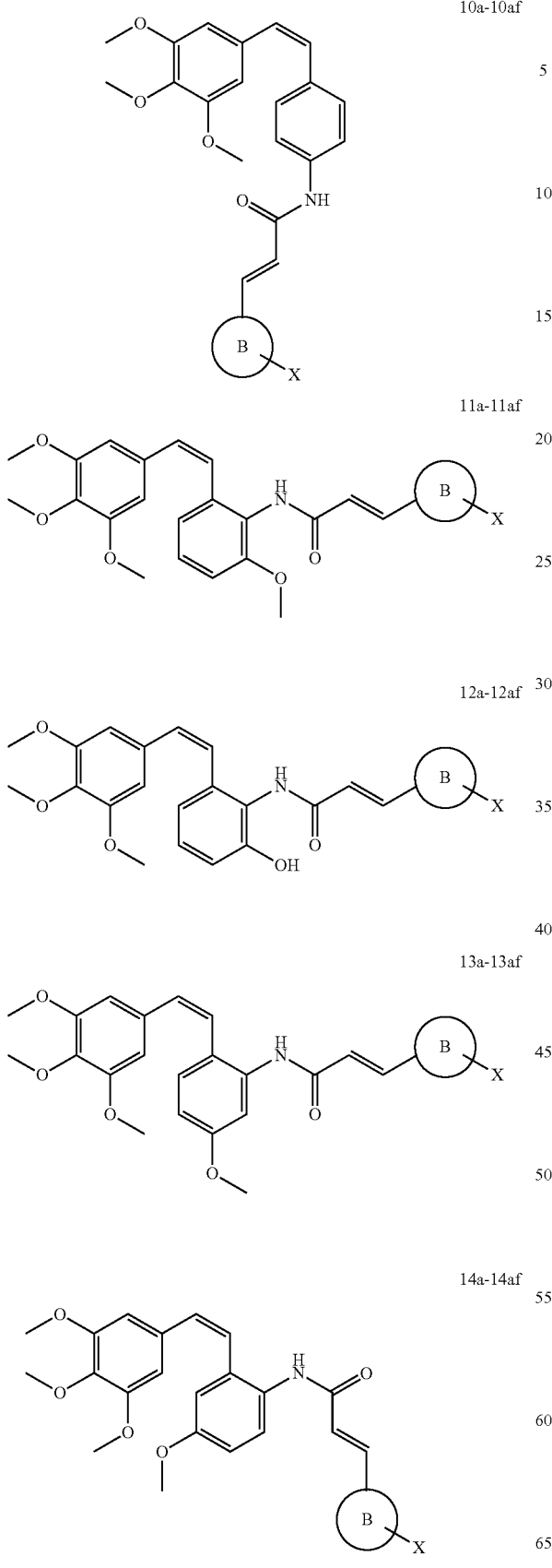
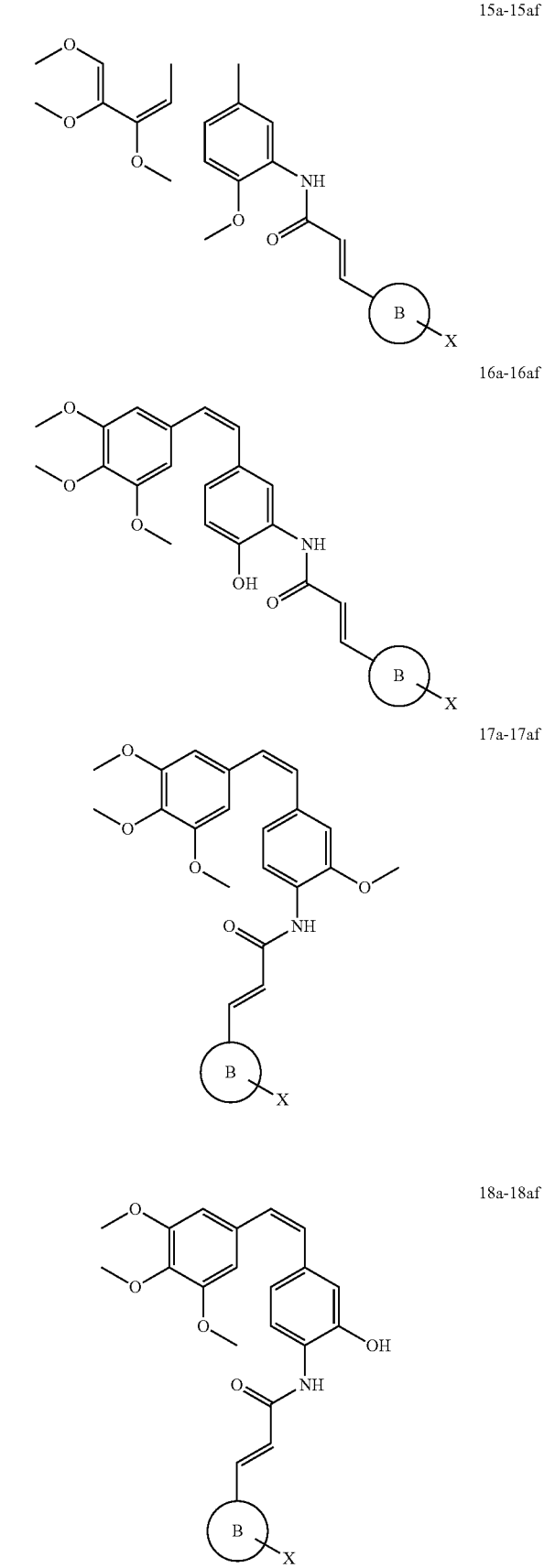

-continued 19a-19af

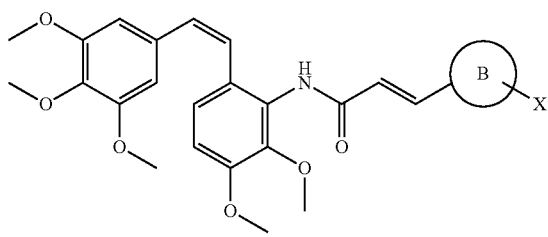

20a-20af

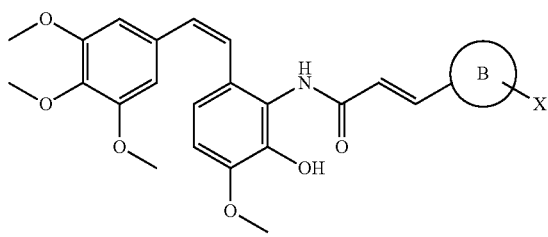

21a-21af

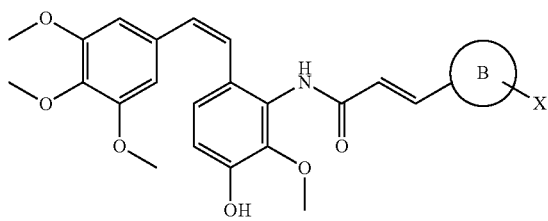

22a-22af

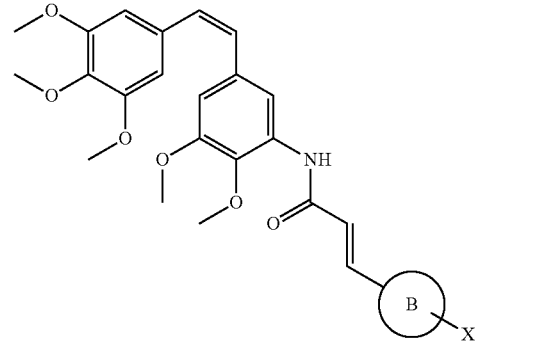

23a-23af

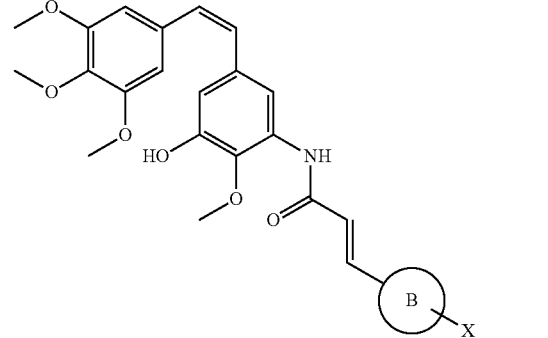

-continued 24a-24af

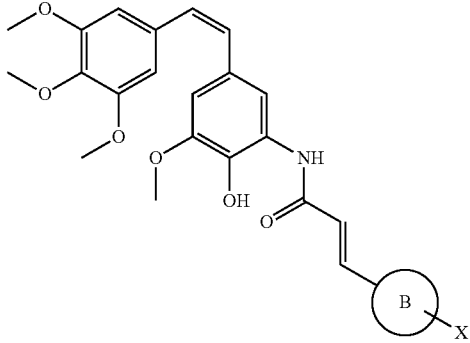

wherein
B is selected from aryl, heteroaryl and fused heteroaryl ring; and
X is independently selected from H, hydroxyl, alkyl, alkoxy, prop-2-ynyloxy, allyloxy, halo, alkylhalides, alkoxy halides, nitro, and amine.

3. A compound as claimed in claim 1, wherein the compound of formula A is:
N-(2-(3,4,5-Trimethoxystyryl)phenyl)cinnamamide(8a),
(E)-3-(2-Methoxyphenyl)-N-(2-(3,4,5-trimethoxystyryl)phenyl)acrylamide(8b),
(E)-3-(2-Nitrophenyl)-N-(2-(3,4,5-trimethoxystyryl)phenyl)acrylamide(8d),
(E)-3-(2-Aminophenyl)-N-(2-(3,4,5-trimethoxystyryl)phenyl)acrylamide(8e),
(E)-3-(3-Methoxyphenyl)-N-(2-(3,4,5-trimethoxystyryl)phenyl)acrylamide(8f),
(E)-3-(3-Hydroxyphenyl)-N-(2-(3,4,5-trimethoxystyryl)phenyl)acrylamide(8g),
(E)-3-(3-(Prop-2-ynyloxy)phenyl)-N-(2-(3,4,5-trimethoxystyryl)phenyl)acrylamide(8h),
(E)-3-(3-(Allyloxy)phenyl)-N-(2-(3,4,5-trimethoxystyryl)phenyl)acrylamide(8i),
(E)-3-(3-Nitrophenyl)-N-(2-(3,4,5-trimethoxystyryl)phenyl)acrylamide(8j),
(E)-3-(3-Aminophenyl)-N-(2-(3,4,5-trimethoxystyryl)phenyl)acrylamide(8k),
(E)-3-(4-Methoxyphenyl)-N-(2-(3,4,5-trimethoxystyryl)phenyl)acrylamide(8l),
(E)-3-(4-Hydroxyphenyl)-N-(2-(3,4,5-trimethoxystyryl)phenyl)acrylamide(8m),
(E)-3-(4-(Trifluoromethyl)phenyl)-N-(2-(3,4,5-trimethoxystyryl)phenyl)acrylamide(8n),
(E)-3-(4-Nitrophenyl)-N-(2-(3,4,5-trimethoxystyryl)phenyl)acrylamide(8o),
(E)-3-(4-Aminophenyl)-N-(2-(3,4,5-trimethoxystyryl)phenyl)acrylamide(8p),
(E)-3-(4-Chlorophenyl)-N-(2-(3,4,5-trimethoxystyryl)phenyl)acrylamide(8q),
(E)-3-(4-Fluorophenyl)-N-(2-(3,4,5-trimethoxystyryl)phenyl)acrylamide(8r),
(E)-3-(3,4-Dimethoxyphenyl)-N-(2-(3,4,5-trimethoxystyryl)phenyl)acrylamide(8s),
(E)-3-(4-Hydroxy-3-methoxyphenyl)-N-(2-(3,4,5-trimethoxystyryl)phenyl)acrylamide(8t),
(E)-3-(3-Methoxy-4-nitrophenyl)-N-(2-(3,4,5-trimethoxystyryl)phenyl)acrylamide(8u),
(E)-3-(4-Amino-3-methoxyphenyl)-N-(2-(3,4,5-trimethoxystyryl)phenyl)acrylamide(8v), (E)-3-(3,4-Dihydroxyphenyl)-N-(2-(3,4,5-trimethoxystyryl)phenyl)acrylamide(8w),
(E)-3-(3-Hydroxy-4-methoxyphenyl)-N-(2-(3,4,5-trimethoxystyryl)phenyl)acrylamide(8x),
(E)-3-(4-Methoxy-3-nitrophenyl)-N-(2-(3,4,5-trimethoxystyryl)phenyl)acrylamide(8y),
(E)-3-(3-Amino-4-methoxyphenyl)-N-(2-(3,4,5-trimethoxystyryl)phenyl)acrylamide(8z),
(E)-3-(3,4-Difluorophenyl)-N-(2-(3,4,5-trimethoxystyryl)phenyl)acrylamide(8aa),
(E)-3-(3,4,5-Trimethoxyphenyl)-N-(2-(3,4,5-trimethoxystyryl)phenyl)acrylamide(8ab),
(E)-3-(3,4-Dimethoxy-5-nitrophenyl)-N-(2-(3,4,5-trimethoxystyryl)phenyl)acrylamide(8ac),
(E)-3-(3-Amino-4, 5-dimethoxyphenyl)-N-(2-(3,4,5-trimethoxystyryl)phenyl)acrylamide(8ad),
(E)-3-(1H-Indol-3-yl)-N-(2-(3,4,5-trimethoxystyryl)phenyl)acrylamide(8ae), (E)-3-(1-Methyl-1H-indol-3-yl)-N-(2-(3,4,5-trimethoxystyryl)phenyl)acrylamide(8af),
N-(3-(3,4,5-Trimethoxystyryl)phenyl)cinnamamide(9a),
(E)-3-(2-Methoxyphenyl)-N-(3-(3,4,5-trimethoxystyryl)phenyl)acrylamide(9b),
(E)-3-(2-Hydroxyphenyl)-N-(3-(3,4,5-trimethoxystyryl)phenyl)acrylamide(9c),
(E)-3-(2-Nitrophenyl)-N-(3-(3,4,5-trimethoxystyryl)phenyl)acrylamide(9d),
(E)-3-(2-Aminophenyl)-N-(3-(3,4,5-trimethoxystyryl)phenyl)acrylamide(9e),
(E)-3-(3-Methoxyphenyl)-N-(3-(3,4,5-trimethoxystyryl)phenyl)acrylamide(9f),
(E)-3-(3-Hydroxyphenyl)-N-(3-(3,4,5-trimethoxystyryl)phenyl)acrylamide(9g),
(E)-3-(3-(Prop-2-ynyloxy)phenyl)-N-(3-(3,4,5-trimethoxystyryl)phenyl)acrylamide(9h),
(E)-3-(3-(Allyloxy)phenyl)-N-(3-(3,4,5-trimethoxystyryl)phenyl)acrylamide(9i),
(E)-3-(3-Nitrophenyl)-N-(3-(3,4,5-trimethoxystyryl)phenyl)acrylamide(9j),
(E)-3-(3-Aminophenyl)-N-(3-(3,4,5-trimethoxystyryl)phenyl)acrylamide(9k),
(E)-3-(4-Methoxyphenyl)-N-(3-(3,4,5-trimethoxystyryl)phenyl)acrylamide(9l),
(E)-3-(4-Hydroxyphenyl)-N-(3-(3,4,5-trimethoxystyryl)phenyl)acrylamide(9m),
(E)-3-(4-(Trifluoromethyl)phenyl)-N-(3-(3,4,5-trimethoxystyryl)phenyl)acrylamide(9n),
(E)-3-(4-Nitrophenyl)-N-(3-(3,4,5-trimethoxystyryl)phenyl)acrylamide(9o),
(E)-3-(4-Aminophenyl)-N-(3-(3,4,5-trimethoxystyryl)phenyl)acrylamide(9p),
(E)-3-(4-Chlorophenyl)-N-(3-(3,4,5-trimethoxystyryl)phenyl)acrylamide(9q),
(E)-3-(4-Fluorophenyl)-N-(3-(3,4,5-trimethoxystyryl)phenyl)acrylamide(9r),
(E)-3-(3,4-Dimethoxyphenyl)-N-(3-(3,4,5-trimethoxystyryl)phenyl)acrylamide(9s),
(E)-3-(4-Hydroxy-3-methoxyphenyl)-N-(3-(3,4,5-trimethoxystyryl)phenyl)acrylamide(9t),
(E)-3-(3-Methoxy-4-nitrophenyl)-N-(3-(3,4,5-trimethoxystyryl)phenyl)acrylamide(9u),
(E)-3-(4-Amino-3-methoxyphenyl)-N-(3-(3,4,5-trimethoxystyryl)phenyl)acrylamide(9v),
(E)-3-(3,4-Dihydroxyphenyl)-N-(3-(3,4,5-trimethoxystyryl)phenyl)acrylamide(9w),
(E)-3-(3-Hydroxy-4-methoxyphenyl)-N-(3-(3,4,5-trimethoxystyryl)phenyl)acrylamide(9x),
(E)-3-(4-Methoxy-3-nitrophenyl)-N-(3-(3,4,5-trimethoxystyryl)phenyl)acrylamide(9y),
(E)-3-(3-Amino-4-methoxyphenyl)-N-(3-(3,4,5-trimethoxystyryl)phenyl)acrylamide(9z),
(E)-3-(3,4-Difluorophenyl)-N-(3-(3,4,5-trimethoxystyryl)phenyl)acrylamide(9aa),
(E)-3-(3,4,5-Trimethoxyphenyl)-N-(3-(3,4,5-trimethoxystyryl)phenyl)acrylamide(9ab),
(E)-3-(3,4-Dimethoxy-5-nitrophenyl)-N-(3-(3,4,5-trimethoxystyryl)phenyl)acrylamide(9ac),
(E)-3-(3-Amino-4, 5-dimethoxyphenyl)-N-(3-(3,4,5-trimethoxystyryl)phenyl)acrylamide(9ad),
(E)-3-(1H-Indol-3-yl)-N-(3-(3,4,5-trimethoxystyryl)phenyl)acrylamide(9ae),
(E)-3-(1-Methyl-1H-indol-3-yl)-N-(3-(3,4,5-trimethoxystyryl)phenyl)acrylamide(9af),
N-(4-(3,4,5-Trimethoxystyryl)phenyl)cinnamamide(10a),
(E)-3-(2-Methoxyphenyl)-N-(4-(3,4,5-trimethoxystyryl)phenyl)acrylamide(10b),
(E)-3-(2-hydroxyphenyl)-N-(4-(3,4,5-trimethoxystyryl)phenyl)acrylamide(10c),
(E)-3-(2-Nitrophenyl)-N-(4-(3,4,5-trimethoxystyryl)phenyl)acrylamide(10d),
(E)-3-(2-Aminophenyl)-N-(4-(3,4,5-trimethoxystyryl)phenyl)acrylamide(10e),
(E)-3-(3-Methoxyphenyl)-N-(4-(3,4,5-trimethoxystyryl)phenyl)acrylamide(10f),
(E)-3-(3-Hydroxyphenyl)-N-(4-(3,4,5-trimethoxystyryl)phenyl)acrylamide(10g),
(E)-3-(3-(Prop-2-ynyloxy)phenyl)-N-(4-(3,4,5-trimethoxystyryl)phenyl)acrylamide(10h),
(E)-3-(3-(Allyloxy)phenyl)-N-(4-(3,4,5-trimethoxystyryl)phenyl)acrylamide(10i),
(E)-3-(3-Nitrophenyl)-N-(4-(3,4,5-trimethoxystyryl)phenyl)acrylamide(10j),
(E)-3-(3-Aminophenyl)-N-(4-(3,4,5-trimethoxystyryl)phenyl)acrylamide(10k),
(E)-3-(4-Methoxyphenyl)-N-(4-(3,4,5-trimethoxystyryl)phenyl)acrylamide(10l),
(E)-3-(4-Hydroxyphenyl)-N-(4-(3,4,5-trimethoxystyryl)phenyl)acrylamide(10m),
(E)-3-(4-(Trifluoromethyl)phenyl)-N-(4-(3,4,5-trimethoxystyryl)phenyl)acrylamide(10n),
(E)-3-(4-Nitrophenyl)-N-(4-(3,4,5-trimethoxystyryl)phenyl)acrylamide(10o),
(E)-3-(4-Aminophenyl)-N-(4-(3,4,5-trimethoxystyryl)phenyl)acrylamide(10p),
(E)-3-(4-Chlorophenyl)-N-(4-(3,4,5-trimethoxystyryl)phenyl)acrylamide(10q),
(E)-3-(4-Fluorophenyl)-N-(4-(3,4,5-trimethoxystyryl)phenyl)acrylamide(10r),
(E)-3-(3,4-Dimethoxyphenyl)-N-(4-(3,4,5-trimethoxystyryl)phenyl)acrylamide(10s),
(E)-3-(4-Hydroxy-3-methoxyphenyl)-N-(4-(3,4,5-trimethoxystyryl)phenyl)acrylamide(10t),
(E)-3-(3-Methoxy-4-nitrophenyl)-N-(4-(3,4,5-trimethoxystyryl)phenyl)acrylamide(10u),
(E)-3-(4-Amino-3-methoxyphenyl)-N-(4-(3,4,5-trimethoxystyryl)phenyl)acrylamide(10v),
(E)-3-(3,4-Dihydroxyphenyl)-N-(4-(3,4,5-trimethoxystyryl)phenyl)acrylamide(10w),
(E)-3-(3-Hydroxy-4-methoxyphenyl)-N-(4-(3,4,5-trimethoxystyryl)phenyl)acrylamide(10x),
(E)-3-(4-Methoxy-3-nitrophenyl)-N-(4-(3,4,5-trimethoxystyryl)phenyl)acrylamide(10y),
(E)-3-(3-Amino-4-methoxyphenyl)-N-(4-(3,4,5-trimethoxystyryl)phenyl)acrylamide(10z), (E)-3-(3,4-Difluorophenyl)-N-(4-(3,4,5-trimethoxystyryl)phenyl)acrylamide(10aa),
(E)-3-(3,4,5-Trimethoxyphenyl)-N-(4-(3,4,5-trimethoxystyryl)phenyl)acrylamide(10ab),
(E)-3-(3,4-Dimethoxy-5-nitrophenyl)-N-(4-(3,4,5-trimethoxystyryl)phenyl)acrylamide(10ac),
(E)-3-(3-Amino-4, 5-dimethoxyphenyl)-N-(4-(3,4,5-trimethoxystyryl)phenyl)acrylamide(10ad),
(E)-3-(1H-Indol-3-yl)-N-(4-(3,4,5-trimethoxystyryl)phenyl)acrylamide(10ae),
(E)-3-(1-Methyl-1H-indol-3-yl)-N-(4-(3,4,5-trimethoxystyryl)phenyl)acrylamide(10af), N-(2-Methoxy-6-(3,4,5-trimethoxystyryl)phenyl)cinnamamide(11a),
(E)-N-(2-Methoxy-6-(3,4,5-trimethoxystyryl)phenyl)-3-(2-methoxyphenyl)acrylamide(11b),
(E)-3-(2-Hydroxyphenyl)-N-(2-methoxy-6-(3,4,5-trimethoxystyryl)phenyl)acrylamide(11c),
(E)-N-(2-Methoxy-6-(3,4,5-trimethoxystyryl)phenyl)-3-(2-nitrophenyl)acrylamide(11d),
(E)-3-(2-Aminophenyl)-N-(2-methoxy-6-(3,4,5-trimethoxystyryl)phenyl)acrylamide(11e),
(E)-N-(2-Methoxy-6-(3,4,5-trimethoxystyryl)phenyl)-3-(3-methoxyphenyl)acrylamide(11f),
(E)-3-(3-Hydroxyphenyl)-N-(2-methoxy-6-(3,4,5-trimethoxystyryl)phenyl)acrylamide(11g),
(E)-N-(2-Methoxy-6-(3,4,5-trimethoxystyryl)phenyl)-3-(3-(prop-2-ynyloxy)phenyl)acrylamide(11h),
(E)-3-(3-(Allyloxy)phenyl)-N-(2-methoxy-6-(3,4,5-trimethoxystyryl)phenyl)acrylamide(11i),
(E)-N-(2-Methoxy-6-(3,4,5-trimethoxystyryl)phenyl)-3-(3-nitrophenyl)acrylamide(11j),
(E)-3-(3-Aminophenyl)-N-(2-methoxy-6-(3,4,5-trimethoxystyryl)phenyl)acrylamide(11k),
(E)-N-(2-Methoxy-6-(3,4,5-trimethoxystyryl)phenyl)-3-(4-methoxyphenyl)acrylamide(11l),
(E)-3-(4-Hydroxyphenyl)-N-(2-methoxy-6-(3,4,5-trimethoxystyryl)phenyl)acrylamide(11m),
(E)-N-(2-Methoxy-6-(3,4,5-trimethoxystyryl)phenyl)-3-(4-trifluoromethyl)phenyl)acryl amide(11n),
(E)-N-(2-Methoxy-6-(3,4,5-trimethoxystyryl)phenyl)-3-(4-nitrophenyl)acrylamide(11o),
(E)-3-(4-Aminophenyl)-N-(2-methoxy-6-(3,4,5-trimethoxystyryl)phenyl)acrylamide(11p),
(E)-3-(4-Chlorophenyl)-N-(2-methoxy-6-(3,4,5-trimethoxystyryl)phenyl)acrylamide(11q),
(E)-3-(4-Fluorophenyl)-N-(2-methoxy-6-(3,4,5-trimethoxystyryl)phenyl)acrylamide(11 r),
(E)-3-(3,4-Dimethoxyphenyl)-N-(2-methoxy-6-(3,4,5-trimethoxystyryl)phenyl)acrylamide(11s),
(E)-3-(4-Hydroxy-3-methoxyphenyl)-N-(2-methoxy-6-(3,4,5-trimethoxystyryl)phenyl)acrylamide(11t),
(E)-3-(3-Methoxy-4-nitrophenyl)-N-(2-methoxy-6-(3,4,5-trimethoxystyryl)phenyl)acrylamide(11u),
(E)-3-(4-Amino-3-methoxyphenyl)-N-(2-methoxy-6-(3,4,5-trimethoxystyryl)phenyl)acrylamide(11v),
(E)-3-(3,4-Dihydroxyphenyl)-N-(2-methoxy-6-(3,4,5-trimethoxystyryl)phenyl)acrylamide(11w),
(E)-3-(3-Hydroxy-4-methoxyphenyl)-N-(2-methoxy-6-(3,4,5-trimethoxystyryl)phenyl)acrylamide(11X),
(E)-3-(4-Methoxy-3-nitrophenyl)-N-(2-methoxy-6-(3,4,5-trimethoxystyryl)phenyl)acrylamide(11y),
(E)-3-(3-Amino-4-methoxyphenyl)-N-(2-methoxy-6-(3,4,5-trimethoxystyryl)phenyl)acrylamide(11z),
(E)-3-(3,4-Difluorophenyl)-N-(2-methoxy-6-(3,4,5-trimethoxystyryl)phenyl)acrylamide(11aa),
(E)-N-(2-Methoxy-6-(3,4,5-trimethoxystyryl)phenyl)-3-(3,4,5-trimethoxyphenyl)acrylamide(11ab),
(E)-3-(3,4-Dimethoxy-5-nitrophenyl)-N-(2-methoxy-6-(3,4,5-trimethoxystyryl)phenyl)acrylamide(11ac),
(E)-3-(3-Amino-4, 5-dimethoxyphenyl)-N-(2-methoxy-6-(3,4,5-trimethoxystyryl)phenyl)acrylamide(11ad),
(E)-3-(1H-Indol-3-yl)-N-(2-methoxy-6-(3,4,5-trimethoxystyryl)phenyl)acrylamide(11ae),
(E)-N-(2-Methoxy-6-(3,4,5-trimethoxystyryl)phenyl)-3-(1-methyl-1H-indol-3-yl)acrylamide(11af),
N-(2-Hydroxy-6-(3,4,5-trimethoxystyryl)phenyl)cinnamamide(12a),
(E)-N-(2-Hydroxy-6-(3,4,5-trimethoxystyryl)phenyl)-3-(2-methoxyphenyl)acrylamide(12b),
(E)-N-(2-Hydroxy-6-(3,4,5-trimethoxystyryl)phenyl)-3-(2-hydroxyphenyl)acrylamide(12c),
(E)-N-(2-Hydroxy-6-(3,4,5-trimethoxystyryl)phenyl)-3-(2-nitrophenyl)acrylamide(12d),
(E)-3-(2-Aminophenyl)-N-(2-hydroxy-6-(3,4,5-trimethoxystyryl)phenyl)acrylamide(12e),
(E)-N-(2-Hydroxy-6-(3,4,5-trimethoxystyryl)phenyl)-3-(3-methoxyphenyl)acrylamide(12f),
(E)-N-(2-Hydroxy-6-(3,4,5-trimethoxystyryl)phenyl)-3-(3-hydroxyphenyl)acrylamide(12g),
(E)-N-(2-Hydroxy-6-(3,4,5-trimethoxystyryl)phenyl)-3-(3-(prop-2-ynyloxy)phenyl)acrylamide(12h),
(E)-3-(3-(Allyloxy)phenyl)-N-(2-hydroxy-6-(3,4,5-trimethoxystyryl)phenyl)acrylamide(12i),
(E)-N-(2-Hydroxy-6-(3,4,5-trimethoxystyryl)phenyl)-3-(3-nitrophenyl)acrylamide(12j),
(E)-3-(3-Aminophenyl)-N-(2-hydroxy-6-(3,4,5-trimethoxystyryl)phenyl)acrylamide(12k),
(E)-N-(2-Hydroxy-6-(3,4,5-trimethoxystyryl)phenyl)-3-(4-methoxyphenyl)acrylamide(12l),
(E)-N-(2-Hydroxy-6-(3,4,5-trimethoxystyryl)phenyl)-3-(4-hydroxyphenyl)acrylamide(12m),
(E)-N-(2-Hydroxy-6-(3,4,5-trimethoxystyryl)phenyl)-3-(4-(trifluoromethyl)phenyl)acrylamide(12n),
(E)-N-(2-Hydroxy-6-(3,4,5-trimethoxystyryl)phenyl)-3-(4-nitrophenyl)acrylamide(12o),
(E)-3-(4-Aminophenyl)-N-(2-hydroxy-6-(3,4,5-trimethoxystyryl)phenyl)acrylamide(12p),
(E)-3-(4-Chlorophenyl)-N-(2-hydroxy-6-(3,4,5-trimethoxystyryl)phenyl)acrylamide(12q),
(E)-3-(4-Fluorophenyl)-N-(2-hydroxy-6-(3,4,5-trimethoxystyryl)phenyl)acrylamide(12r),
(E)-3-(3,4-Dimethoxyphenyl)-N-(2-hydroxy-6-(3,4,5-trimethoxystyryl)phenyl)acrylamide(12s),
(E)-3-(4-Hydroxy-3-methoxyphenyl)-N-(2-hydroxy-6-(3,4,5-trimethoxystyryl)phenyl)acrylamide(12t),
(E)-N-(2-hydroxy-6-(3,4,5-trimethoxystyryl)phenyl)-3-(3-methoxy-4-nitrophenyl)acrylamide(12u),
(E)-3-(4-Amino-3-methoxyphenyl)-N-(2-hydroxy-6-(3,4,5-trimethoxystyryl)phenyl)acrylamide(12v),
(E)-3-(3,4-Dihydroxyphenyl)-N-(2-hydroxy-6-(3,4,5-trimethoxystyryl)phenyl)acrylamide(12w),
(E)-3-(3-Hydroxy-4-methoxyphenyl)-N-(2-hydroxy-6-(3,4,5-trimethoxystyryl)phenyl)acrylamide(12x),
(E)-N-(2-Hydroxy-6-(3,4,5-trimethoxystyryl)phenyl)-3-(4-methoxy-3-nitrophenyl)acrylamide(12y),
(E)-3-(3-Amino-4-methoxyphenyl)-N-(2-hydroxy-6-(3,4,5-trimethoxystyryl)phenyl)acrylamide(12z),
(E)-3-(3,4-Difluorophenyl)-N-(2-hydroxy-6-(3,4,5-trimethoxystyryl)phenyl)acrylamide(12aa),
(E)-N-(2-Hydroxy-6-(3,4,5-trimethoxystyryl)phenyl)-3-(3,4,5-trimethoxyphenyl)acrylamide(12ab),
(E)-3-(3,4-Dimethoxy-5-nitrophenyl)-N-(2-hydroxy-6-(3,4,5-trimethoxystyryl)phenyl)acrylamide(12ac), (E)-3-(3-Amino-4, 5-dimethoxyphenyl)-N-(2-hydroxy-6-(3,4,5-trimethoxystyryl)phenyl)acrylamide(12ad),
(E)-N-(2-Hydroxy-6-(3,4,5-trimethoxystyryl)phenyl)-3-(1H-indol-3-yl)acrylamide(12ae),
(E)-N-(2-Hydroxy-6-(3,4,5-trimethoxystyryl)phenyl)-3-(1-methyl-1H-indol-3-yl)acrylamide(12af),
N-(5-Methoxy-2-(3,4,5-trimethoxystyryl)phenyl)cinnamamide(13a),
(E)-N-(5-Methoxy-2-(3,4,5-trimethoxystyryl)phenyl)-3-(2-methoxyphenyl)acrylamide (13b),
(E)-3-(2-Hydroxyphenyl)-N-(5-methoxy-2-(3,4,5-trimethoxystyryl)phenyl)acryl amide(13c),
(E)-N-(5-Methoxy-2-(3,4,5-trimethoxystyryl)phenyl)-3-(2-nitrophenyl)acrylamide(13d),
(E)-3-(2-Aminophenyl)-N-(5-methoxy-2-(3,4,5-trimethoxystyryl)phenyl)acrylamide(13e),
(E)-N-(5-Methoxy-2-(3,4,5-trimethoxystyryl)phenyl)-3-(3-methoxyphenyl)acrylamide(13f),
(E)-3-(3-Hydroxyphenyl)-N-(5-methoxy-2-(3,4,5-trimethoxystyryl)phenyl)acryl amide(13g),
(E)-N-(5-Methoxy-2-(3,4,5-trimethoxystyryl)phenyl)-3-(3-(prop-2-ynyloxy)phenyl)acrylamide(13h),
(E)-3-(3-(Allyloxy)phenyl)-N-(5-methoxy-2-(3,4,5-trimethoxystyryl)phenyl)acrylamide (13i),
(E)-N-(5-Methoxy-2-(3,4,5-trimethoxystyryl)phenyl)-3-(3-nitrophenyl)acrylamide(13j),
(E)-3-(3-Aminophenyl)-N-(5-methoxy-2-(3,4,5-trimethoxystyryl)phenyl)acrylamide(13k),
(E)-N-(5-Methoxy-2-(3,4,5-trimethoxystyryl)phenyl)-3-(4-methoxyphenyl)acrylamide(13l),
(E)-3-(4-Hydroxyphenyl)-N-(5-methoxy-2-(3,4,5-trimethoxystyryl)phenyl)acryl amide(13m),
(E)-N-(5-methoxy-2-(3,4,5-trimethoxystyryl)phenyl)-3-(4-(trifluoromethyl)phenyl)acrylamide(13n),
(E)-N-(5-Methoxy-2-(3,4,5-trimethoxystyryl)phenyl)-3-(4-nitrophenyl)acrylamide(13o),
(E)-3-(4-Aminophenyl)-N-(5-methoxy-2-(3,4,5-trimethoxystyryl)phenyl)acrylamide(13p),
(E)-3-(4-Chlorophenyl)-N-(5-methoxy-2-(3,4,5-trimethoxystyryl)phenyl)acrylamide(13q),
(E)-3-(4-Fluorophenyl)-N-(5-methoxy-2-(3,4,5-trimethoxystyryl)phenyl)acrylamide(13r),
(E)-3-(3,4-Dimethoxyphenyl)-N-(5-methoxy-2-(3,4,5-trimethoxystyryl)phenyl)acrylamide(13s),
(E)-3-(4-Hydroxy-3-methoxyphenyl)-N-(5-methoxy-2-(3,4,5-trimethoxystyryl)phenyl)acrylamide(13t),
(E)-N-(5-Methoxy-2-(3,4,5-trimethoxystyryl)phenyl)-3-(3-methoxy-4-nitrophenyl)acrylamide(13u),
(E)-3-(4-Amino-3-methoxyphenyl)-N-(5-methoxy-2-(3, 4,5-trimethoxystyryl)phenyl)acrylamide(13v),
(E)-3-(3,4-Dihydroxyphenyl)-N-(5-methoxy-2-(3,4,5-trimethoxystyryl)phenyl)acrylamide(13w),
(E)-3-(3-Hydroxy-4-methoxyphenyl)-N-(5-methoxy-2-(3,4,5-trimethoxystyryl)phenyl)acrylamide(13x),
(E)-N-(5-Methoxy-2-(3,4,5-trimethoxystyryl)phenyl)-3-(4-methoxy-3-nitrophenyl)acrylamide(13y),
(E)-3-(3-Amino-4-methoxyphenyl)-N-(5-methoxy-2-(3, 4,5-trimethoxystyryl)phenyl)acrylamide(13z),
(E)-3-(3,4-Difluorophenyl)-N-(5-methoxy-2-(3,4,5-trimethoxystyryl)phenyl)acrylamide(13aa),
(E)-N-(5-Methoxy-2-(3,4,5-trimethoxystyryl)phenyl)-3-(3,4,5-trimethoxyphenyl)acrylamide(13ab),
(E)-3-(3,4-Dimethoxy-5-nitrophenyl)-N-(5-methoxy-2-(3,4,5-trimethoxystyryl)phenyl)acrylamide(13ac),
(E)-3-(3-Amino-4, 5-dimethoxyphenyl)-N-(5-methoxy-2-(3,4,5-trimethoxystyryl)phenyl)acrylamide(13ad),
(E)-3-(1H-Indol-3-yl)-N-(5-methoxy-2-(3,4,5-trimethoxystyryl)phenyl)acrylamide(13ae),
(E)-N-(5-Methoxy-2-(3,4,5-trimethoxystyryl)phenyl)-3-(1-methyl-1H-indol-3-yl)acrylamide(13af),
N-(4-Methoxy-2-(3,4,5-trimethoxystyryl)phenyl)cinnamamide(14a),
(E)-N-(4-Methoxy-2-(3,4,5-trimethoxystyryl)phenyl)-3-(2-methoxyphenyl)acrylamide(14b),
(E)-3-(2-Hydroxyphenyl)-N-(4-methoxy-2-(3,4,5-trimethoxystyryl)phenyl)acrylamide(14c),
(E)-N-(4-Methoxy-2-(3,4,5-trimethoxystyryl)phenyl)-3-(2-nitrophenyl)acrylamide(14d),
(E)-3-(2-Aminophenyl)-N-(4-methoxy-2-(3,4,5-trimethoxystyryl)phenyl)acrylamide(14e),
(E)-N-(4-Methoxy-2-(3,4,5-trimethoxystyryl)phenyl)-3-(3-methoxyphenyl)acrylamide(14f),
(E)-3-(3-Hydroxyphenyl)-N-(4-methoxy-2-(3,4,5-trimethoxystyryl)phenyl)acrylamide(14g),
(E)-N-(4-Methoxy-2-(3,4,5-trimethoxystyryl)phenyl)-3-(3-(prop-2-ynyloxy)phenyl)acrylamide(14h),
(E)-3-(3-(Allyloxy)phenyl)-N-(4-methoxy-2-(3,4,5-trimethoxystyryl)phenyl)acrylamide(14i),
(E)-N-(4-Methoxy-2-(3,4,5-trimethoxystyryl)phenyl)-3-(3-nitrophenyl)acrylamide(14j),
(E)-3-(3-Aminophenyl)-N-(4-methoxy-2-(3,4,5-trimethoxystyryl)phenyl)acrylamide(14k),
(E)-N-(4-Methoxy-2-(3,4,5-trimethoxystyryl)phenyl)-3-(4-methoxyphenyl)acrylamide(14l),
(E)-3-(4-Hydroxyphenyl)-N-(4-methoxy-2-(3,4,5-trimethoxystyryl)phenyl)acrylamide(14m),
(E)-N-(4-Methoxy-2-(3,4,5-trimethoxystyryl)phenyl)-3-(4-(trifluoromethyl)phenyl)acrylamide(14n),
(E)-N-(4-Methoxy-2-(3,4,5-trimethoxystyryl)phenyl)-3-(4-nitrophenyl)acrylamide(14o),
(E)-3-(4-Aminophenyl)-N-(4-methoxy-2-(3,4,5-trimethoxystyryl)phenyl)acrylamide(14p),
(E)-3-(4-Chlorophenyl)-N-(4-methoxy-2-(3,4,5-trimethoxystyryl)phenyl)acrylamide(14q),
(E)-3-(4-Fluorophenyl)-N-(4-methoxy-2-(3,4,5-trimethoxystyryl)phenyl)acrylamide(14r),
(E)-3-(3,4-Dimethoxyphenyl)-N-(4-methoxy-2-(3,4,5-trimethoxystyryl)phenyl)acrylamide(14s),
(E)-3-(4-Hydroxy-3-methoxyphenyl)-N-(4-methoxy-2-(3,4,5-trimethoxystyryl)phenyl)acrylamide(14t),
(E)-N-(4-Methoxy-2-(3,4,5-trimethoxystyryl)phenyl)-3-(3-methoxy-4-nitrophenyl)acrylamide(14u),
(E)-3-(4-Amino-3-methoxyphenyl)-N-(4-methoxy-2-(3, 4,5-trimethoxystyryl)phenyl)acrylamide(14v),
(E)-3-(3,4-Dihydroxyphenyl)-N-(4-methoxy-2-(3,4,5-trimethoxystyryl)phenyl)acrylamide(14w)
(E)-3-(3-Hydroxy-4-methoxyphenyl)-N-(4-methoxy-2-(3,4,5-trimethoxystyryl)phenyl)acrylamide(14x),
(E)-N-(4-Methoxy-2-(3,4,5-trimethoxystyryl)phenyl)-3-(4-methoxy-3-nitrophenyl)acrylamide(14y),
(E)-3-(3-Amino-4-methoxyphenyl)-N-(4-methoxy-2-(3, 4,5-trimethoxystyryl)phenyl)acrylamide(14z),
(E)-3-(3,4-Difluorophenyl)-N-(4-methoxy-2-(3,4,5-trimethoxystyryl)phenyl)acrylamide(14aa)
(E)-N-(4-Methoxy-2-(3,4,5-trimethoxystyryl)phenyl)-3-(3,4,5-trimethoxyphenyl)acrylamide(14ab),
(E)-3-(3,4-Dimethoxy-5-nitrophenyl)-N-(4-methoxy-2-(3,4,5-trimethoxystyryl)phenyl)acrylamide(14ac),
(E)-3-(3-Amino-4, 5-dimethoxyphenyl)-N-(4-methoxy-2-(3,4,5-trimethoxystyryl)phenyl)acrylamide(14ad),
(E)-3-(1H-Indol-3-yl)-N-(4-methoxy-2-(3,4,5-trimethoxystyryl)phenyl)acrylamide(14ae), (E)-N-(4-Methoxy-2-(3,4,5-trimethoxystyryl)phenyl)-3-(1-methyl-1H-indol-3-yl)acrylamide(14f),
N-(2-Methoxy-5-(3,4,5-trimethoxystyryl)phenyl)cinnamamide(15a),
(E)-N-(2-Methoxy-5-(3,4,5-trimethoxystyryl)phenyl)-3-(2-methoxyphenyl)acrylamide(15b),
(E)-3-(2-Hydroxyphenyl)-N-(2-methoxy-5-(3,4,5-trimethoxystyryl)phenyl)acrylamide(15c),
(E)-N-(2-Methoxy-5-(3,4,5-trimethoxystyryl)phenyl)-3-(2-nitrophenyl)acrylamide(15d),
(E)-3-(2-Aminophenyl)-N-(2-methoxy-5-(3,4,5-trimethoxystyryl)phenyl)acrylamide(15e),
(E)-N-(2-Methoxy-5-(3,4,5-trimethoxystyryl)phenyl)-3-(3-methoxyphenyl)acrylamide(15f),
(E)-3-(3-Hydroxyphenyl)-N-(2-methoxy-5-(3,4,5-trimethoxystyryl)phenyl)acrylamide(15g),
(E)-N-(2-Methoxy-5-(3,4,5-trimethoxystyryl)phenyl)-3-(3-(prop-2-ynyloxy)phenyl)acrylamide(15h),
(E)-3-(3-(Allyloxy)phenyl)-N-(2-methoxy-5-(3,4,5-trimethoxystyryl)phenyl)acrylamide(15i),
(E)-N-(2-Methoxy-5-(3,4,5-trimethoxystyryl)phenyl)-3-(3-nitrophenyl)acrylamide(15j),
(E)-3-(3-Aminophenyl)-N-(2-methoxy-5-(3,4,5-trimethoxystyryl)phenyl)acrylamide(15k),
(E)-N-(2-Methoxy-5-(3,4,5-trimethoxystyryl)phenyl)-3-(4-methoxyphenyl)acrylamide(15l),
(E)-3-(4-Hydroxyphenyl)-N-(2-methoxy-5-(3,4,5-trimethoxystyryl)phenyl)acrylamide(15m),
(E)-N-(2-Methoxy-5-(3,4,5-trimethoxystyryl)phenyl)-3-(4-(trifluoromethyl)phenyl)acrylamide(15n),
(E)-N-(2-Methoxy-5-(3,4,5-trimethoxystyryl)phenyl)-3-(4-nitrophenyl)acrylamide(15o),
(E)-3-(4-Aminophenyl)-N-(2-methoxy-5-(3,4,5-trimethoxystyryl)phenyl)acrylamide(15p),
(E)-3-(4-Chlorophenyl)-N-(2-methoxy-5-(3,4,5-trimethoxystyryl)phenyl)acrylamide(15q),
(E)-3-(4-Fluorophenyl)-N-(2-methoxy-5-(3,4,5-trimethoxystyryl)phenyl)acrylamide(15r),
(E)-3-(3,4-Dimethoxyphenyl)-N-(2-methoxy-5-(3,4,5-trimethoxystyryl)phenyl)acrylamide(15s),
(E)-3-(4-Hydroxy-3-methoxyphenyl)-N-(2-methoxy-5-(3,4,5-trimethoxystyryl)phenyl)acrylamide(15t),
(E)-3-(3-Methoxy-4-nitrophenyl)-N-(2-methoxy-5-(3,4,5-trimethoxystyryl)phenyl)acrylamide(15u),
(E)-3-(4-Amino-3-methoxyphenyl)-N-(2-methoxy-5-(3,4,5-trimethoxystyryl)phenyl)acrylamide(15v),
(E)-3-(3,4-Dihydroxyphenyl)-N-(2-methoxy-5-(3,4,5-trimethoxystyryl)phenyl)acrylamide(15w),
(E)-3-(3-Hydroxy-4-methoxyphenyl)-N-(2-methoxy-5-(3,4,5-trimethoxystyryl)phenyl)acrylamide(15x),
(E)-3-(4-Methoxy-3-nitrophenyl)-N-(2-methoxy-5-(3,4,5-trimethoxystyryl)phenyl)acrylamide(15y),
(E)-3-(3-Amino-4-methoxyphenyl)-N-(2-methoxy-5-(3,4,5-trimethoxystyryl)phenyl)acrylamide(15z),
(E)-3-(3,4-Difluorophenyl)-N-(2-methoxy-5-(3,4,5-trimethoxystyryl)phenyl)acrylamide(15aa),
(E)-N-(2-Methoxy-5-(3,4,5-trimethoxystyryl)phenyl)-3-(3,4,5-trimethoxyphenyl)acrylamide(15ab),
(E)-3-(3,4-Dimethoxy-5-nitrophenyl)-N-(2-methoxy-5-(3,4,5-trimethoxystyryl)phenyl)acrylamide(15ac),
(E)-3-(3-Amino-4,5-dimethoxyphenyl)-N-(2-methoxy-5-(3,4,5-trimethoxystyryl)phenyl)acrylamide(15ad),
(E)-3-(1H-Indol-3-yl)-N-(2-methoxy-5-(3,4,5-trimethoxystyryl)phenyl)acrylamide(15ae),
(E)-N-(2-Methoxy-5-(3,4,5-trimethoxystyryl)phenyl)-3-(1-methyl-1H-indol-3-yl)acrylamide(15af),
N-(2-Hydroxy-5-(3,4,5-trimethoxystyryl)phenyl)cinnamamide(16a),
(E)-N-(2-Hydroxy-5-(3,4,5-trimethoxystyryl)phenyl)-3-(2-methoxyphenyl)acrylamide(16b),
(E)-N-(2-Hydroxy-5-(3,4,5-trimethoxystyryl)phenyl)-3-(2-hydroxyphenyl)acrylamide(16c),
(E)-N-(2-Hydroxy-5-(3,4,5-trimethoxystyryl)phenyl)-3-(2-nitrophenyl)acrylamide(16d),
(E)-3-(2-Aminophenyl)-N-(2-hydroxy-5-(3,4,5-trimethoxystyryl)phenyl)acrylamide(16e),
(E)-N-(2-Hydroxy-5-(3,4,5-trimethoxystyryl)phenyl)-3-(3-methoxyphenyl)acrylamide(16f),
(E)-N-(2-Hydroxy-5-(3,4,5-trimethoxystyryl)phenyl)-3-(3-hydroxyphenyl)acrylamide(16g),
(E)-N-(2-Hydroxy-5-(3,4,5-trimethoxystyryl)phenyl)-3-(3-(prop-2-ynyloxy)phenyl)acrylamide(16h),
(E)-3-(3-(Allyloxy)phenyl)-N-(2-hydroxy-5-(3,4,5-trimethoxystyryl)phenyl)acrylamide(16i),
(E)-N-(2-Hydroxy-5-(3,4,5-trimethoxystyryl)phenyl)-3-(3-nitrophenyl)acrylamide(16j),
(E)-3-(3-Aminophenyl)-N-(2-hydroxy-5-(3,4,5-trimethoxystyryl)phenyl)acrylamide(16k),
(E)-N-(2-Hydroxy-5-(3,4,5-trimethoxystyryl)phenyl)-3-(4-methoxyphenyl)acrylamide(16l),
(E)-N-(2-Hydroxy-5-(3,4,5-trimethoxystyryl)phenyl)-3-(4-hydroxyphenyl)acrylamide(16m),
(E)-N-(2-Hydroxy-5-(3,4,5-trimethoxystyryl)phenyl)-3-(4-(trifluoromethyl)phenyl)acrylamide(16n),
(E)-N-(2-Hydroxy-5-(3,4,5-trimethoxystyryl)phenyl)-3-(4-nitrophenyl)acrylamide(16o),
(E)-3-(4-Aminophenyl)-N-(2-hydroxy-5-(3,4,5-trimethoxystyryl)phenyl)acrylamide(16p),
(E)-3-(4-Chlorophenyl)-N-(2-hydroxy-5-(3,4,5-trimethoxystyryl)phenyl)acrylamide(16q),
(E)-3-(4-Fluorophenyl)-N-(2-hydroxy-5-(3,4,5-trimethoxystyryl)phenyl)acrylamide(16r),
(E)-3-(3,4-Dimethoxyphenyl)-N-(2-hydroxy-5-(3,4,5-trimethoxystyryl)phenyl)acrylamide(16s),
(E)-3-(4-Hydroxy-3-methoxyphenyl)-N-(2-hydroxy-5-(3,4,5-trimethoxystyryl)phenyl)acrylamide(16o),
(E)-N-(2-Hydroxy-5-(3,4,5-trimethoxystyryl)phenyl)-3-(3-methoxy-4-nitrophenyl)acrylamide(16u),
(E)-3-(4-Amino-3-methoxyphenyl)-N-(2-hydroxy-5-(3,4,5-trimethoxystyryl)phenyl)acrylamide(16v),
(E)-3-(3,4-Dihydroxyphenyl)-N-(2-hydroxy-5-(3,4,5-trimethoxystyryl)phenyl)acrylamide(16w),
(E)-3-(3-Hydroxy-4-methoxyphenyl)-N-(2-hydroxy-5-(3,4,5-trimethoxystyryl)phenyl)acrylamide(16x),
(E)-N-(2-Hydroxy-5-(3,4,5-trimethoxystyryl)phenyl)-3-(4-methoxy-3-nitrophenyl)acrylamide(16y),
(E)-3-(3-Amino-4-methoxyphenyl)-N-(2-hydroxy-5-(3,4,5-trimethoxystyryl)phenyl)acrylamide(16z),
(E)-3-(3,4-Difluorophenyl)-N-(2-hydroxy-5-(3,4,5-trimethoxystyryl)phenyl)acrylamide(16aa),
(E)-N-(2-Hydroxy-5-(3,4,5-trimethoxystyryl)phenyl)-3-(3,4,5-trimethoxyphenyl)acrylamide(16ab),
(E)-3-(3,4-Dimethoxy-5-nitrophenyl)-N-(2-hydroxy-5-(3,4,5-trimethoxystyryl)phenyl)acrylamide(16ac),
(E)-3-(3-Amino-4,5-dimethoxyphenyl)-N-(2-hydroxy-5-(3,4,5-trimethoxystyryl)phenyl)acrylamide(16ad),
(E)-N-(2-Hydroxy-5-(3,4,5-trimethoxystyryl)phenyl)-3-(1H-indol-3-yl)acrylamide(16ae),
(E)-N-(2-Hydroxy-5-(3,4,5-trimethoxystyryl)phenyl)-3-(1-methyl-1H-indol-3-yl)acrylamide(16af), N-(2-Methoxy-4-(3,4,5-trimethoxystyryl)phenyl)cinnamamide(17a),
(E)-N-(2-Methoxy-4-(3,4,5-trimethoxystyryl)phenyl)-3-(2-methoxyphenyl)acrylamide(17b),
(E)-3-(2-Hydroxyphenyl)-N-(2-methoxy-4-(3,4,5-trimethoxystyryl)phenyl)acrylamide(17c),
(E)-N-(2-Methoxy-4-(3,4,5-trimethoxystyryl)phenyl)-3-(2-nitrophenyl)acrylamide(17d),
(E)-3-(2-Aminophenyl)-N-(2-methoxy-4-(3,4,5-trimethoxystyryl)phenyl)acrylamide(17e),
(E)-N-(2-Methoxy-4-(3,4,5-trimethoxystyryl)phenyl)-3-(3-methoxyphenyl)acrylamide(17f),
(E)-3-(3-Hydroxyphenyl)-N-(2-methoxy-4-(3,4,5-trimethoxystyryl)phenyl)acrylamide(17g),
(E)-N-(2-Methoxy-4-(3,4,5-trimethoxystyryl)phenyl)-3-(3-(prop-2-ynyloxy)phenyl)acrylamide(17h),
(E)-3-(3-(Allyloxy)phenyl)-N-(2-methoxy-4-(3,4,5-trimethoxystyryl)phenyl)acrylamide(17i),
(E)-N-(2-Methoxy-4-(3,4,5-trimethoxystyryl)phenyl)-3-(3-nitrophenyl)acrylamide(17j),
(E)-3-(3-Aminophenyl)-N-(2-methoxy-4-(3,4,5-trimethoxystyryl)phenyl)acrylamide(17k),
(E)-N-(2-Methoxy-4-(3,4,5-trimethoxystyryl)phenyl)-3-(4-methoxyphenyl)acrylamide(17l),
(E)-3-(4-Hydroxyphenyl)-N-(2-methoxy-4-(3,4,5-trimethoxystyryl)phenyl)acrylamide(17m),
(E)-N-(2-Methoxy-4-(3,4,5-trimethoxystyryl)phenyl)-3-(4-(trifluoromethyl)phenyl)acrylamide(17n),
(E)-N-(2-Methoxy-4-(3,4,5-trimethoxystyryl)phenyl)-3-(4-nitrophenyl)acrylamide(17o),
(E)-3-(4-Aminophenyl)-N-(2-methoxy-4-(3,4,5-trimethoxystyryl)phenyl)acrylamide(17p),
(E)-3-(4-Chlorophenyl)-N-(2-methoxy-4-(3,4,5-trimethoxystyryl)phenyl)acrylamide(17q),
(E)-3-(4-Fluorophenyl)-N-(2-methoxy-4-(3,4,5-trimethoxystyryl)phenyl)acrylamide(17r),
(E)-3-(3,4-Dimethoxyphenyl)-N-(2-methoxy-4-(3,4,5-trimethoxystyryl)phenyl)acrylamide(17s),
(E)-3-(4-Hydroxy-3-methoxyphenyl)-N-(2-methoxy-4-(3,4,5-trimethoxystyryl)phenyl)acrylamide(17t),
(E)-N-(2-Methoxy-4-(3,4,5-trimethoxystyryl)phenyl)-3-(3-methoxy-4-nitrophenyl)acrylamide(17u),
(E)-3-(4-Amino-3-methoxyphenyl)-N-(2-methoxy-4-(3,4,5-trimethoxystyryl)phenyl)acrylamide(17v),
(E)-3-(3,4-Dihydroxyphenyl)-N-(2-methoxy-4-(3,4,5-trimethoxystyryl)phenyl)acrylamide(17w),
(E)-3-(3-Hydroxy-4-methoxyphenyl)-N-(2-methoxy-4-(3,4,5-trimethoxystyryl)phenyl)acrylamide(17x),
(E)-3-(4-Methoxy-3-nitrophenyl)-N-(2-methoxy-4-(3,4,5-trimethoxystyryl)phenyl)acrylamide(17y),
(E)-3-(3-Amino-4-methoxyphenyl)-N-(2-methoxy-4-(3,4,5-trimethoxystyryl)phenyl)acrylamide(17z),
(E)-3-(3,4-Difluorophenyl)-N-(2-methoxy-4-(3,4,5-trimethoxystyryl)phenyl)acrylamide(17aa),
(E)-N-(2-Methoxy-4-(3,4,5-trimethoxystyryl)phenyl)-3-(3,4,5-trimethoxyphenyl)acrylamide(17ab),
(E)-3-(3,4-Dimethoxy-5-nitrophenyl)-N-(2-methoxy-4-(3,4,5-trimethoxystyryl)phenyl)acrylamide(17ac),
(E)-3-(3-Amino-4,5-dimethoxyphenyl)-N-(2-methoxy-4-(3,4,5-trimethoxystyryl)phenyl)acrylamide(17ad),
(E)-3-(1H-Indol-3-yl)-N-(2-methoxy-4-(3,4,5-trimethoxystyryl)phenyl)acrylamide(17ae),
(E)-N-(2-Methoxy-4-(3,4,5-trimethoxystyryl)phenyl)-3-(1-methyl-1H-indol-3-yl)acrylamide(17af),
N-(2-Hydroxy-4-(3,4,5-trimethoxystyryl)phenyl)cinnamamide(18a),
(E)-N-(2-Hydroxy-4-(3,4,5-trimethoxystyryl)phenyl)-3-(2-methoxyphenyl)acrylamide(18b),
(E)-N-(2-Hydroxy-4-(3,4,5-trimethoxystyryl)phenyl)-3-(2-hydroxyphenyl)acrylamide(18c),
(E)-N-(2-Hydroxy-4-(3,4,5-trimethoxystyryl)phenyl)-3-(2-nitrophenyl)acrylamide(18d),
(E)-3-(2-Aminophenyl)-N-(2-hydroxy-4-(3,4,5-trimethoxystyryl)phenyl)acrylamide(18e),
(E)-N-(2-Hydroxy-4-(3,4,5-trimethoxystyryl)phenyl)-3-(3-methoxyphenyl)acrylamide(18f),
(E)-N-(2-Hydroxy-4-(3,4,5-trimethoxystyryl)phenyl)-3-(3-hydroxyphenyl)acrylamide(18g),
(E)-N-(2-Hydroxy-4-(3,4,5-trimethoxystyryl)phenyl)-3-(3-(prop-2-ynyloxy)phenyl)acrylamide(18h),
(E)-3-(3-(Allyloxy)phenyl)-N-(2-hydroxy-4-(3,4,5-trimethoxystyryl)phenyl)acrylamide(18i),
(E)-N-(2-Hydroxy-4-(3,4,5-trimethoxystyryl)phenyl)-3-(3-nitrophenyl)acrylamide(18j),
(E)-3-(3-Aminophenyl)-N-(2-hydroxy-4-(3,4,5-trimethoxystyryl)phenyl)acrylamide(18k),
(E)-N-(2-Hydroxy-4-(3,4,5-trimethoxystyryl)phenyl)-3-(4-methoxyphenyl)acrylamide(18l),
(E)-N-(2-Hydroxy-4-(3,4,5-trimethoxystyryl)phenyl)-3-(4-hydroxyphenyl)acrylamide(18m),
(E)-N-(2-Hydroxy-4-(3,4,5-trimethoxystyryl)phenyl)-3-(4-(trifluoromethyl)phenyl)acrylamide(18n),
(E)-N-(2-Hydroxy-4-(3,4,5-trimethoxystyryl)phenyl)-3-(4-nitrophenyl)acrylamide(18o),
(E)-3-(4-Aminophenyl)-N-(2-hydroxy-4-(3,4,5-trimethoxystyryl)phenyl)acrylamide(18p),
(E)-3-(4-Chlorophenyl)-N-(2-hydroxy-4-(3,4,5-trimethoxystyryl)phenyl)acrylamide(18q),
(E)-3-(4-Fluorophenyl)-N-(2-hydroxy-4-(3,4,5-trimethoxystyryl)phenyl)acrylamide(18r),
(E)-3-(3,4-Dimethoxyphenyl)-N-(2-hydroxy-4-(3,4,5-trimethoxystyryl)phenyl)acrylamide(18s),
(E)-3-(4-Hydroxy-3-methoxyphenyl)-N-(2-hydroxy-4-(3,4,5-trimethoxystyryl)phenyl)acrylamide(18t),
(E)-N-(2-Hydroxy-4-(3,4,5-trimethoxystyryl)phenyl)-3-(3-methoxy-4-nitrophenyl)acrylamide(18u),
(E)-3-(4-Amino-3-methoxyphenyl)-N-(2-hydroxy-4-(3,4,5-trimethoxystyryl)phenyl)acrylamide(18v),
(E)-3-(3,4-Dihydroxyphenyl)-N-(2-hydroxy-4-(3,4,5-trimethoxystyryl)phenyl)acrylamide(18w),
(E)-N-(2-Hydroxy-4-(3,4,5-trimethoxystyryl)phenyl)-3-(3-hydroxy-4-methoxyphenyl)acrylamide(18x),
(E)-N-(2-Hydroxy-4-(3,4,5-trimethoxystyryl)phenyl)-3-(4-methoxy-3-nitrophenyl)acrylamide(18y),
(E)-3-(3-Amino-4-methoxyphenyl)-N-(2-hydroxy-4-(3,4,5-trimethoxystyryl)phenyl)acrylamide(18z),
(E)-3-(3,4-Difluorophenyl)-N-(2-hydroxy-4-(3,4,5-trimethoxystyryl)phenyl)acrylamide(18aa),
(E)-N-(2-Hydroxy-4-(3,4,5-trimethoxystyryl)phenyl)-3-(3,4,5-trimethoxyphenyl)acrylamide(18ab),
(E)-3-(3,4-Dimethoxy-5-nitrophenyl)-N-(2-hydroxy-4-(3,4,5-trimethoxystyryl)phenyl)acrylamide(18ac),
(E)-3-(3-Amino-4,5-dimethoxyphenyl)-N-(2-hydroxy-4-(3,4,5-trimethoxystyryl)phenyl)acrylamide(18ad),
(E)-N-(2-Hydroxy-4-(3,4,5-trimethoxystyryl)phenyl)-3-(1H-indol-3-yl)acrylamide(18ae),
(E)-N-(2-Hydroxy-4-(3,4,5-trimethoxystyryl)phenyl)-3-(1-methyl-1H-indol-3-yl)acrylamide(18af),
N-(2,3-Dimethoxy-6-(3,4,5-trimethoxystyryl)phenyl)cinnamamide(19a),
(E)-N-(2,3-Dimethoxy-6-(3,4,5-trimethoxystyryl)phenyl)-3-(2-methoxyphenyl)acrylamide(19b), (E)-N-(2,3-Dimethoxy-6-(3,4,5-trimethoxystyryl)phenyl)-3-(2-hydroxyphenyl)acrylamide(19c),
(E)-N-(2,3-Dimethoxy-6-(3,4,5-trimethoxystyryl)phenyl)-3-(2-nitrophenyl)acrylamide(19d),
(E)-3-(2-Aminophenyl)-N-(2,3-dimethoxy-6-(3,4,5-trimethoxystyryl)phenyl)acrylamide(19e),
(E)-N-(2,3-Dimethoxy-6-(3,4,5-trimethoxystyryl)phenyl)-3-(3-methoxyphenyl)acrylamide(19f),
(E)-N-(2,3-Dimethoxy-6-(3,4,5-trimethoxystyryl)phenyl)-3-(3-hydroxyphenyl)acrylamide(19g),
(E)-N-(2,3-Dimethoxy-6-(3,4,5-trimethoxystyryl)phenyl)-3-(3-(prop-2-ynyloxy)phenyl)acrylamide(19h),
(E)-3-(3-(Allyloxy)phenyl)-N-(2,3-dimethoxy-6-(3,4,5-trimethoxystyryl)phenyl)acrylamide(19i),
(E)-N-(2,3-Dimethoxy-6-(3,4,5-trimethoxystyryl)phenyl)-3-(3-nitrophenyl)acrylamide(19j),
(E)-3-(3-Aminophenyl)-N-(2,3-dimethoxy-6-(3,4,5-trimethoxystyryl)phenyl)acrylamide(19k),
(E)-N-(2,3-Dimethoxy-6-(3,4,5-trimethoxystyryl)phenyl)-3-(4-methoxyphenyl)acrylamide(19l),
(E)-N-(2,3-Dimethoxy-6-(3,4,5-trimethoxystyryl)phenyl)-3-(4-hydroxyphenyl)acrylamide(19m),
(E)-N-(2,3-Dimethoxy-6-(3,4,5-trimethoxystyryl)phenyl)-3-(4-(trifluoromethyl)phenyl)acrylamide(19n),
(E)-N-(2,3-Dimethoxy-6-(3,4,5-trimethoxystyryl)phenyl)-3-(4-nitrophenyl)acrylamide(19o),
(E)-3-(4-Aminophenyl)-N-(2,3-dimethoxy-6-(3,4,5-trimethoxystyryl)phenyl)acrylamide(19p),
(E)-3-(4-Chlorophenyl)-N-(2,3-dimethoxy-6-(3,4,5-trimethoxystyryl)phenyl)acrylamide(19q),
(E)-N-(2,3-Dimethoxy-6-(3,4,5-trimethoxystyryl)phenyl)-3-(4-fluorophenyl)acrylamide(19r),
(E)-N-(2,3-Dimethoxy-6-(3,4,5-trimethoxystyryl)phenyl)-3-(3,4-dimethoxyphenyl)acrylamide(19s),
(E)-N-(2,3-Dimethoxy-6-(3,4,5-trimethoxystyryl)phenyl)-3-(4-hydroxy-3-methoxyphenyl)acrylamide(19t),
(E)-N-(2,3-Dimethoxy-6-(3,4,5-trimethoxystyryl)phenyl)-3-(3-methoxy-4-nitrophenyl)acrylamide(19u),
(E)-3-(4-Amino-3-methoxyphenyl)-N-(2,3-dimethoxy-6-(3,4,5-trimethoxystyryl)phenyl)acrylamide(19v),
(E)-3-(3,4-Dihydroxyphenyl)-N-(2,3-dimethoxy-6-(3,4,5-trimethoxystyryl)phenyl)acrylamide(19w),
(E)-N-(2,3-Dimethoxy-6-(3,4,5-trimethoxystyryl)phenyl)-3-(3-hydroxy-4-methoxyphenyl)acrylamide(19x),
(E)-N-(2,3-Dimethoxy-6-(3,4,5-trimethoxystyryl)phenyl)-3-(4-methoxy-3-nitrophenyl)acrylamide(19y),
(E)-3-(3-Amino-4-methoxyphenyl)-N-(2,3-dimethoxy-6-(3,4,5-trimethoxystyryl)phenyl)acrylamide(19z),
(E)-3-(3,4-Difluorophenyl)-N-(2,3-dimethoxy-6-(3,4,5-trimethoxystyryl)phenyl)acrylamide(19aa),
(E)-N-(2,3-Dimethoxy-6-(3,4,5-trimethoxystyryl)phenyl)-3-(3,4,5-trimethoxyphenyl)acrylamide(19ab),
(E)-3-(3,4-Dimethoxy-5-nitrophenyl)-N-(2,3-dimethoxy-6-(3,4,5-trimethoxystyryl)phenyl)acrylamide(19ac),
(E)-3-(3-Amino-4,5-dimethoxyphenyl)-N-(2,3-dimethoxy-6-(3,4,5-trimethoxystyryl)phenyl)acrylamide(19ad),
(E)-N-(2,3-Dimethoxy-6-(3,4,5-trimethoxystyryl)phenyl)-3-(1H-indol-3-yl)acrylamide(19ae),
(E)-N-(2,3-Dimethoxy-6-(3,4,5-trimethoxystyryl)phenyl)-3-(1-methyl-1H-indol-3-yl)acrylamide(19af),
N-(2-Hydroxy-3-methoxy-6-(3,4,5-trimethoxystyryl)phenyl)cinnamamide(20a),
(E)-N-(2-Hydroxy-3-methoxy-6-(3,4,5-trimethoxystyryl)phenyl)-3-(2-methoxyphenyl)acrylamide(20b),
(E)-N-(2-hydroxy-3-methoxy-6-(3,4,5-trimethoxystyryl)phenyl)-3-(2-hydroxyphenyl)acrylamide(20c),
(E)-N-(2-Hydroxy-3-methoxy-6-(3,4,5-trimethoxystyryl)phenyl)-3-(2-nitrophenyl)acrylamide(20d),
(E)-3-(2-Aminophenyl)-N-(2-hydroxy-3-methoxy-6-(3,4,5-trimethoxystyryl)phenyl)acrylamide(20e),
(E)-N-(2-Hydroxy-3-methoxy-6-(3,4,5-trimethoxystyryl)phenyl)-3-(3-methoxyphenyl)acrylamide(20f),
(E)-N-(2-Hydroxy-3-methoxy-6-(3,4,5-trimethoxystyryl)phenyl)-3-(3-hydroxyphenyl)acrylamide(20g),
(E)-N-(2-Hydroxy-3-methoxy-6-(3,4,5-trimethoxystyryl)phenyl)-3-(3-(prop-2-ynyloxy)phenyl)acrylamide(20h),
(E)-3-(3-(Allyloxy)phenyl)-N-(2-hydroxy-3-methoxy-6-(3,4,5-trimethoxystyryl)phenyl)acrylamide(20i),
(E)-N-(2-Hydroxy-3-methoxy-6-(3,4,5-trimethoxystyryl)phenyl)-3-(3-nitrophenyl)acrylamide(20j),
(E)-3-(3-Aminophenyl)-N-(2-hydroxy-3-methoxy-6-(3,4,5-trimethoxystyryl)phenyl)acrylamide(20k),
(E)-N-(2-Hydroxy-3-methoxy-6-(3,4,5-trimethoxystyryl)phenyl)-3-(4-methoxyphenyl)acrylamide(20l),
(E)-N-(2-Hydroxy-3-methoxy-6-(3,4,5-trimethoxystyryl)phenyl)-3-(4-hydroxyphenyl)acrylamide(20m),
(E)-N-(2-Hydroxy-3-methoxy-6-(3,4,5-trimethoxystyryl)phenyl)-3-(4-(trifluoromethyl)phenyl)acrylamide(20n),
(E)-N-(2-Hydroxy-3-methoxy-6-(3,4,5-trimethoxystyryl)phenyl)-3-(4-nitrophenyl)acrylamide(20o),
(E)-3-(4-Aminophenyl)-N-(2-hydroxy-3-methoxy-6-(3,4,5-trimethoxystyryl)phenyl)acrylamide(20p),
(E)-3-(4-Chlorophenyl)-N-(2-hydroxy-3-methoxy-6-(3,4,5-trimethoxystyryl)phenyl)acrylamide(20q),
(E)-3-(4-Fluorophenyl)-N-(2-hydroxy-3-methoxy-6-(3,4,5-trimethoxystyryl)phenyl)acrylamide(20r),
(E)-3-(3,4-Dimethoxyphenyl)-N-(2-hydroxy-3-methoxy-6-(3,4,5-trimethoxystyryl)phenyl)acrylamide(20s),
(E)-N-(2-Hydroxy-3-methoxy-6-(3,4,5-trimethoxystyryl)phenyl)-3-(4-hydroxy-3-methoxyphenyl)acrylamide(20t),
(E)-N-(2-Hydroxy-3-methoxy-6-(3,4,5-trimethoxystyryl)phenyl)-3-(3-methoxy-4-nitrophenyl)acrylamide(20u),
(E)-3-(4-Amino-3-methoxyphenyl)-N-(2-hydroxy-3-methoxy-6-(3,4,5-trimethoxystyryl)phenyl)acrylamide(20v),
(E)-3-(3,4-Dihydroxyphenyl)-N-(2-hydroxy-3-methoxy-6-(3,4,5-trimethoxystyryl)phenyl)acrylamide(20w),
(E)-N-(2-Hydroxy-3-methoxy-6-(3,4,5-trimethoxystyryl)phenyl)-3-(3-hydroxy-4-methoxyphenyl)acrylamide(20x),
(E)-N-(2-Hydroxy-3-methoxy-6-(3,4,5-trimethoxystyryl)phenyl)-3-(4-methoxy-3-nitrophenyl)acrylamide(20y),
(E)-3-(3-Amino-4-methoxyphenyl)-N-(2-hydroxy-3-methoxy-6-(3,4,5-trimethoxystyryl)phenyl)acrylamide(20z),
(E)-3-(3,4-Difluorophenyl)-N-(2-hydroxy-3-methoxy-6-(3,4,5-trimethoxystyryl)phenyl)acrylamide(20aa),
(E)-N-(2-Hydroxy-3-methoxy-6-(3,4,5-trimethoxystyryl)phenyl)-3-(3,4,5-trimethoxyphenyl)acrylamide(20ab),
(E)-3-(3,4-Dimethoxy-5-nitrophenyl)-N-(2-hydroxy-3-methoxy-6-(3,4,5-trimethoxystyryl)phenyl)acrylamide(20ac),
(E)-3-(3-Amino-4,5-dimethoxyphenyl)-N-(2-hydroxy-3-methoxy-6-(3,4,5-trimethoxystyryl)phenyl)acrylamide(20ad),
(E)-N-(2-Hydroxy-3-methoxy-6-(3,4,5-trimethoxystyryl)phenyl)-3-(1H-indol-3-yl)acrylamide(20ae), (E)-N-(2-Hydroxy-3-methoxy-6-(3,4,5-trimethoxystyryl) phenyl)-3-(1-methyl-1H-indol-3-yl)acrylamide(20af),
N-(3-Hydroxy-2-methoxy-6-(3,4,5-trimethoxystyryl) phenyl)cinnamamide(21a),
(E)-N-(3-Hydroxy-2-methoxy-6-(3,4,5-trimethoxystyryl) phenyl)-3-(2-methoxyphenyl)acryl amide(21b),
(E)-N-(3-Hydroxy-2-methoxy-6-(3,4,5-trimethoxystyryl) phenyl)-3-(2-hydroxyphenyl)acrylamide(21c),
(E)-N-(3-Hydroxy-2-methoxy-6-(3,4,5-trimethoxystyryl) phenyl)-3-(2-nitrophenyl)acrylamide(21d),
(E)-3-(2-Aminophenyl)-N-(3-hydroxy-2-methoxy-6-(3,4,5-trimethoxystyryl)phenyl)acrylamide(21e),
(E)-N-(3-Hydroxy-2-methoxy-6-(3,4,5-trimethoxystyryl) phenyl)-3-(3-methoxyphenyl)acryl amide(21f),
(E)-N-(3-Hydroxy-2-methoxy-6-(3,4,5-trimethoxystyryl) phenyl)-3-(3-hydroxyphenyl)acrylamide(21g),
(E)-N-(3-Hydroxy-2-methoxy-6-(3,4,5-trimethoxystyryl) phenyl)-3-(3-(prop-2-ynyloxy)phenyl)acrylamide (21h),
(E)-3-(3-(Allyloxy)phenyl)-N-(3-hydroxy-2-methoxy-6-(3,4,5-trimethoxystyryl)phenyl)acrylamide(21i),
(E)-N-(3-Hydroxy-2-methoxy-6-(3,4,5-trimethoxystyryl) phenyl)-3-(3-nitrophenyl)acrylamide(21j),
(E)-3-(3-Aminophenyl)-N-(3-hydroxy-2-methoxy-6-(3,4,5-trimethoxystyryl)phenyl)acrylamide(21k),
(E)-N-(3-Hydroxy-2-methoxy-6-(3,4,5-trimethoxystyryl) phenyl)-3-(4-methoxyphenyl)acryl amide(21l),
(E)-N-(3-Hydroxy-2-methoxy-6-(3,4,5-trimethoxystyryl) phenyl)-3-(4-hydroxyphenyl)acrylamide(21m),
(E)-N-(3-Hydroxy-2-methoxy-6-(3,4,5-trimethoxystyryl) phenyl)-3-(4-(trifluoromethyl)phenyl)acrylamide (21n),
(E)-N-(3-Hydroxy-2-methoxy-6-(3,4,5-trimethoxystyryl) phenyl)-3-(4-nitrophenyl)acrylamide(21o),
(E)-3-(4-Aminophenyl)-N-(3-hydroxy-2-methoxy-6-(3,4,5-trimethoxystyryl)phenyl)acrylamide(21p),
(E)-3-(4-Chlorophenyl)-N-(3-hydroxy-2-methoxy-6-(3,4,5-trimethoxystyryl)phenyl)acrylamide(21q),
(E)-3-(4-Fluorophenyl)-N-(3-hydroxy-2-methoxy-6-(3,4,5-trimethoxystyryl)phenyl)acrylamide(21r),
(E)-3-(3,4-Dimethoxyphenyl)-N-(3-hydroxy-2-methoxy-6-(3,4,5-trimethoxystyryl)phenyl)acrylamide(21s),
(E)-N-(3-Hydroxy-2-methoxy-6-(3,4,5-trimethoxystyryl) phenyl)-3-(4-hydroxy-3-methoxyphenyl)acryl amide (21t),
(E)-N-(3-Hydroxy-2-methoxy-6-(3,4,5-trimethoxystyryl) phenyl)-3-(3-methoxy-4-nitrophenyl)acrylamide(21u),
(E)-3-(4-Amino-3-methoxyphenyl)-N-(3-hydroxy-2-methoxy-6-(3,4,5-trimethoxystyryl)phenyl)acrylamide (21v),
(E)-3-(3,4-Dihydroxyphenyl)-N-(3-hydroxy-2-methoxy-6-(3,4,5-trimethoxystyryl)phenyl)acrylamide(21w),
(E)-N-(3-Hydroxy-2-methoxy-6-(3,4,5-trimethoxystyryl) phenyl)-3-(3-hydroxy-4-methoxyphenyl)acryl amide (21x),
(E)-N-(3-Hydroxy-2-methoxy-6-(3,4,5-trimethoxystyryl) phenyl)-3-(4-methoxy-3-nitrophenyl)acrylamide(21y),
(E)-3-(3-Amino-4-methoxyphenyl)-N-(3-hydroxy-2-methoxy-6-(3,4,5-trimethoxystyryl)phenyl)acrylamide (21z),
(E)-3-(3,4-Difluorophenyl)-N-(3-hydroxy-2-methoxy-6-(3,4,5-trimethoxystyryl)phenyl)acrylamide(21aa),
(E)-N-(3-Hydroxy-2-methoxy-6-(3,4,5-trimethoxystyryl) phenyl)-3-(3,4,5-trimethoxyphenyl)acrylamide(21ab),
(E)-3-(3,4-Dimethoxy-5-nitrophenyl)-N-(3-hydroxy-2-methoxy-6-(3,4,5-trimethoxystyryl)phenyl)acrylamide (21ac),
(E)-3-(3-Amino-4, 5-dimethoxyphenyl)-N-(3-hydroxy-2-methoxy-6-(3,4,5-trimethoxystyryl)phenyl)acrylamide (21ad),
(E)-N-(3-Hydroxy-2-methoxy-6-(3,4,5-trimethoxystyryl) phenyl)-3-(1H-indol-3-yl)acrylamide(21ae),
(E)-N-(3-Hydroxy-2-methoxy-6-(3,4,5-trimethoxystyryl) phenyl)-3-(1-methyl-1H-indol-3-yl)acrylamide(21af),
N-(2,3-Dimethoxy-5-(3,4,5-trimethoxystyryl)phenyl)cinnamamide(22a),
(E)-N-(2,3-Dimethoxy-5-(3,4,5-trimethoxystyryl)phenyl)-3-(2-methoxyphenyl)acrylamide(22b),
(E)-N-(2,3-Dimethoxy-5-(3,4,5-trimethoxystyryl)phenyl)-3-(2-hydroxyphenyl)acrylamide(22c),
(E)-N-(2,3-Dimethoxy-5-(3,4,5-trimethoxystyryl)phenyl)-3-(2-nitrophenyl)acrylamide(22d),
(E)-3-(2-Aminophenyl)-N-(2,3-dimethoxy-5-(3,4,5-trimethoxystyryl)phenyl)acrylamide(22e),
(E)-N-(2, 3-Dimethoxy-5-(3,4,5-trimethoxystyryl)phenyl)-3-(3-methoxyphenyl)acrylamide(22f),
(E)-N-(2, 3-Dimethoxy-5-(3,4,5-trimethoxystyryl)phenyl)-3-(3-hydroxyphenyl)acrylamide(22g),
(E)-N-(2, 3-Dimethoxy-5-(3,4,5-trimethoxystyryl)phenyl)-3-(3-(prop-2-ynyloxy)phenyl)acrylamide(22h),
(E)-3-(3-(Allyloxy)phenyl)-N-(2,3-dimethoxy-5-(3,4,5-trimethoxystyryl)phenyl)acrylamide(22i),
(E)-N-(2, 3-Dimethoxy-5-(3,4,5-trimethoxystyryl)phenyl)-3-(3-nitrophenyl)acrylamide(22j),
(E)-3-(3-Aminophenyl)-N-(2,3-dimethoxy-5-(3,4,5-trimethoxystyryl)phenyl)acrylamide(22k),
(E)-N-(2, 3-Dimethoxy-5-(3,4,5-trimethoxystyryl)phenyl)-3-(4-methoxyphenyl)acrylamide(22l),
(E)-N-(2, 3-Dimethoxy-5-(3,4,5-trimethoxystyryl)phenyl)-3-(4-hydroxyphenyl)acrylamide(22m),
(E)-N-(2,3-Dimethoxy-5-(3,4,5-trimethoxystyryl)phenyl)-3-(4-(trifluoromethyl)phenyl)acrylamide(22n),
(E)-N-(2, 3-Dimethoxy-5-(3,4,5-trimethoxystyryl)phenyl)-3-(4-nitrophenyl)acrylamide(22o),
(E)-3-(4-Aminophenyl)-N-(2,3-dimethoxy-5-(3,4,5-trimethoxystyryl)phenyl)acrylamide(22p),
(E)-3-(4-Chlorophenyl)-N-(2,3-dimethoxy-5-(3,4,5-trimethoxystyryl)phenyl)acrylamide(22q),
(E)-N-(2, 3-Dimethoxy-5-(3,4,5-trimethoxystyryl)phenyl)-3-(4-fluorophenyl)acrylamide(22r),
(E)-N-(2, 3-Dimethoxy-5-(3,4,5-trimethoxystyryl)phenyl)-3-(3,4-dimethoxyphenyl)acrylamide(22s),
(E)-N-(2,3-Dimethoxy-5-(3,4,5-trimethoxystyryl)phenyl)-3-(4-hydroxy-3-methoxyphenyl)acrylamide(22t),
(E)-N-(2,3-Dimethoxy-5-(3,4,5-trimethoxystyryl)phenyl)-3-(3-methoxy-4-nitrophenyl)acrylamide(22u),
(E)-3-(4-Amino-3-methoxyphenyl)-N-(2,3-dimethoxy-5-(3,4,5-trimethoxystyryl)phenyl)acrylamide(22v),
(E)-3-(3,4-Dihydroxyphenyl)-N-(2,3-dimethoxy-5-(3,4,5-trimethoxystyryl)phenyl)acrylamide(22w),
(E)-N-(2,3-Dimethoxy-5-(3,4,5-trimethoxystyryl)phenyl)-3-(3-hydroxy-4-methoxyphenyl)acrylamide(22x),
(E)-N-(2,3-Dimethoxy-5-(3,4,5-trimethoxystyryl)phenyl)-3-(4-methoxy-3-nitrophenyl)acrylamide(22y),
(E)-3-(3-Amino-4-methoxyphenyl)-N-(2,3-dimethoxy-5-(3,4,5-trimethoxystyryl)phenyl)acrylamide(22z),
(E)-3-(3,4-Difluorophenyl)-N-(2,3-dimethoxy-5-(3,4,5-trimethoxystyryl)phenyl)acrylamide(22aa),
(E)-N-(2,3-Dimethoxy-5-(3,4,5-trimethoxystyryl)phenyl)-3-(3,4,5-trimethoxyphenyl)acrylamide(22ab),
(E)-N-(2,3-Dimethoxy-5-(3,4,5-trimethoxystyryl)phenyl)-3-(3,4-dimethoxy-5-nitrophenyl)acrylamide (22ac), (E)-3-(3-Amino-4,5-dimethoxyphenyl)-N-(2,3-dimethoxy-5-(3,4,5-trimethoxystyryl)phenyl)acrylamide(22ad),
(E)-N-(2,3-Dimethoxy-5-(3,4,5-trimethoxystyryl)phenyl)-3-(1H-indol-3-yl)acrylamide(22ae),
(E)-N-(2,3-Dimethoxy-5-(3,4,5-trimethoxystyryl)phenyl)-3-(1-methyl-1H-indol-3-yl)acrylamide(22af),
N-(3-Hydroxy-2-methoxy-5-(3,4,5-trimethoxystyryl)phenyl)cinnamamide(23a),
(E)-N-(3-Hydroxy-2-methoxy-5-(3,4,5-trimethoxystyryl)phenyl)-3-(2-methoxyphenyl)acrylamide(23b),
(E)-N-(3-Hydroxy-2-methoxy-5-(3,4,5-trimethoxystyryl)phenyl)-3-(2-hydroxyphenyl)acrylamide(23c),
(E)-N-(3-Hydroxy-2-methoxy-5-(3,4,5-trimethoxystyryl)phenyl)-3-(2-nitrophenyl)acrylamide(23d),
(E)-3-(2-Aminophenyl)-N-(3-hydroxy-2-methoxy-5-(3,4,5-trimethoxystyryl)phenyl)acrylamide(23e),
(E)-N-(3-Hydroxy-2-methoxy-5-(3,4,5-trimethoxystyryl)phenyl)-3-(3-methoxyphenyl)acrylamide(23f),
(E)-N-(3-Hydroxy-2-methoxy-5-(3,4,5-trimethoxystyryl)phenyl)-3-(3-hydroxyphenyl)acrylamide(23g),
(E)-N-(3-Hydroxy-2-methoxy-5-(3,4,5-trimethoxystyryl)phenyl)-3-(3-(prop-2-ynyloxy)phenyl)acrylamide(23h),
(E)-3-(3-(Allyloxy)phenyl)-N-(3-hydroxy-2-methoxy-5-(3,4,5-trimethoxystyryl)phenyl)acrylamide(23i),
(E)-N-(3-Hydroxy-2-methoxy-5-(3,4,5-trimethoxystyryl)phenyl)-3-(3-nitrophenyl)acrylamide(23j),
(E)-3-(3-Aminophenyl)-N-(3-hydroxy-2-methoxy-5-(3,4,5-trimethoxystyryl)phenyl)acrylamide(23k),
(E)-N-(3-Hydroxy-2-methoxy-5-(3,4,5-trimethoxystyryl)phenyl)-3-(4-methoxyphenyl)acryl amide(23l),
(E)-N-(3-Hydroxy-2-methoxy-5-(3,4,5-trimethoxystyryl)phenyl)-3-(4-hydroxyphenyl)acrylamide(23m),
(E)-N-(3-Hydroxy-2-methoxy-5-(3,4,5-trimethoxystyryl)phenyl)-3-(4-(trifluoromethyl)phenyl)acrylamide(23n),
(E)-N-(3-Hydroxy-2-methoxy-5-(3,4,5-trimethoxystyryl)phenyl)-3-(4-nitrophenyl)acrylamide(23o),
(E)-3-(4-Aminophenyl)-N-(3-hydroxy-2-methoxy-5-(3,4,5-trimethoxystyryl)phenyl)acrylamide(23p),
(E)-3-(4-Chlorophenyl)-N-(3-hydroxy-2-methoxy-5-(3,4,5-trimethoxystyryl)phenyl)acrylamide(23q),
(E)-3-(4-Fluorophenyl)-N-(3-hydroxy-2-methoxy-5-(3,4,5-trimethoxystyryl)phenyl)acrylamide(23r),
(E)-3-(3,4-Dimethoxyphenyl)-N-(3-hydroxy-2-methoxy-5-(3,4,5-trimethoxystyryl)phenyl)acrylamide(23s),
(E)-N-(3-Hydroxy-2-methoxy-5-(3,4,5-trimethoxystyryl)phenyl)-3-(4-hydroxy-3-methoxyphenyl)acryl amide(23t),
(E)-N-(3-Hydroxy-2-methoxy-5-(3,4,5-trimethoxystyryl)phenyl)-3-(3-methoxy-4-nitrophenyl)acrylamide(23u),
(E)-3-(4-Amino-3-methoxyphenyl)-N-(3-hydroxy-2-methoxy-5-(3,4,5-trimethoxystyryl)phenyl)acrylamide(23v),
(E)-3-(3,4-Dihydroxyphenyl)-N-(3-hydroxy-2-methoxy-5-(3,4,5-trimethoxystyryl)phenyl)acrylamide(23w),
(E)-N-(3-Hydroxy-2-methoxy-5-(3,4,5-trimethoxystyryl)phenyl)-3-(3-hydroxy-4-methoxyphenyl)acryl amide(23x),
(E)-N-(3-Hydroxy-2-methoxy-5-(3,4,5-trimethoxystyryl)phenyl)-3-(4-methoxy-3-nitrophenyl)acrylamide(23y),
(E)-3-(3-Amino-4-methoxyphenyl)-N-(3-hydroxy-2-methoxy-5-(3,4,5-trimethoxystyryl)phenyl)acrylamide(23z),
(E)-3-(3,4-Difluorophenyl)-N-(3-hydroxy-2-methoxy-5-(3,4,5-trimethoxystyryl)phenyl)acrylamide(23aa),
(E)-N-(3-Hydroxy-2-methoxy-5-(3,4,5-trimethoxystyryl)phenyl)-3-(3,4,5-trimethoxyphenyl)acrylamide(23ab),
(E)-3-(3,4-Dimethoxy-5-nitrophenyl)-N-(3-hydroxy-2-methoxy-5-(3,4,5-trimethoxystyryl)phenyl)acrylamide(23ac),
(E)-3-(3-Amino-4,5-dimethoxyphenyl)-N-(3-hydroxy-2-methoxy-5-(3,4,5-trimethoxystyryl)phenyl)acrylamide(23ad),
(E)-N-(3-Hydroxy-2-methoxy-5-(3,4,5-trimethoxystyryl)phenyl)-3-(1H-indol-3-yl)acrylamide(23ae),
(E)-N-(3-Hydroxy-2-methoxy-5-(3,4,5-trimethoxystyryl)phenyl)-3-(1-methyl-1H-indol-3-yl)acrylamide(23af),
N-(2-Hydroxy-3-methoxy-5-(3,4,5-trimethoxystyryl)phenyl)cinnamamide(24a),
(E)-N-(2-Hydroxy-3-methoxy-5-(3,4,5-trimethoxystyryl)phenyl)-3-(2-methoxyphenyl)acryl amide(24b),
(E)-N-(2-Hydroxy-3-methoxy-5-(3,4,5-trimethoxystyryl)phenyl)-3-(2-hydroxyphenyl)acrylamide(24c),
(E)-N-(2-Hydroxy-3-methoxy-5-(3,4,5-trimethoxystyryl)phenyl)-3-(2-nitrophenyl)acrylamide(24d),
(E)-3-(2-Aminophenyl)-N-(2-hydroxy-3-methoxy-5-(3,4,5-trimethoxystyryl)phenyl)acrylamide(24e),
(E)-N-(2-Hydroxy-3-methoxy-5-(3,4,5-trimethoxystyryl)phenyl)-3-(3-methoxyphenyl)acryl amide(24f),
(E)-N-(2-Hydroxy-3-methoxy-5-(3,4,5-trimethoxystyryl)phenyl)-3-(3-hydroxyphenyl)acrylamide(24g),
(E)-N-(2-Hydroxy-3-methoxy-5-(3,4,5-trimethoxystyryl)phenyl)-3-(3-(prop-2-ynyloxy)phenyl)acrylamide(24h),
(E)-3-(3-(Allyloxy)phenyl)-N-(2-hydroxy-3-methoxy-5-(3,4,5-trimethoxystyryl)phenyl)acrylamide (24i),
(E)-N-(2-Hydroxy-3-methoxy-5-(3,4,5-trimethoxystyryl)phenyl)-3-(3-nitrophenyl)acrylamide(24j),
(E)-3-(3-Aminophenyl)-N-(2-hydroxy-3-methoxy-5-(3,4,5-trimethoxystyryl)phenyl)acrylamide (24k),
(E)-N-(2-Hydroxy-3-methoxy-5-(3,4,5-trimethoxystyryl)phenyl)-3-(4-methoxyphenyl)acryl amide(24l),
(E)-N-(2-Hydroxy-3-methoxy-5-(3,4,5-trimethoxystyryl)phenyl)-3-(4-hydroxyphenyl)acrylamide(24m),
(E)-N-(2-Hydroxy-3-methoxy-5-(3,4,5-trimethoxystyryl)phenyl)-3-(4-(trifluoromethyl)phenyl)acrylamide(24n),
(E)-N-(2-Hydroxy-3-methoxy-5-(3,4,5-trimethoxystyryl)phenyl)-3-(4-nitrophenyl)acrylamide(24o),
(E)-3-(4-Aminophenyl)-N-(2-hydroxy-3-methoxy-5-(3,4,5-trimethoxystyryl)phenyl)acrylamide(24p),
(E)-3-(4-Chlorophenyl)-N-(2-hydroxy-3-methoxy-5-(3,4,5-trimethoxystyryl)phenyl)acrylamide(24q),
(E)-3-(4-Fluorophenyl)-N-(2-hydroxy-3-methoxy-5-(3,4,5-trimethoxystyryl)phenyl)acrylamide (24r),
(E)-3-(3,4-Dimethoxyphenyl)-N-(2-hydroxy-3-methoxy-5-(3,4,5-trimethoxystyryl)phenyl)acrylamide(24s),
(E)-N-(2-Hydroxy-3-methoxy-5-(3,4,5-trimethoxystyryl)phenyl)-3-(4-hydroxy-3-methoxyphenyl)acrylamide(24t),
(E)-N-(2-Hydroxy-3-methoxy-5-(3,4,5-trimethoxystyryl)phenyl)-3-(3-methoxy-4-nitrophenyl)acrylamide(24u),
(E)-3-(4-Amino-3-methoxyphenyl)-N-(2-hydroxy-3-methoxy-5-(3,4,5-trimethoxystyryl)phenyl)acrylamide(24v),
(E)-3-(3,4-Dihydroxyphenyl)-N-(2-hydroxy-3-methoxy-5-(3,4,5-trimethoxystyryl)phenyl)acrylamide(24w),
(E)-N-(2-Hydroxy-3-methoxy-5-(3,4,5-trimethoxystyryl)phenyl)-3-(3-hydroxy-4-methoxyphenyl)acrylamide(24x),
(E)-N-(2-Hydroxy-3-methoxy-5-(3,4,5-trimethoxystyryl)phenyl)-3-(4-methoxy-3-nitrophenyl)acrylamide(24y), (E)-3-(3-Amino-4-methoxyphenyl)-N-(2-hydroxy-3-methoxy-5-(3,4,5-trimethoxystyryl)phenyl)acrylamide (24z), (E)-3-(3,4-Difluorophenyl)-N-(2-hydroxy-3-methoxy-5-(3,4,5-trimethoxystyryl)phenyl)acrylamide(24aa), (E)-N-(2-Hydroxy-3-methoxy-5-(3,4,5-trimethoxystyryl)phenyl)-3-(3,4,5-trimethoxyphenyl)acrylamide(24ab), (E)-3-(3,4-Dimethoxy-5-nitrophenyl)-N-(2-hydroxy-3-methoxy-5-(3,4,5-trimethoxystyryl)phenyl)acrylamide (24ac), (E)-3-(3-Amino-4,5-dimethoxyphenyl)-N-(2-hydroxy-3-methoxy-5-(3,4,5-trimethoxystyryl)phenyl)acrylamide (24ad), (E)-N-(2-Hydroxy-3-methoxy-5-(3,4,5-trimethoxystyryl)phenyl)-3-(1H-indol-3-yl)acrylamide(24ae), or (E)-N-(2-Hydroxy-3-methoxy-5-(3,4,5-trimethoxystyryl)phenyl)-3-(1-methyl-1H-indol-3-yl)acrylamide(24af).

4. A compound as claimed in claim 1, useful as an anticancer agent in the treatment of conditions characterized by abnormal proliferation of the vasculature.

5. A process for preparation of a N-((3,4,5-trimethoxystyryl)aryl)cinnamamide compound of general formula A as claimed in claim 1, formula A

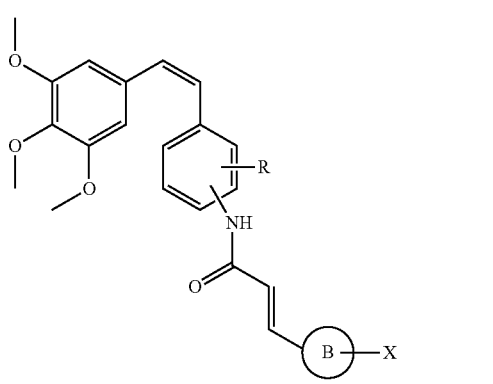

wherein
B is selected from aryl, heteroaryl and fused heteroaryl ring; and
R and X are independently selected from H, hydroxyl, alkyl, alkoxy, prop-2-ynyloxy, allyloxy, halo, alkylhalides, alkoxy halides, nitro, and amine, wherein said process comprises the steps of:
reacting an amino compound of formula 5a-q(1.0 mmol) with an acid chloride compound of formula 7a-z(1.0 mmol) in the presence of triethylamine (3-5 mmol) in dry tetrahydrofuran at about 0° C.,
stirring the reaction mixture for 12-18 h at room temperature,
diluting the stirred reaction mixture with ethyl acetate, and
washing the diluted reaction mixture with water and brine solution, followed by chromatographic purification to obtain the N-((3,4,5-trimethoxystyryl)aryl)cinnamamide compound, 5a-q

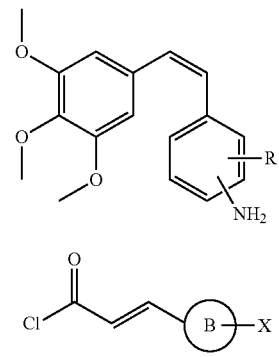

7a-z

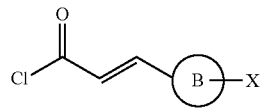

wherein
B is selected from aryl, heteroaryl and fused heteroaryl ring; and
R and X are independently selected from H, hydroxyl, alkyl, alkoxy, prop-2-ynyloxy, allyloxy, halo, alkylhalides, alkoxy halides, nitro, and amine.

* * * * *